(12) United States Patent
Yu et al.

(10) Patent No.: US 11,340,226 B2
(45) Date of Patent: May 24, 2022

(54) SQUALENE EPOXIDASE IN THE DIAGNOSIS AND TREATMENT OF NON-ALCOHOLIC FATTY LIVER DISEASES

(71) Applicant: The Chinese University of Hong Kong, Hong Kong (CN)

(72) Inventors: Jun Yu, Hong Kong (CN); Dabin Liu, Shenzhen (CN); Chi-Chun Wong, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 105 days.

(21) Appl. No.: 15/911,042

(22) Filed: Mar. 2, 2018

(65) Prior Publication Data
US 2019/0271698 A1 Sep. 5, 2019

(51) Int. Cl.
G01N 33/573 (2006.01)
G01N 33/68 (2006.01)
C12Q 1/26 (2006.01)
A61K 49/16 (2006.01)

(52) U.S. Cl.
CPC ............. *G01N 33/573* (2013.01); *C12Q 1/26* (2013.01); *G01N 33/6842* (2013.01); *G01N 33/6893* (2013.01); *A61K 49/16* (2013.01); *C12Y 114/13132* (2013.01); *G01N 2333/47* (2013.01); *G01N 2333/90251* (2013.01); *G01N 2800/50* (2013.01); *G01N 2800/52* (2013.01); *G01N 2800/56* (2013.01)

(58) Field of Classification Search
None
See application file for complete search history.

(56) References Cited

U.S. PATENT DOCUMENTS

2007/0161578 A1* 7/2007 Hwa ............... A61K 31/397
514/23

FOREIGN PATENT DOCUMENTS

WO WO-2015061779 A1 * 4/2015 ......... A61K 48/0041

OTHER PUBLICATIONS

Chugh, A. et al. 2003. Squalene epoxidase as hypocholesterolemic drug target revisited. Progress in Lipid Research 42: 37-50. specif. pp. 38, 39, 40, 42, 43.*
Blom, D.J. et al. 2013. The potential use of monoclonal antibodies and other novel agents as drugs to lower LDL cholesterol. Clinical Lipidology 8(2): 243-256. specif. pp. 243, 244, 246.*
Li, J.Z. et al. 2010. Control of cholesterol biosynthesis, uptake and storage in hepatocytes by Cideb. Biochimica et Biophysica Acta 1801: 577-586. specif. p. 577.*
Choudhary, N.S. et al. 2014. Terbinafine induced liver injury: a case report. Journal of Clinical and Experimental Hepatology 4(3): 264-265. specif. p. 264.*
CDC. 2021. Body measurements. Data for U.S. average U.S. males and females. Datasheet [online]. Retrieved on Feb. 23, 2021. Downloaded from the internet: <https://www.cdc.gov/nchs/fastats/body-measurements.htm> p. 1.*
Khoza, S. et al. 2017. Comparative hepatotoxicity of fluconazole, ketoconazole, itraconazole, terbinafine, and griseofulvin in rats. Journal of Toxicology, pp. 1-9. specif. pp. 2, 4.*
Pro Doc Ltee. 2018. Terbinafine-250. Product monograph. Control No. 212862. pp. 1-36. specif. pp. 24, 25, 26, 27.*
Chaudhary, et al. "Deep Learning based multi-omics integration robustly predicts survival in liver cancer." Clinical Cancer Research (2017): clincanres-0853.
Fabbrini, et al., "Obesity and nonalcoholic fatty liver disease: biochemical, metabolic, and clinical implications." Hepatology 51, No. 2 (2010): 679-689.
Fan, et al. "Epidemiology of non-alcoholic fatty liver disease in China." Journal of hepatology 50, No. 1 (2009): 204-210.
Hardy, et al. "Epigenetics in liver disease: from biology to therapeutics." Gut (2016): gutjnl-2015.
Heimbach, et al. "AASLD guidelines for the treatment of hepatocellular carcinoma." Hepatology 67, No. 1 (2018): 358-380.
Ioannou, "The role of cholesterol in the pathogenesis of NASH." Trends in Endocrinology & Metabolism 27, No. 2 (2016): 84-95.
Kudo, "Systemic Therapy for Hepatocellular Carcinoma: 2017 Update." Oncology 93, No. Suppl. 1 (2017): 135-146.
Lazo, et al., "Prevalence of nonalcoholic fatty liver disease in the United States: the Third National Health and Nutrition Examination Survey, 1988-1994." American journal of epidemiology 178, No. 1 (2013): 38-45.
Llovet, et al. "Sorafenib in advanced hepatocellular carcinoma." New England journal of medicine 359, No. 4 (2008): 378-390.
Michelotti, et al. "NAFLD, NASH and liver cancer." Nature Reviews Gastroenterology and Hepatology 10, No. 11 (2013): 656.
Mittal, et al. "Epidemiology of HCC: consider the population." Journal of clinical gastroenterology 47 (2013): S2.
Perry, et al, "The role of hepatic lipids in hepatic insulin resistance and type 2 diabetes." Nature 510, No. 7503 (2014): 84.
Rinella, et al. "NAFLD in 2014: genetics, diagnostics and therapeutic advances in NAFLD." Nature Reviews Gastroenterology and Hepatology 12, No. 2 (2015): 65.
Schuppan, et al. "Non-alcoholic steatohepatitis: pathogenesis and novel therapeutic approaches." Journal of gastroenterology and hepatology 28, No. S1 (2013): 68-76.

(Continued)

*Primary Examiner* — Olivia M. Wise
*Assistant Examiner* — Sharon M. Papciak
(74) *Attorney, Agent, or Firm* — Kilpatrick Townsend & Stockton LLP

(57) ABSTRACT

The present invention provides a method for providing a diagnosis or prognosis of a non-alcoholic fatty liver disease (NAFLD) in a subject by detecting expression level of the Squalene Epoxidase (SQLE) gene. A kit and device useful for such methods are also provided. In addition, the present invention provides a method for treating NAFLD by suppressing SQLE gene expression or activity.

6 Claims, 31 Drawing Sheets
(30 of 31 Drawing Sheet(s) Filed in Color)
Specification includes a Sequence Listing.

(56) References Cited

OTHER PUBLICATIONS

Targher, et al. "Obesity: Metabolically healthy obesity and NAFLD." Nature Reviews Gastroenterology and Hepatology 13, No. 8 (2016): 442.

Williams, et al, "Prevalence of nonalcoholic fatty liver disease and nonalcoholic steatohepatitis among a largely middle-aged population utilizing ultrasound and liver biopsy: a prospective study." Gastroenterology 140, No. 1 (2011): 124-131.

Wong, et al., "Prevalence of non-alcoholic fatty liver disease and advanced fibrosis in Hong Kong Chinese: a population study using proton-magnetic resonance spectroscopy and transient elastography." Gut (2011): gutjnl-2011.

Yu, "A concise review of updated guidelines regarding the management of hepatocellular carcinoma around the world: 2010-2016." Clinical and molecular hepatology 22, No. 1 (2016): 7.

Yu, et al, "Obesity, insulin resistance, NASH and hepatocellular carcinoma." In Seminars in cancer biology, vol. 23, No. 6, pp. 483-491. Academic Press, 2013.

\* cited by examiner

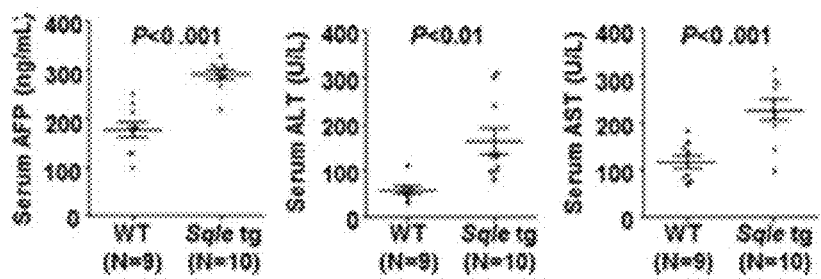
Figure 10D
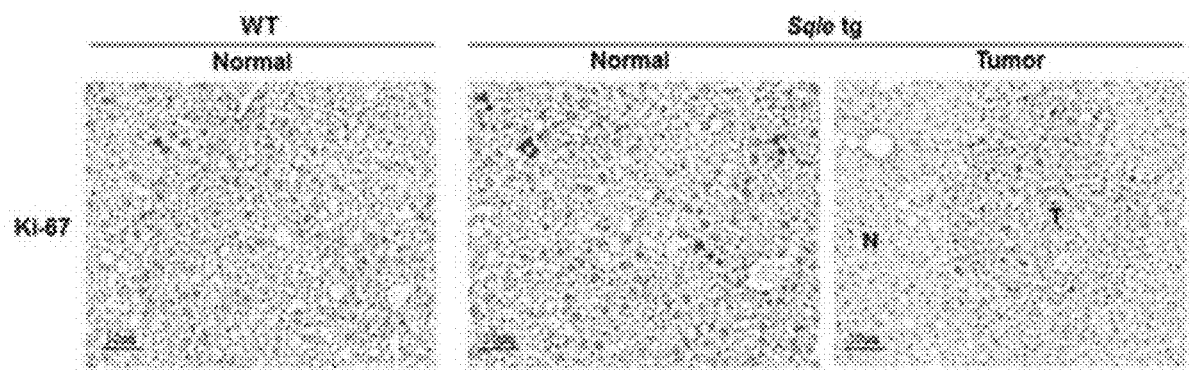
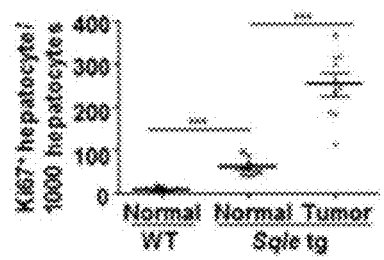
Figure 10E

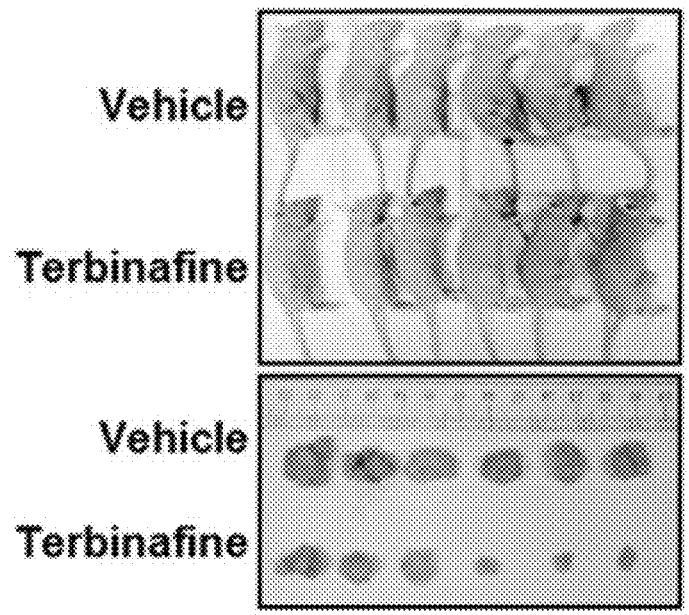
Figure 12A1
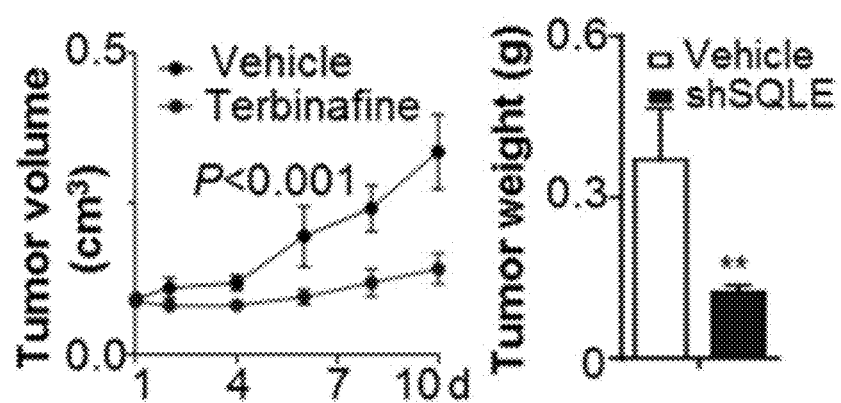
Figure 12A2

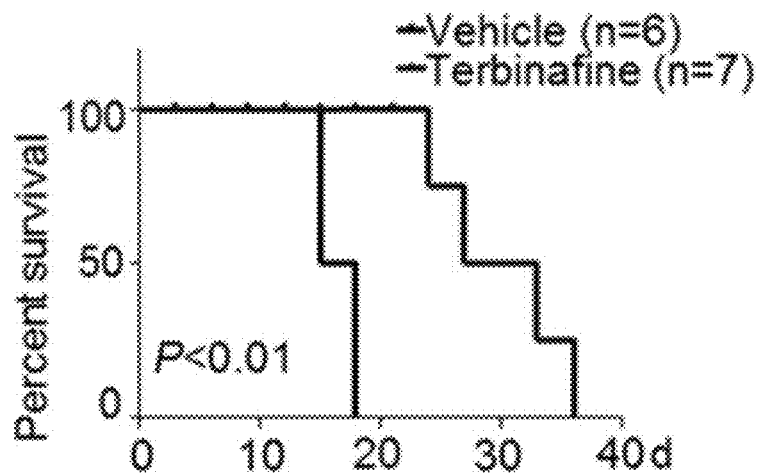
Figure 12A3
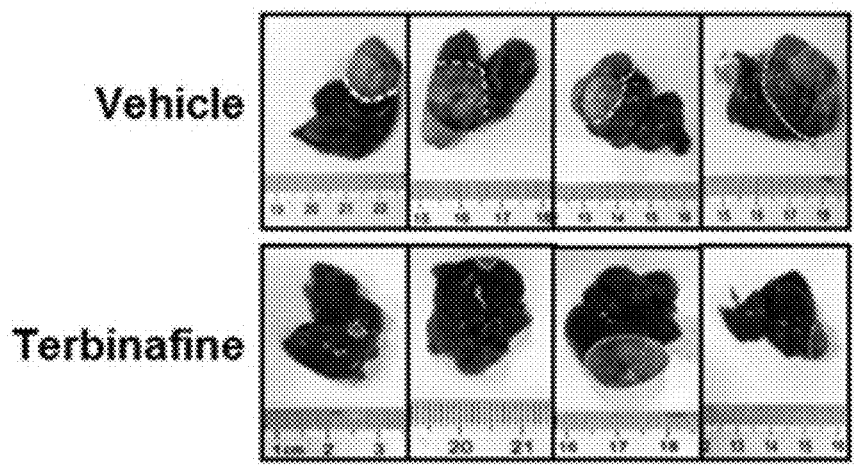
Figure 12B1

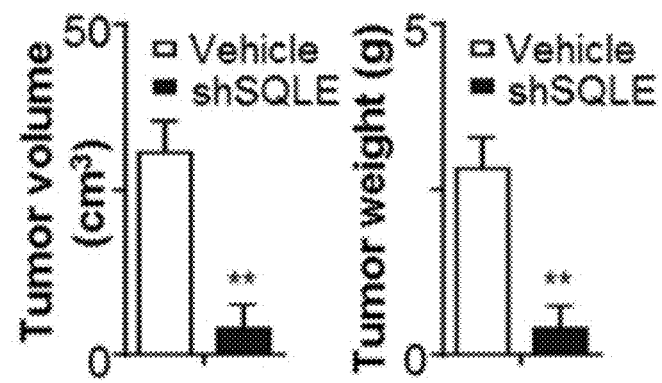
Figure 12B2
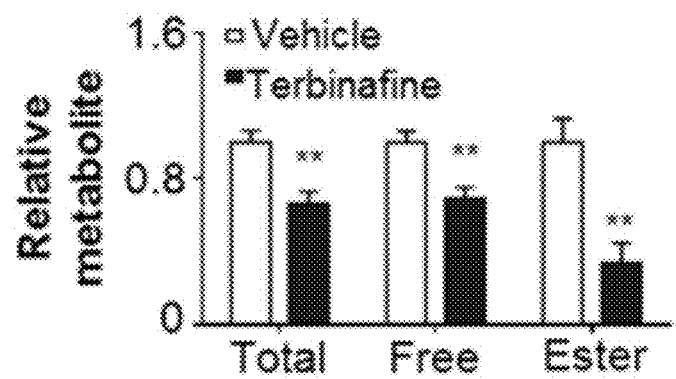
Figure 12C1
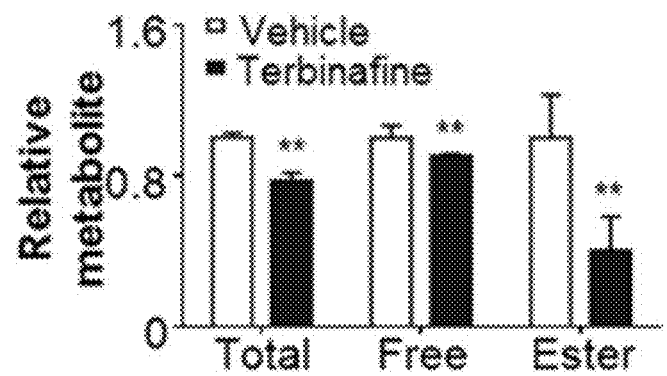
Figure 12C1

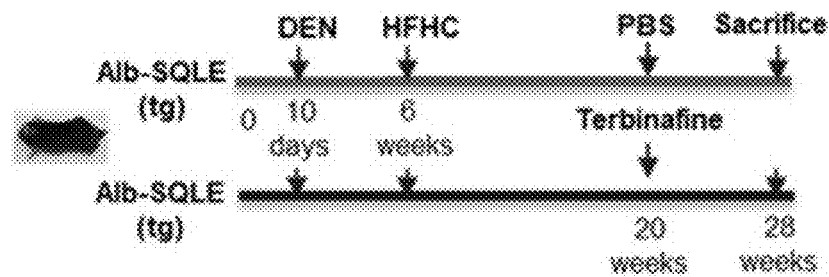
Figure 13A
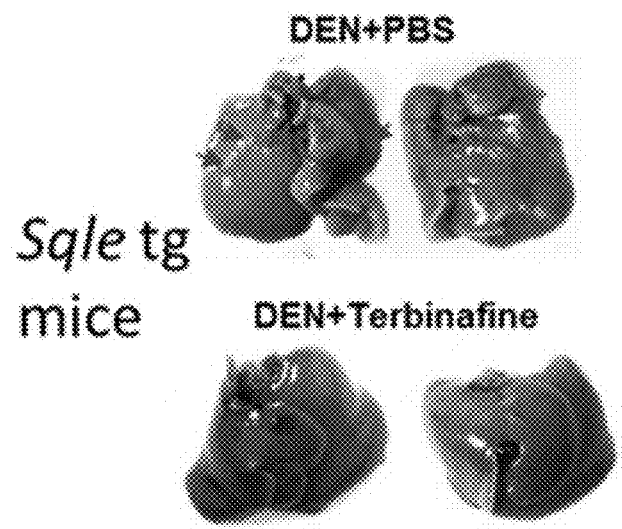
Figure 13B1

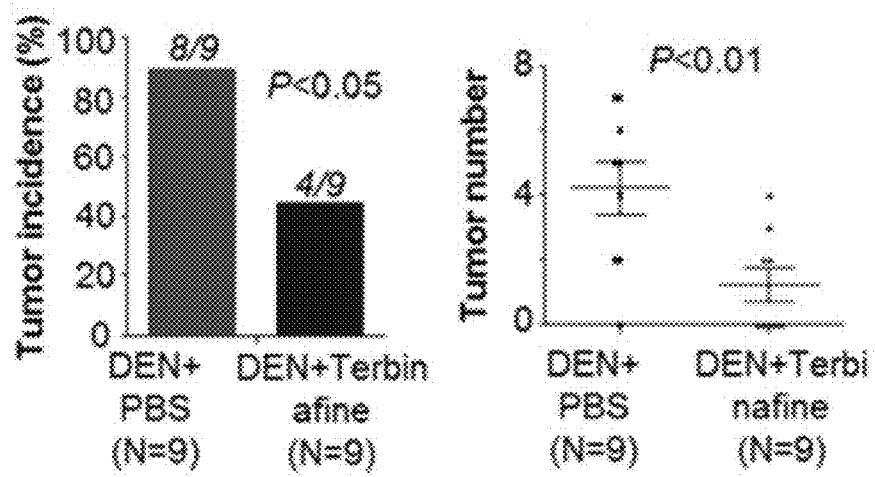
Figure 13B2
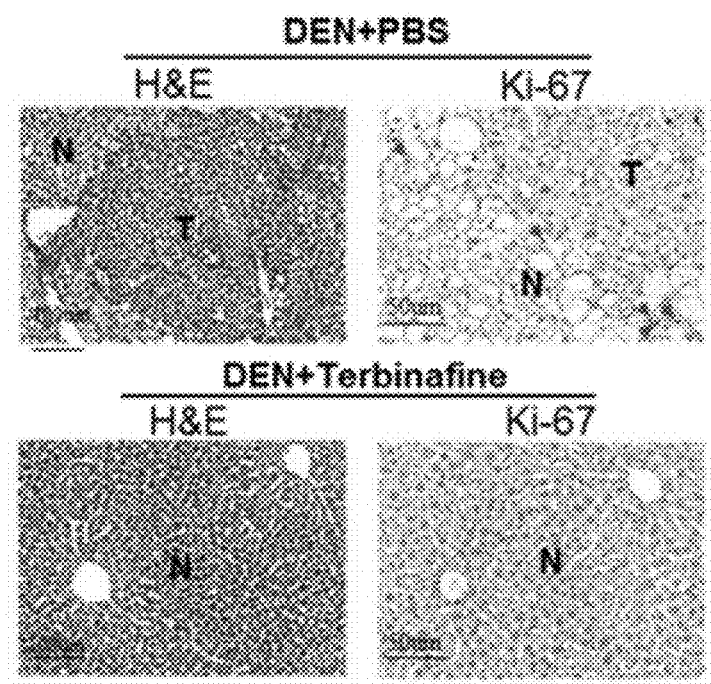
Figure 13C

SEQUENCE LISTING

<160> NUMBER OF SEQ ID NOS: 44

<210> SEQ ID NO 1
<211> LENGTH: 2989
<212> TYPE: DNA
<213> ORGANISM: Homo sapiens

<400> SEQUENCE: 1

```
gtctgggccg agcccgccca gctggctgag acgcgtggag cctggcggcg agtggggcg      60 tgcgacggtt actctggtta ctggggccgc gccgcgctgg cgagagccgc cgcccgcgag     120
ggatgctggt gaggaagccg tcgggagccg ccgccgccat ctgagggagg taccctggaa     180
accacctttt atcggtgggg aagtgcagtc gcggtgggcg gctctggggg ccagcgaaac     240
gggaggcctc taaatcttta ggttgggggct gcattgccct ggagccgcac tcttgagtcc     300
gaggccatct tttgttggag aaggcgtcgg cgttggcgtt ttcccgaggt tgggctgtac     360
agtgtctccg tccgcggaaa aagaagcctc tgaaccccgcg ccggcccgca gccccgtgc      420 cttccggccg ctgctcgccg tcgccagagg ctaggccacg tttcccccag tgccgaggtg     480
tttctgtgac cctccctcca ctcccattcc cttctgaaag ggcacctgct cttggtgaga     540
aaagaaatta tagcacgaag agccagtatc agaagagtat ccatcacccg cagcaaccgc     600
tcagggaaca ccatcaaaaa agaaaaaaag ggaatatctg gatttcctgg gcgaggagga     660
gcgagtctgc tcgggagctg ttccagcagg cgattttttaa atactgcttt ctacgcccta    720
```

```
tacaacttgg cttcacatac ttttacacta actttatatg attttttaaaa actggtctga      780 tcggacttct cgtcctggga cactgtttac tggagtctgg ccggctctcc gtgctcctct      840
tggtacctca ttttggggag aaccttaaac ccactcgagc agataatctc cgccttgacc      900
ggtgccacca aagaagcctt ggaaccatgt ggacttttct gggcattgcc actttcacct      960 attttttataa gaagttcggg gacttcatca ctttggccaa cagggaggtc ctgttgtgcg     1020
tgctggtgtt cctctcgctg ggcctggtgc tctcctaccg ctgtcgccac cgaaacgggg     1080
gtctcctcgg gcgccagcag agcggctccc agttcgccct cttctcggat attctctcag     1140
gcctgccttt cattggcttc ttctgggcca atcccccccc tgaatcagaa ataaggagc      1200 agctcgaggc caggaggcgc agaaaaggaa ccaatatttc agaaacaagc ttaataggaa     1260
cagctgcctg tacatcaaca tcttctcaga atgacccaga agttatcatc gtgggagctg     1320
gcgtgcttgg ctctgctttg gcagctgtgc tttccagaga tggaagaaag gtgacagtca     1380
ttgagagaga cttaaaagag cctgacagaa tagttggaga attcctgcag ccgggtggtt     1440
atcatgttct caaagacctt ggtcttggag atacagtgga aggtcttgat gcccaggttg     1500
taaatggtta catgattcat gatcaggaaa gcaaatcaga ggttcagatt ccttaccctc     1560
tgtcagaaaa caatcaagtg cagagtggaa gagctttcca tcacggaaga ttcatcatga     1620
gtctccggaa agcagctatg gcagagccca atgcaaagtt tattgaaggt gttgtgttac     1680
agttattaga ggaagatgat gttgtgatgg gagttcagta caaggataaa gagactggag     1740
atatcaagga actccatgct ccactgactg ttgttgcaga tgggctttc tccaagttca     1800 ggaaaagcct ggtctccaat aaagtttctg tatcatctca ttttgttggc tttcttatga     1860
agaatgcacc acagttttaaa gcaaatcatg ctgaacttat tttagctaac ccgagtccag     1920
ttctcatcta ccagatttca tccagtgaaa ctcgagtact tgttgacatt agaggagaaa     1980
tgccaaggaa tttaagagaa tacatggttg aaaaaattta cccacaaata cctgatcacc     2040
tgaaagaacc attcttagaa gccactgaca attctcatct gaggtccatg ccagcaagct     2100
tccttcctcc ttcatcagtg aagaaacgag gtgttcttct tttgggagac gcatataata     2160
tgaggcatcc acttactggt ggaggaatga ctgttgcttt taaagatata aaactatgga     2220
gaaaactgct aaagggtatc cctgaccttt atgatgatgc agctattttc gaggccaaaa     2280 aatcattttta ctgggcaaga aaaacatctc attcctttgt cgtgaatatc cttgctcagg     2340
ctctttatga attattttct gccacagatg attccctgca tcaactaaga aaagcctgtt     2400
ttctttattt caaacttggt ggcgaatgtg ttgcgggtcc tgttgggctg ctttctgtat     2460
tgtctcctaa ccctctagtt ttaattggac acttctttgc tgttgcaatc tatgccgtgt     2520 attttttgctt taagtcagaa ccttggatta caaaacctcg agcccttctc agtagtggtg     2580
ctgtattgta caaagcgtgt tctgtaatat ttcctctaat ttactcagaa atgaagtata     2640
tggttcatta agcttaaagg ggaaccattt gtgaatgaat atttggaact taccaagtcc     2700
taagagactt ttgaagagg atatatatag catagtacca taccacttat aaagtggaaa     2760
ctcttggacc aagatttgga ttaatttgtt tttgaagttt tttgtatata aatatgtaaa     2820
tacatgcttt aatttgcaat ttaaaatgaa ggggttaaat aagttagaca tttaaaagaa     2880
atgattgtta ccataaaatta gtgctaatgc tgaggagaac tacagttttt cttttgaatt      2940
tagtatttga gatgagttgt tgggacatgc aaataaaatg aagaatgaa              2989
```

<210> SEQ ID NO 2
<211> LENGTH: 1722

```
<212> TYPE: DNA
<213> ORGANISM: Homo sapiens

<400> SEQUENCE: 2
atgtggactt ttctgggcat tgccactttc acctattttt ataagaagtt cggggacttc      60
atcactttgg ccaacaggga ggtcctgttg tgcgtgctgg tgttcctctc gctgggcctg     120
gtgctctcct accgctgtcg ccaccgaaac gggggtctcc tcgggcgcca gcagagcggc     180
tcccagttcg ccctcttctc ggatattctc tcaggcctgc cttttcattgg cttcttctgg    240
gccaaatccc ccctgaatc agaaaataag gagcagctcg aggccaggag gcgcagaaaa      300
ggaaccaata tttcagaaac aagcttaata ggaacagctg cctgtacatc aacatcttct     360
cagaatgacc cagaagttat catcgtggga gctggcgtgc ttggctctgc tttggcagct     420
gtgctttcca gagatggaag aaaggtgaca gtcattgaga gagacttaaa agagcctgac     480
agaatagttg gagaattcct gcagccgggt ggttatcatg ttctcaaaga ccttggtctt     540
ggagatacag tggaaggtct tgatgcccag gttgtaaatg gttacatgat tcatgatcag     600
gaaagcaaat cagaggttca gattccttac cctctgtcag aaaacaatca agtgcagagt     660
ggaagagctt ccatcacgg aagattcatc atgagtctcc ggaaagcagc tatggcagag     720
cccaatgcaa gtttattga aggtgttgtg ttacagttat tagaggaaga tgatgttgtg     780
atgggagttc agtacaagga taaagagact ggagatatca aggaactcca tgctccactg    840
actgttgttg cagatgggct tttctccaag ttcaggaaaa gcctggtctc caataaagtt    900
tctgtatcat ctcattttgt tggctttctt atgaagaatg caccacagtt taaagcaaat   960
catgctgaac ttattttagc taacccgagt ccagttctca tctaccagat ttcatccagt    1020
gaaactcgag tacttgttga cattagagga gaaatgccaa ggaatttaag agaatacatg   1080
gttgaaaaaa tttacccaca aatacctgat cacctgaaag aaccattctt agaagccact   1140
gacaattctc atctgaggtc catgccagca agcttcctcc ctccttcatc agtgaagaaa   1200
cgaggtgttc ttcttttggg agacgcatat aatatgaggc atccacttac tggtggagga   1260
atgactgttg ctttttaaaga tataaaacta tggagaaaac tgctaaaggg tatccctgac   1320
ctttatgatg atgcagctat tttcgaggcc aaaaaatcat tttactgggc aagaaaaaca   1380
tctcattcct ttgtcgtgaa tatccttgct caggctcttt atgaattatt ttctgccaca   1440
gatgattccc tgcatcaact aagaaaagcc tgttttcttt atttcaaact tggtggcgaa   1500
tgtgttgcgg gtcctgttgg gctgcttttct gtattgtctc ctaaccctct agttttaatt   1560
ggacacttct ttgctgttgc aatctatgcc gtgtattttt gctttaagtc agaaccttgg   1620
attacaaaac ctcgagccct tctcagtagt ggtgctgtat tgtacaaagc gtgttctgta   1680
atatttcctc taatttactc agaaatgaag tatatggttc at                       1722

<210> SEQ ID NO 3
<211> LENGTH: 574
<212> TYPE: PRT
<213> ORGANISM: Homo sapiens

<400> SEQUENCE: 3

Met Trp Thr Phe Leu Gly Ile Ala Thr Phe Thr Tyr Phe Tyr Lys Lys
1               5                   10                  15

Phe Gly Asp Phe Ile Thr Leu Ala Asn Arg Glu Val Leu Leu Cys Val
                20                  25                  30

Leu Val Phe Leu Ser Leu Gly Leu Val Leu Ser Tyr Arg Cys Arg His
            35                  40                  45
```

```
Arg Asn Gly Gly Leu Leu Gly Arg Gln Gln Ser Gly Ser Gln Phe Ala
    50                  55                  60

Leu Phe Ser Asp Ile Leu Ser Gly Leu Pro Phe Ile Gly Phe Phe Trp
65                  70                  75                  80

Ala Lys Ser Pro Pro Glu Ser Glu Asn Lys Glu Gln Leu Glu Ala Arg
                85                  90                  95

Arg Arg Arg Lys Gly Thr Asn Ile Ser Glu Thr Ser Leu Ile Gly Thr
            100                 105                 110

Ala Ala Cys Thr Ser Thr Ser Ser Gln Asn Asp Pro Glu Val Ile Ile
        115                 120                 125

Val Gly Ala Gly Val Leu Gly Ser Ala Leu Ala Ala Val Leu Ser Arg
    130                 135                 140

Asp Gly Arg Lys Val Thr Val Ile Glu Arg Asp Leu Lys Glu Pro Asp
145                 150                 155                 160

Arg Ile Val Gly Glu Phe Leu Gln Pro Gly Gly Tyr His Val Leu Lys
                165                 170                 175

Asp Leu Gly Leu Gly Asp Thr Val Glu Gly Leu Asp Ala Gln Val Val
            180                 185                 190

Asn Gly Tyr Met Ile His Asp Gln Glu Ser Lys Ser Gly Val Gln Ile
        195                 200                 205

Pro Tyr Pro Leu Ser Glu Asn Asn Gln Val Gln Ser Gly Arg Ala Phe
210                 215                 220

His His Gly Arg Phe Ile Met Ser Leu Arg Lys Ala Ala Met Ala Glu
225                 230                 235                 240

Pro Asn Ala Lys Phe Ile Glu Gly Val Val Leu Gln Leu Leu Glu Glu
                245                 250                 255

Asp Asp Val Val Met Gly Val Gln Tyr Lys Asp Lys Glu Thr Gly Asp
            260                 265                 270

Ile Lys Glu Leu His Ala Pro Leu Thr Val Val Ala Asp Gly Leu Phe
        275                 280                 285

Ser Lys Phe Arg Lys Ser Leu Val Ser Asn Lys Val Ser Val Ser Ser
    290                 295                 300

His Phe Val Gly Phe Leu Met Lys Asn Ala Pro Gln Phe Lys Ala Asn
305                 310                 315                 320

His Ala Glu Leu Ile Leu Ala Asn Pro Ser Pro Val Leu Ile Tyr Gln
                325                 330                 335

Ile Ser Ser Ser Glu Thr Arg Val Leu Val Asp Ile Arg Gly Glu Met
            340                 345                 350

Pro Arg Asn Leu Arg Glu Tyr Met Val Glu Lys Ile Tyr Pro Gln Ile
        355                 360                 365

Pro Asp His Leu Lys Glu Pro Phe Leu Glu Ala Thr Asp Asn Ser His
    370                 375                 380

Leu Arg Ser Met Pro Ala Ser Phe Leu Pro Pro Ser Ser Val Lys Lys
385                 390                 395                 400

Arg Gly Val Leu Leu Leu Gly Asp Ala Tyr Asn Met Arg His Pro Leu
                405                 410                 415

Thr Gly Gly Gly Met Thr Val Ala Phe Lys Asp Ile Lys Leu Trp Arg
            420                 425                 430

Lys Leu Leu Lys Gly Ile Pro Asp Leu Tyr Asp Asp Ala Ala Ile Phe
        435                 440                 445

Glu Ala Lys Lys Ser Phe Tyr Trp Ala Arg Lys Thr Ser His Ser Phe
    450                 455                 460
```

```
Val Val Asn Ile Leu Ala Gln Ala Leu Tyr Glu Leu Phe Ser Ala Thr
465                 470                 475                 480

Asp Asp Ser Leu His Gln Leu Arg Lys Ala Cys Phe Leu Tyr Phe Lys
                485                 490                 495

Leu Gly Gly Glu Cys Val Ala Gly Pro Val Gly Leu Leu Ser Val Leu
            500                 505                 510

Ser Pro Asn Pro Leu Val Leu Ile Gly His Phe Phe Ala Val Ala Ile
        515                 520                 525

Tyr Ala Val Tyr Phe Cys Phe Lys Ser Glu Pro Trp Ile Thr Lys Pro
    530                 535                 540

Arg Ala Leu Leu Ser Ser Gly Ala Val Leu Tyr Lys Ala Cys Ser Val
545                 550                 555                 560

Ile Phe Pro Leu Ile Tyr Ser Glu Met Lys Tyr Met Val His
                565                 570
```

<210> SEQ ID NO 4
<211> LENGTH: 199
<212> TYPE: DNA
<213> ORGANISM: Artificial Sequence
<220> FEATURE:
<223> OTHER INFORMATION: synthetic partial coding sequence used to
      detect human SQLE by real-time PCR

<400> SEQUENCE: 4
attcccttct gaaagggcac ctgctcttgg tgagaaaaga aattatagca cgaagagcca      60
gtatcagaag agtatccatc acccgcagca accgctcagg gaacaccatc aaaaaagaaa     120
aaaagggaat atctggattt cctgggcgag gaggagcgag tctgctcggg agctgttcca     180
gcaggcgatt tttaaatac                                                  199

<210> SEQ ID NO 5
<211> LENGTH: 22
<212> TYPE: DNA
<213> ORGANISM: Artificial Sequence
<220> FEATURE:
<223> OTHER INFORMATION: synthetic primer

<400> SEQUENCE: 5
attcccttct gaaagggcac ct                                               22

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
ttatttaaaa atcgcctgct gga                                              23

<210> SEQ ID NO 7
<211> LENGTH: 25
<212> TYPE: DNA
<213> ORGANISM: Artificial Sequence
<220> FEATURE:
<223> OTHER INFORMATION: synthetic primer

<400> SEQUENCE: 7
catccacgaa actaccttca actcc                                            25

<210> SEQ ID NO 8
<211> LENGTH: 18

<212> TYPE: DNA
<213> ORGANISM: Artificial Sequence
<220> FEATURE:
<223> OTHER INFORMATION: synthetic primer

<400> SEQUENCE: 8
gagccgccga tccacacg                                                 18

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
ggagccatgg attgcacatt                                               20

<210> SEQ ID NO 10
<211> LENGTH: 18
<212> TYPE: DNA
<213> ORGANISM: Artificial Sequence
<220> FEATURE:
<223> OTHER INFORMATION: synthetic primer

<400> SEQUENCE: 10
ggcccgggaa gtcactgt                                                 18

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
ggaggtggtg atagccggta t                                             21

<210> SEQ ID NO 12
<211> LENGTH: 21
<212> TYPE: DNA
<213> ORGANISM: Artificial Sequence
<220> FEATURE:
<223> OTHER INFORMATION: synthetic primer

<400> SEQUENCE: 12
tgggtaatcc atagagccca g                                             21

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
ccggagaccc ttagatcga                                                19

<210> SEQ ID NO 14
<211> LENGTH: 26
<212> TYPE: DNA
<213> ORGANISM: Artificial Sequence
<220> FEATURE:
<223> OTHER INFORMATION: synthetic primer

<400> SEQUENCE: 14

```
tagcctgtaa aagatttctg caaacc                                        26

<210> SEQ ID NO 15
<211> LENGTH: 22
<212> TYPE: DNA
<213> ORGANISM: Artificial Sequence
<220> FEATURE:
<223> OTHER INFORMATION: synthetic primer

<400> SEQUENCE: 15
aatgaacgtg caatccgatt tg                                            22

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
tttgccacgt catctgggtt t                                             21

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
atgggctgtg atcggaactg                                               20

<210> SEQ ID NO 18
<211> LENGTH: 18
<212> TYPE: DNA
<213> ORGANISM: Artificial Sequence
<220> FEATURE:
<223> OTHER INFORMATION: synthetic primer

<400> SEQUENCE: 18
gagccgccga tccacacg                                                 18

<210> SEQ ID NO 19
<211> LENGTH: 19
<212> TYPE: DNA
<213> ORGANISM: Artificial Sequence
<220> FEATURE:
<223> OTHER INFORMATION: synthetic primer

<400> SEQUENCE: 19
cccggcacaa tatcctcgg                                                19

<210> SEQ ID NO 20
<211> LENGTH: 21
<212> TYPE: DNA
<213> ORGANISM: Artificial Sequence
<220> FEATURE:
<223> OTHER INFORMATION: synthetic primer

<400> SEQUENCE: 20
tctggtgttg tagtggaccg t                                             21

<210> SEQ ID NO 21
<211> LENGTH: 22
<212> TYPE: DNA
<213> ORGANISM: Artificial Sequence
```

<220> FEATURE:
<223> OTHER INFORMATION: synthetic primer

<400> SEQUENCE: 21
atctcaccat tcggatgagt ct                                    22

<210> SEQ ID NO 22
<211> LENGTH: 22
<212> TYPE: DNA
<213> ORGANISM: Artificial Sequence
<220> FEATURE:
<223> OTHER INFORMATION: synthetic primer

<400> SEQUENCE: 22
tgtagggacg attggagtga aa                                    22

<210> SEQ ID NO 23
<211> LENGTH: 19
<212> TYPE: DNA
<213> ORGANISM: Artificial Sequence
<220> FEATURE:
<223> OTHER INFORMATION: synthetic primer

<400> SEQUENCE: 23
ctcccgtggc ttctagtgc                                        19

<210> SEQ ID NO 24
<211> LENGTH: 22
<212> TYPE: DNA
<213> ORGANISM: Artificial Sequence
<220> FEATURE:
<223> OTHER INFORMATION: synthetic primer

<400> SEQUENCE: 24
gccttagttt ggacaggatc tg                                    22

<210> SEQ ID NO 25
<211> LENGTH: 22
<212> TYPE: DNA
<213> ORGANISM: Artificial Sequence
<220> FEATURE:
<223> OTHER INFORMATION: synthetic primer

<400> SEQUENCE: 25
cttctgtcta ctgaacttcg gg                                    22

<210> SEQ ID NO 26
<211> LENGTH: 22
<212> TYPE: DNA
<213> ORGANISM: Artificial Sequence
<220> FEATURE:
<223> OTHER INFORMATION: synthetic primer

<400> SEQUENCE: 26
caggcttgtc actcgaattt tg                                    22

<210> SEQ ID NO 27
<211> LENGTH: 23
<212> TYPE: DNA
<213> ORGANISM: Artificial Sequence
<220> FEATURE:
<223> OTHER INFORMATION: synthetic primer

<400> SEQUENCE: 27
gtcctcagaa gctaaccatc tcc                                   23

<210> SEQ ID NO 28
<211> LENGTH: 22
<212> TYPE: DNA
<213> ORGANISM: Artificial Sequence
<220> FEATURE:
<223> OTHER INFORMATION: synthetic primer

<400> SEQUENCE: 28
ccagagccta tgactccatg tc                                              22

<210> SEQ ID NO 29
<211> LENGTH: 23
<212> TYPE: DNA
<213> ORGANISM: Artificial Sequence
<220> FEATURE:
<223> OTHER INFORMATION: synthetic primer

<400> SEQUENCE: 29
atttccacac ttctatgcct cct                                             23

<210> SEQ ID NO 30
<211> LENGTH: 23
<212> TYPE: DNA
<213> ORGANISM: Artificial Sequence
<220> FEATURE:
<223> OTHER INFORMATION: synthetic primer

<400> SEQUENCE: 30
atccagtatg gtcctgaaga tca                                             23

<210> SEQ ID NO 31
<211> LENGTH: 22
<212> TYPE: DNA
<213> ORGANISM: Artificial Sequence
<220> FEATURE:
<223> OTHER INFORMATION: synthetic primer

<400> SEQUENCE: 31
actgttgcct ctcgtacata ca                                              22

<210> SEQ ID NO 32
<211> LENGTH: 21
<212> TYPE: DNA
<213> ORGANISM: Artificial Sequence
<220> FEATURE:
<223> OTHER INFORMATION: synthetic primer

<400> SEQUENCE: 32
gaggaggttc acagcccttt t                                               21

<210> SEQ ID NO 33
<211> LENGTH: 21
<212> TYPE: DNA
<213> ORGANISM: Artificial Sequence
<220> FEATURE:
<223> OTHER INFORMATION: synthetic primer

<400> SEQUENCE: 33
ggagttcgag gaaccctagt g                                               21

<210> SEQ ID NO 34
<211> LENGTH: 21
<212> TYPE: DNA
<213> ORGANISM: Artificial Sequence
<220> FEATURE:
<223> OTHER INFORMATION: synthetic primer

<400> SEQUENCE: 34
gggatttgta gtggatcgtg c                                              21

<210> SEQ ID NO 35
<211> LENGTH: 21
<212> TYPE: DNA
<213> ORGANISM: Artificial Sequence
<220> FEATURE:
<223> OTHER INFORMATION: synthetic primer

<400> SEQUENCE: 35
accacaatac ctacatgcac c                                              21

<210> SEQ ID NO 36
<211> LENGTH: 21
<212> TYPE: DNA
<213> ORGANISM: Artificial Sequence
<220> FEATURE:
<223> OTHER INFORMATION: synthetic primer

<400> SEQUENCE: 36
aagcaggcga ggaaaagata g                                              21

<210> SEQ ID NO 37
<211> LENGTH: 19
<212> TYPE: DNA
<213> ORGANISM: Artificial Sequence
<220> FEATURE:
<223> OTHER INFORMATION: synthetic primer

<400> SEQUENCE: 37
gctcctctta ggggccact                                                 19

<210> SEQ ID NO 38
<211> LENGTH: 19
<212> TYPE: DNA
<213> ORGANISM: Artificial Sequence
<220> FEATURE:
<223> OTHER INFORMATION: synthetic primer

<400> SEQUENCE: 38
ccacgtctca ccattgggg                                                 19

<210> SEQ ID NO 39
<211> LENGTH: 21
<212> TYPE: DNA
<213> ORGANISM: Artificial Sequence
<220> FEATURE:
<223> OTHER INFORMATION: synthetic primer

<400> SEQUENCE: 39
gtaacttcgt gcctagcaac a                                              21

<210> SEQ ID NO 40
<211> LENGTH: 23
<212> TYPE: DNA
<213> ORGANISM: Artificial Sequence
<220> FEATURE:
<223> OTHER INFORMATION: synthetic primer

<400> SEQUENCE: 40
cctttgtcag aatactgagc agc                                            23

<210> SEQ ID NO 41

```
<211> LENGTH: 23
<212> TYPE: DNA
<213> ORGANISM: Artificial Sequence
<220> FEATURE:
<223> OTHER INFORMATION: synthetic primer

<400> SEQUENCE: 41
ctgtaacatg gaaactgggg aaa                                              23

<210> SEQ ID NO 42
<211> LENGTH: 23
<212> TYPE: DNA
<213> ORGANISM: Artificial Sequence
<220> FEATURE:
<223> OTHER INFORMATION: synthetic primer

<400> SEQUENCE: 42
ccatagctga actgaaaacc acc                                              23

<210> SEQ ID NO 43
<211> LENGTH: 20
<212> TYPE: DNA
<213> ORGANISM: Artificial Sequence
<220> FEATURE:
<223> OTHER INFORMATION: synthetic primer

<400> SEQUENCE: 43
aaggtcatcc cagagctgaa                                                  20

<210> SEQ ID NO 44
<211> LENGTH: 20
<212> TYPE: DNA
<213> ORGANISM: Artificial Sequence
<220> FEATURE:
<223> OTHER INFORMATION: synthetic primer

<400> SEQUENCE: 44
ctgcttcacc accttcttga                                                  20
```

SQUALENE EPOXIDASE IN THE DIAGNOSIS AND TREATMENT OF NON-ALCOHOLIC FATTY LIVER DISEASES

REFERENCE TO SUBMISSION OF A SEQUENCE LISTING AS A TEXT FILE

The Sequence Listing written in file SEQ 080015-1078898-024300US.txt created on Jun. 1, 2018, 19,618 bytes, machine format IBM-PC, MS-Windows operating system, is hereby incorporated by reference in its entirety for all purposes.

BACKGROUND OF THE INVENTION

Non-alcoholic fatty liver disease (NAFLD) is a heterogeneous condition defined by ectopic fat deposition in the liver that is not caused by alcohol consumption [1, 2]. Obesity, diabetes and the metabolic syndrome are the major risk factors for the development of NAFLD [3]. It has been reported that ~70% of type II diabetes patients have NAFLD and up to 98% of obese individuals suffer from NAFLD [4-6]. In light of the obesity epidemic in the developed world, NAFLD is currently the most common form of liver disease in the West and Asia. According to the latest statistics [1, 7, 8], the incidence of NAFLD is 27% in Hong Kong, 12.5-35.4% in the mainland and it is even more prevalent in the USA (>30%). Hence, NAFLD is a major health problem worldwide.

Pathologically, NAFLD comprises of a spectrum of liver conditions ranging from relatively benign, simple steatosis to more aggressive conditions such as nonalcoholic steatohepatitis (NASH) [3, 9, 10]. NAFLD is characterized by increased hepatic accumulation of triglyceride and cholesterol, and the latter is a major lipotoxic molecule triggering the development of NASH [11, 12]. In general, approximately 15-25% of NAFLD patients will progress to NASH, which might further progress to liver fibrosis, cirrhosis, and hepatocellular carcinoma (HCC) [13]. Despite a huge disease burden, no pharmacological treatment has been approved for NAFLD. The discovery of novel therapeutic targets and development of treatment modalities for NAFLD is an unmet clinical need.

Hepatocellular carcinoma (HCC) is a major health issue with an increasing rate of incidence and more than 700,000 new cases diagnosed globally each year [14]. According to the latest statistics from the Hong Kong Cancer Registry, HCC is ranked as the fourth most common cancer and the third cause of cancer death in Hong Kong. In the US, more than 40,000 people will be diagnosed with liver cancers in 2017 and approximately 28,920 will die from these diseases [15]. HCC is a heterogeneous disease with multi-risk factors and very poor prognosis.

Several HCC staging guidelines suggested symptomatic treatment to different HCC patients, such as molecularly target therapies [16, 17]. Sorafenib, a multi-kinase inhibitor, is the first and only targeted therapy approved for advanced HCC, but drug resistance limited its effectiveness in the clinic [18, 19]. Thus, there exists an urgent need to develop new and effective means for treating NAFLD including NAFLD-HCC. The present invention fulfills this and other related needs.

BRIEF SUMMARY OF THE INVENTION

The present inventors have identified the important role Squalene Epoxidase (SQLE) in the liver pathologies generally referred to as non-alcoholic fatty liver diseases (NAFLD), making it a diagnostic/prognostic marker for NAFLD, especially NAFLD-caused hepatocellular carcinoma (NAFLD-HCC), as well as a therapeutic target for these conditions. More specifically, the inventors show that a higher level of SQLE expression (as mRNA or protein) is present in NAFLD, which is at least in part due to amplification of the genomic SQLE gene number. Further, a higher SQLE expression level in an NAFLD-HCC patient indicates an increased risk of mortality from the disease or a lower likelihood of survival in comparison to another patient who has a lower level of SQLE expression. In addition, the compound terbinafine, previously used as a fungicide, has been identified for the first time as an effective agent for treating HCC, especially NAFLD-HCC, due to its role as an inhibitor of SQLE.

As such, in the first aspect, the present invention provides a method for detecting the presence of NAFLD or assessing the risk for developing NAFLD (especially NAFLD-HCC) in a subject. The method includes the steps of: (a) measuring the level of SQLE in a sample taken from the subject, and (b) comparing the level obtained in step (a) with a standard control. When an increase in the SQLE level is detected as compared with the standard control, it indicates that the subject may have NAFLD (especially NAFLD-HCC) or have an increased risk for NAFLD (especially NAFLD-HCC). Typically, the sample used in the method is a liver tissue sample or a blood sample such as a serum or plasma sample. The subject being tested may be a human or a member of other mammals such as primates, who may or may not exhibit any signs indicative of any condition or abnormality relating to the liver.

In some embodiments, the level of SQLE is the SQLE protein level. In other embodiments, the level of SQLE is SQLE mRNA level or genomic SQLE gene copy number. When the SQLE protein level is measured, step (a) may include an immunoassay using an antibody that specifically binds the SQLE protein. For example, a Western Blot analysis may be used. In other cases, step (a) may involve mass spectrometry, or a hybridization-based assay such as hybridization to a microarray, fluorescence probe, or molecular beacon.

When SQLE genomic DNA or mRNA level is measured, step (a) in some cases may involve a polynucleotide amplification reaction, such as a polymerase chain reaction (PCR), especially a reverse transcriptase-PCR (RT-PCR) for mRNA detection or quantitative PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:1, 2, or 4 or a complement thereof. In some cases, the polynucleotide probe may include a detectable moiety.

In some embodiments, when the subject is indicated as having NAFLD (especially NAFLD-HCC) or having an increased risk for developing NAFLD (especially NAFLD-HCC) after the first round of method steps described above, the claimed method may further include repeating the same steps at a later time using the same type of sample from the subject. A decrease in SQLE level, especially SQLE expression level in mRNA or protein, at the later time as compared to the amount from the original step (a) indicates an improvement of NAFLD (especially NAFLD-HCC) or a lessened risk for the disease, whereas an increase indicates a worsening of NAFLD (especially NAFLD-HCC) or a heightened risk for the disease.

In a second aspect, the present invention provides a method for assessing likelihood of mortality in patients suffering from liver cancer (especially HCC, e.g., NAFLD-HCC) due to the disease by comparing the expression level of SQLE mRNA or protein among the patients. Briefly, the method for assessing likelihood of mortality includes the steps of: (a) measuring expression level of SQLE in a sample taken from a first patient who has been diagnosed with liver cancer (especially HCC, e.g., NAFLD-HCC), and (b) comparing the expression level obtained in step (a) with the expression level of SQLE determined in a sample of same type that was taken from a second liver cancer patient with the same diagnosis and measured in the same step (a). When the expression level of SQLE is higher in the first patient's sample than that found in the second patient's sample, the first patient is deemed as having a higher likelihood of mortality from liver cancer (especially HCC, e.g., NAFLD-HCC) than the second patient. Conversely, if the expression level of SQLE is lower in the first patient's sample than that found in the second patient's sample, the first patient is deemed as having a lower likelihood of mortality from liver cancer (especially HCC, e.g., NAFLD-HCC) than the second patient. The likelihood of mortality is referenced during a pre-determined length of time, e.g., 1, 2, 3, 4 years or 5 years, or 10 years, or 15 years post-diagnosis. Typically, the sample used in the method is a liver cancer tissue sample, e.g., one that includes cancerous hepatocytes. In some cases, blood samples such as serum or plasma samples can be used as well. The subject being tested may be a human or a member of other mammals such as primates. In some cases, the second patient is one who has been diagnosed with liver cancer (especially HCC, e.g., NAFLD-HCC) but has been previously determined as having a normal expression level of SQLE mRNA and/or protein in the liver cancer tissue.

In some embodiments of this method, the SQLE level is copy number of the SQLE genomic sequence or SQLE protein expression level. In other embodiments, the SQLE level is SQLE mRNA expression level. When the SQLE protein level is measured, step (a) may include an immunoassay using an antibody that specifically binds the SQLE protein. For example, a Western Blot analysis may be used. In other cases, step (a) may involve mass spectrometry, or a hybridization-based assay such as hybridization to a microarray, fluorescence probe, or molecular beacon.

When SQLE genomic copy or mRNA level is measured, step (a) in some cases may involve a polynucleotide amplification reaction, such as a PCR, especially an RT-PCR or quantitative PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:1, 2, or 4. In some cases, the polynucleotide probe may include a detectable moiety. The sample used in this method is a liver tissue sample taken from confirmed cancerous tissues or a blood sample such as serum or plasma sample.

In a third aspect, the present invention provides a kit for detecting the presence of or assessing the risk of NAFLD (especially NAFLD-HCC) or assessing the likelihood of mortality of NAFLD-HCC in a subject, comprising (1) a standard control that provides an average amount of SQLE protein or SQLE genomic DNA or mRNA; and (2) an agent that specifically and quantitatively identifies SQLE protein or SQLE genomic DNA or mRNA. In some cases, the agent may be an antibody that specifically binds the SQLE protein; or the agent may be a polynucleotide probe that specifically hybridizes with the SQLE genomic DNA or mRNA. For example, the polynucleotide probe hybridizes with at least a segment of SEQ ID NO:1, 2, or 4. The agent may include a detectable moiety. In other cases, the kit may further comprise two oligonucleotide primers for specifically amplifying at least a segment of SEQ ID NO:1, 2, or 4 or its complement in an amplification reaction. Typically, the kit will further include an instruction manual.

In a fourth aspect, the present invention provides a method for treating NAFLD (e.g., NAFLD-HCC). The claimed method includes the step of administering to a patient in need thereof (e.g., who has received a diagnosis of NAFLD) with an effective amount of an SQLE inhibitor such that SQLE gene copy number is reduced and/or SQLE expression at mRNA and/or protein level is suppressed. In some embodiments, the SQLE inhibitor comprises one or more gene-editing agents such those in a CRISPR system. In some embodiments, the SQLE inhibitor is a neutralizing antibody of the SQLE protein capable of reducing or blocking the SQLE enzymatic activity. In some embodiments, the inhibitor is a nucleic acid encoding a polynucleotide sequence at least partially complementary to SQLE DNA or RNA sequence or a segment thereof and capable of suppressing SQLE mRNA expression. For example, the nucleic acid may encode an antisense RNA, miRNA, or siRNA. In some embodiments, the nucleic acid is an expression cassette comprising a promoter operably linked to a nucleotide sequence complementary to a segment of SEQ ID NO:1, 2, or 4. Various promoters may be useful in this method, for example, the promoter may be an liver-specific promoter. In some embodiments, the SQLE inhibitor is Terbinafine.

In a related aspect, the present invention provides use of an SQLE inhibitor for manufacturing a medicament for treating NAFLD including NAFLD-related liver cancer (e.g., NAFLD-HCC). The SQLE inhibitor, which may suppress SQLE level by reducing SQLE mRNA expression level, SQLE protein expression level, or SQLE protein activity, can be formulated with one or more physiologically acceptable excipients for administration to a patient who has been diagnosed with colon cancer. The inhibitor may be a polynucleotide, such as an antisense RNA, miRNA, or siRNA targeting the SQLE mRNA, or a polypeptide, such as a neutralizing antibody against the SQLE protein. One exemplary SQLE inhibitor is Terbinafine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) SQLE mRNA was up-regulated in NAFLD patients (N=23) as compared to healthy normal controls (N=16). (FIG. 1B) SQLE gene expression in NAFLD was validated in two published cohort (GSE89632 and GSE48452). Paired two-tailed Student's t tests were used. Data are represented as means±SEM. (FIG. 1C) Sqle was overexpressed in a high-fat diet induced model of NAFLD in mice.

(FIG. 2A) Serum SQLE level was significantly increased in patients with NAFLD as compared to healthy peoples. (FIG. 2B) Serum SQLE levels exhibited a high overall accuracy in discriminating NASH subjects from control subjects with the area under the receiver operating characteristic curve (AUROC) of 0.781 (95% CI: 0.706-0.855).

(FIG. 3A) Schematic diagram of this experiments. (FIG. 3B) Sqle tg mice had higher liver weight-to-body weight ratio compared to wild-type mice, while the body weight remained largely unaffected. (FIG. 3C) H&E staining showed that Sqle mice had increased hepatic steatosis. (FIG. 3D) qPCR analysis and liver free fatty assay showed that Sqle expression activate Srebp1c induced fatty acid biosynthesis pathway. The concentration of liver cholesterol (FIG. 3E), serum and liver triglyceride (FIG. 3F) were markly exacerbated in Sqle tg mice. (FIG. 3G) Increased levels of serum aspartate transaminase (AST) and alanine transaminase (ALT) indicated that Sqle overexpression in the liver triggered liver injury. (FIG. 3H) Insulin tolerance tests (ITTs) revealed that insulin resistance was markedly exacerbated by Sqle overexpression in mice. *P<0.05, **P<0.01.

FIGS. 4A-4I Hepatocyte-specific overexpression of SQLE exacerbates high fat high cholesterol induced liver steatosis, liver injury, inflammation and insulin resistance in an embodiment. (FIG. 4A) Schematic diagram of this experiments. (FIG. 4B) Sqle tg mice demonstrated a significant increase in body weight and liver weight compared to wild type mice. (FIG. 4C) H&E staining showed Sqle mice exacerbated HFHC diet induced hepatic steatosis. The concentration of liver free fatty acid (FIG. 4D), serum and liver cholesterol (FIG. 4E), serum and liver triglyceride (FIG. 4F), serum ALT and AST (FIG. 4G) were markly exacerbated in Sqle tg mice. (FIG. 4H) qPCR analysis indicated Sqle overexpression increased the mRNA expression of inflammation and fibrosis markers. (FIG. 4I) ITTs and glucose tolerance tests (GTTs) revealed marked elevation of insulin resistance in high fat high cholesterol fed Sqle tg mice. *P<0.05, P<0.01, *P<0.001.

(FIG. 5A) Schematic diagram of this experiments. (FIG. 5B) Terbinafine significant inhibit Sqle tg mice body weight gain. (FIG. 5C) Mice liver weight and liver/body weight ratio also decreased after terbinafine treatment. (FIG. 5D) H&E staining showed terbinafine suppresses hepatic steatosis and inflammation in Sqle tg mice. Terbinafine also significantly decrease the concentration of liver free fatty acid (FIG. 5E), liver cholesterol (FIG. 5F), serum and liver triglyceride (FIG. 5G), serum ALT and AST (H). (FIG. 5I) qPCR analysis indicated terbinafine significantly inhibit the mRNA expression of inflammation and fibrosis markers. (J) ITTs and glucose tolerance tests (GTTs) revealed marked elevation of insulin resistance in high fat high cholesterol fed Sqle tg mice. *P<0.05, P<0.01, *P<0.001.

(FIG. 6A) Schematic diagram of this experiments. (FIG. 6B) Terbinafine significant inhibit HFHC diet induced body weight and liver weight gain in mice. Terbinafine also significantly decrease the concentration of serum cholesterol and triglyceride (FIG. 6C), serum ALT and AST (FIG. 6D). (FIG. 6E) H&E staining showed terbinafine suppresses hepatic steatosis in HFHC fed wt mice.

(FIG. 7A) RNAseq analysis of 18 paired NAFLD-HCC and adjacent normal tissues (left). SQLE was the top outlier gene among the up-regulated metabolic genes (right). (FIG. 7B) SQLE mRNA expression in the individual 17 paired NAFLD-HCC and adjacent normal samples (one paired sample was not available for analysis). (FIG. 7C) Increased SQLE mRNA and (FIG. 7D) protein expression in human NAFLD-HCC was validated in an independent cohort. (FIG. 7E) Sqle mRNA expression was up-regulated in dietary and genetic NAFLD-HCC animal models: N, N-diethylnitrosamine (DEN)-injected and high-fat diet treated wild-type mice (left) and DEN-treated db/db mice (right). (FIG. 7F) Correlation analysis between SQLE gene copy number and mRNA expression in 17 paired NAFLD-HCC. Data are represented as means±SEM. (FIGS. 7C-E) Paired two-tailed Student's t tests were used. (FIG. 7F) The Pearson correlation coefficient was used.

(FIG. 8A) Increased SQLE mRNA and (FIG. 8B) protein expression in human HCC was determined in our own Guangzhou cohort. (FIG. 8C) SQLE mRNA expression in HCC was validated in TCGA-LIHC (N=50 pairs) and Stanford cohorts (N=65 pairs) Paired two-tailed Student's t tests were used. Data are represented as means±SEM.

FIG. 12: SQLE inhibitor terbinafine suppresses tumor growth in two xenograft nude mice models in an embodiment. (A1) Terbinafine (80 mg/kg/d, p.o.) inhibited growth of subcutaneous HepG2 xenografts, as evidenced by significant reductions in (A2) tumor volume and weight. (A3)

Figure 1A:
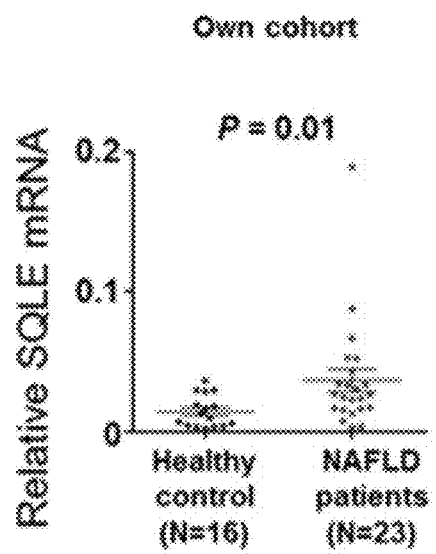
FIGS. 1A-1C: SQLE is frequently up-regulated in human and mouse NAFLD in an embodiment.

Terbinafine increased the survival of mice harboring HepG2 xenografts. Kaplan-Meier analysis and log-rank test was used. (B1) Terbinafine (80 mg/kg/d, p.o.) attenuated growth of orthotopic HKCI2 xenografts. (B2) Both tumor volume and weight were reduced. (C1) Terbinafine lowered the levels of free cholesterol and cholesteryl ester in HepG2 xenografts. (C2) Terbinafine-treated HKCI2 xenografts had lower levels of free cholesterol and cholesteryl ester. Data are represented as means±SEM. **$P<0.01$.

FIG. 13: SQLE inhibitor terbinafine decreases NAFLD-HCC incidence and tumor number in Sqle Tg mice in an embodiment. (A) Schematic diagram of this experiments. (B1) Terbinafine (80 mg/kg/d, p.o.) suppressed tumorigenesis in DEN-injected and high-fat high-cholesterol diet treated Sqle tg mice, both in terms of tumor incidence and tumor number (B2). (C) H&E and Ki-67 staining of vehicle and terbinafine-treated livers. (D) Terbinafine treatment decreased liver to body weight ratio (left), liver and serum cholesterol levels (middle), and NADP+/NADPH ratio (right). (E) Representative western blot analysis showed terbinafine suppressed Sqle expression and reversed the effect of SQLE on downstream factors DNMT3A and PTEN. Data are represented as means±SEM. *$P<0.05$, $P<0.01$, *$P<0.001$.

DEFINITIONS

The term "Squalene Epoxidase" or "SQLE," as used herein, refers to any naturally occurring variants or mutants, interspecies homologs or orthologs, or man-made variants of an SQLE gene or SQLE protein, especially the human gene. Located on chromosome 18, the human SQLE gene has an mRNA sequence set forth in GenBank Accession No. NM 003129.3 (provided herein as SEQ ID NO:1), which translate to a coding sequence (GenBank Accession No. CCDS47918.1, provided herein as SEQ ID NO:2) for a 574-amino acid SQLE protein (GenBank Accession No. NP_003120, provided herein as SEQ ID NO:3). A SQLE protein within the meaning of this application typically has at least 80%, or 90%, or 95% or higher sequence identity to the human wild-type SQLE protein and retains at least 80% of the same enzymatic activity as the wild-type enzyme.

In this disclosure the term "non-alcoholic fatty liver disease (NAFLD)" is used to refer to any liver pathology characterized by ectopic fat deposition in the liver that is not caused by alcohol consumption. An "NAFLD" encompasses a variety of conditions such as steatosis, non-alcoholic steatohepatitis (NASH), and liver fibrosis, cirrhosis, and liver cancer (especially hepatocellular carcinoma) associated with or caused by a non-alcoholic fatty liver disease (NAFLD-HCC).

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human SQLE protein) or the translation of a protein encoded by a polynucleotide sequence. In other words, both mRNA level and protein level encoded by a gene of interest (e.g., human SQLE gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, liver biopsy of normal/healthy/non-cancerous tissue as well as diseased or cancerous tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cells, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant SQLE protein used in the method of this invention (e.g., for treating NAFLD) has at least 80% sequence identity, preferably 85%, 90%, 91%, 92%, 93, 94%, 95%, 96%, 97%, 98%, 99%, or 100% identity, to a reference sequence, e.g., a wild-type human SQLE protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of SQLE mRNA or SQLE protein found in non-cancerous liver tissue or in a healthy individual's blood especially serum or plasma). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

The term "inhibiting" or "inhibition," as used herein, refers to any detectable negative effect on a target biological process, such as cellular signal transduction, cell proliferation, tumorigenicity, metastatic potential, and recurrence of a disease/condition. Typically, an inhibition is reflected in a decrease of at least 10%, 20%, 30%, 40%, or 50% in target process (e.g., expression of SQLE at either mRNA level or protein level) upon application of an inhibitor, when compared to a control where the inhibitor is not applied.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human SQLE or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site" means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is a heterologous moiety attached to a probe or a molecule with defined binding characteristics (e.g., a polypeptide with a known binding specificity or a polynucleotide), so as to allow the presence of the probe/molecule (and therefore its binding target) to be readily detectable. The heterologous nature of the label ensures that it has an origin different from that of the probe or molecule that it labels, such that the probe/molecule attached with the detectable label does not constitute a naturally occurring composition.

"Standard control" as used herein refers to a predetermined amount or concentration of a polynucleotide sequence or polypeptide, e.g., SQLE genomic DNA, mRNA, or protein, that is present in an established normal disease-free tissue sample, e.g., a normal liver tissue sample or a blood sample (e.g., serum or plasma) from a heathy individual without any liver disease. The standard control value is suitable for the use of a method of the present invention, to serve as a basis for comparing the amount of SQLE genomic DNA, mRNA, or protein that is present in a test sample. An established sample serving as a standard control provides an average amount of SQLE mRNA or SQLE protein or an average copy number of SQLE genomic sequence that is typical for a blood (e.g., serum or plasma) sample or a liver tissue sample of an average, healthy human without any liver disease especially NAFLD, preferably without any increased risk of developing the disease. A standard control value may vary depending on the nature of the sample as well as other factors such as the gender, age, ethnicity of the subjects based on whom such a control value is established.

The term "average," as used in the context of describing a human who is healthy, free of any liver disease (especially NAFLD), refers to certain characteristics, especially the copies of SQLE genomic sequence or amount of SQLE mRNA or protein, found in the person's liver tissue or blood sample (e.g., serum or plasma), that are representative of a randomly selected group of healthy humans who are free of any liver diseases (especially NAFLD) and free of elevated risk of developing the disease. This selected group should comprise a sufficient number of humans such that the average copy number and average amount of SQLE mRNA or protein in the sample among these individuals reflects, with reasonable accuracy, the corresponding copy number of SQLE gene and amount of SQLE mRNA/protein in the general population of healthy humans. In addition, the selected group of humans generally have a similar age to that of a subject whose sample is tested for indication of NAFLD. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human SQLE genomic DNA, SQLE mRNA, or SQLE protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding an SQLE antisense RNA is the amount of said polynucleotide to achieve a decreased level of SQLE mRNA or protein expression or biological activity, such that the symptoms, severity, and/or recurrence chance of NAFLD are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, NAFLD especially NAFLD-HCC. Subjects also include individuals currently undergoing therapy that seek manipulation of the therapeutic regimen. Subjects or individuals in need of treatment include those that demonstrate symptoms of NAFLD or are at risk of suffering from NAFLD or its symptoms. For example, a subject in need of treatment includes individuals with a genetic predisposition or family history for NAFLD such as NAFLD-HCC, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of SQLE protein are used to refer to inhibitory, activating, or modulating molecules, respectively, identified using in vitro and in vivo assays for SQLE protein binding or signaling or enzymatic activity, e.g., ligands, agonists, antagonists, and their homologs and mimetics. The term "modulator" includes inhibitors and activators. Inhibitors are agents that, e.g., partially or totally block binding, decrease, prevent, delay activation, inactivate, desensitize, or down regulate the activity of SQLE protein. In some cases, the inhibitor directly or indirectly binds to SQLE protein, such as a neutralizing antibody. Inhibitors, as used herein, are synonymous with inactivators and antagonists. Activators are agents that, e.g., stimulate, increase, facilitate, enhance activation, sensitize or up regulate the activity of SQLE protein. Modulators include SQLE protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

The term "terbinafine" refers to a chemical compound having the structure of

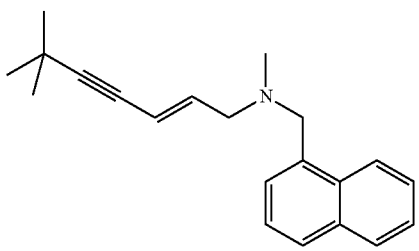 [SMILES: CN(C/C=C/C#CC(C)(C)C)Cc1cccc2ccccc12]

and the chemical formula of $C_{21}H_{25}N$. Due to its fungicidal activity, terbinafine has been used as an antifungal medication formulated for topical and oral administration, sold under various brand names such as Lamisil.

DETAILED DESCRIPTION OF THE INVENTION

I. Introduction

Non-alcoholic fatty liver disease (NAFLD) includes a number of liver pathologies ranging from the relatively benign steatosis to the more aggressive and potentially fatal conditions such as nonalcoholic steatohepatitis (NASH) and NAFLD-caused hepatocellular carcinoma (NAFLD-HCC). With 15-25% of all NAFLD patients eventually progressing to NASH or HCC, NAFLD presents a major health concern especially in developed countries.

Squalene epoxidase (SQLE) is a rate-limiting enzyme for cholesterol biosynthesis. SQLE overexpression causes a more notable rise in cholesteryl esters. Cholesteryl esters are able to induce proliferation of many cancer cells, including NAFLD-HCC cells. Human SQLE is located on chromosome 8q24.13, a genomic region that is frequently amplified in multiple cancers include HCC. Terbinafine is an FDA-approved oral drug, and its efficacy, safety and tolerability has been shown in the treatment of fungal infections in humans. Terbinafine inhibits the activity of fungal squalene epoxidase (SQLE), thus blocking the biosynthesis of cholesterol and suppressing fungal growth. There is no prior report that terbinafine could inhibit human SQLE to suppress HCC development. It is necessary to investigate the therapeutic effect of terbinafine on human NAFLD, especially NASH and NAFLD-HCC.

The present inventors discovered for the first time that increased copy number of genomic SQLE sequence, and overexpression of SQLE, both at the mRNA and protein levels, are often observed in samples taken from NAFLD patients. This overexpression of SQLE protein is at least in part due to increased copy number in the SQLE genomic sequence, which leads to increased transcription of SQLE mRNA. This discovery provides important means for detecting, monitoring, and treating NAFLD including NAFLD- HCC. Generally, a higher than normal SQLE gene copy number and mRNA/protein level seen in a test subject, who may or may not exhibit any signs of liver disorder or anomaly, indicates a high likelihood that the subject already has or will later develop NAFLD including liver cancer associated with NAFLD. Similarly, a higher SQLE gene copy number or mRNA/protein level indicates a higher likelihood of mortality in a NAFLD-HCC patient who may have already received treatment for liver cancer (such as surgical removal of the primary tumor mass, radiotherapy, and chemotherapy) due to the disease, in comparison to another NAFLD-HCC patient who has a lower SQLE gene copy number and/or mRNA/protein level, for example, one who has a normal SQLE gene copy number and/or normal mRNA/protein level compared healthy human subjects who do not have NAFLD-HCC and are not at any increased risk of developing the disease. The identification of SQLE's role in NAFLD especially NAFLD-HCC leads to the development of targeted treatment of NAFLD with SQLE inhibitors such as terbinafine.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human SQLE gene, and synthetic oligonucleotides (e.g., primers) can be verified using, e.g., the chain termination method for double-stranded templates of Wallace et al., *Gene* 16: 21-26 (1981).

III. Acquisition of Tissue Samples and Analysis of SQLE mRNA or DNA

The present invention relates to measuring the amount of SQLE mRNA or SQLE genomic DNA found in a person's liver tissue or blood sample (for example, serum or plasma sample), as a means to detect the presence, to assess the risk of developing, and/or to monitor the progression or treatment efficacy of NAFLD, including assessing the likelihood of mortality due to the disease. Thus, the first steps of practicing this invention are to obtain a liver tissue sample or blood sample from a test subject and extract mRNA or DNA from the sample.

A. Acquisition and Preparation of Samples

A liver tissue sample or blood sample is obtained from a person to be tested or monitored for NAFLD using a method of the present invention. Collection of liver tissue sample or blood sample from an individual is performed in accordance with the standard protocol hospitals or clinics generally follow. An appropriate amount of liver tissue or blood is collected and may be stored according to standard procedures prior to further preparation.

The analysis of SQLE mRNA or DNA found in a patient's sample according to the present invention may be performed using, e.g., liver tissue or serum or plasma. The methods for preparing patient samples for nucleic acid extraction are well known among those of skill in the art. For example, a subject's liver tissue sample should be first treated to disrupt cellular membrane so as to release nucleic acids contained within the cells.

B. Extraction and Quantitation of DNA and RNA

Methods for extracting DNA from a biological sample are well known and routinely practiced in the art of molecular biology (e.g., described by Sambrook and Russell, *Molecular Cloning: A Laboratory Manual* 3d ed., 2001). RNA contamination should be eliminated to avoid interference with DNA analysis.

Likewise, there are numerous methods for extracting mRNA from a biological sample. The general methods of mRNA preparation can be followed, see, e.g., Sambrook and Russell, supra; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of DNA or mRNA Level

Once DNA or mRNA is extracted from a sample, the amount of human SQLE genomic DNA or mRNA may be quantified. The preferred method for determining the DNA or mRNA level is an amplification-based method, e.g., by polymerase chain reaction (PCR), especially reverse transcription-polymerase chain reaction (RT-PCR) for mRNA quantitative analysis.

While SQLE genomic DNA is directly subject to amplification, mRNA must be first reverse transcribed. Prior to the amplification step, a DNA copy (cDNA) of the human SQLE mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target genomic DNA or mRNA is typically used in practicing the present invention, one of skill in the art will recognize, however, that amplification of these DNA or mRNA species in a sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of DNA or mRNA in the sample. For a review of branched-DNA signal amplification for direct quantitation of nucleic acid sequences in clinical samples, see Nolte, Adv. *Clin. Chem.* 33:201-235, 1998.

2. Other Quantitative Methods

The SQLE DNA or mRNA can also be detected using other standard techniques, well known to those of skill in the art. Although the detection step is typically preceded by an amplification step, amplification is not required in the methods of the invention. For instance, the DNA or mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target DNA or mRNA, the amount of which may then be compared to the control based on the intensity of the band. Alternatively, oligonucleotide probes specific to SQLE DNA or mRNA can be used to detect the presence of such DNA or mRNA species and indicate the amount of DNA or mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

IV. Quantitation of Polypeptides

A. Obtaining Samples

The first step of practicing the present invention is to obtain a sample of liver tissue or blood from a subject being tested, assessed, or monitored for NAFLD, the risk of developing NAFLD, or the severity/progression/chance of survival of the condition. Samples of the same type should be taken from both a control group (normal individuals not suffering from any liver disorder especially NAFLD) and a test group (subjects being tested for possible NAFLD, for example). Standard procedures routinely employed in hospitals or clinics are typically followed for this purpose, as stated in the previous section.

For the purpose of detecting the presence of NAFLD or assessing the risk of developing NAFLD in test subjects, individual patients' blood samples or liver tissue samples may be taken and the level of human SQLE protein may be measured and then compared to a standard control. If a decrease in the level of human SQLE protein is observed when compared to the control level, the test subject is deemed to have NAFLD or have an elevated risk of developing the condition. For the purpose of monitoring disease progression or assessing therapeutic effectiveness NAFLD patients, individual patient's blood or liver tissue samples may be taken at different time points, such that the level of human SQLE protein can be measured to provide information indicating the state of disease. For instance, when a patient's SQLE protein level shows a general trend of decrease over time, the patient is deemed to be improving in the severity of NAFLD or the therapy the patient has been receiving is deemed effective. A lack of change in a patient's SQLE protein level or a continuing trend of increase on other hand would indicate a worsening of the condition and ineffectiveness of the therapy given to the patient. Generally, a higher SQLE protein level seen in a patient indicates a more severe form of the NAFLD the patient is suffering from and a worse prognosis of the disease, as manifested in the case of NAFLD-HCC a shorter life expectancy, higher rate of metastasis, resistance to therapy, higher chances of recurrence, etc. Among NAFLD-HCC patients, one who has a higher level of SQLE protein expression in his sample than that found in the same type of sample in a second NAFLD-HCC patient has a higher likelihood of disease mortality compared to the second patient for any defined time period, such as 1-5 years, 5 years, 10 years, or 15 years post-diagnosis.

B. Preparing Samples for SQLE Protein Detection

The liver tissue or blood sample from a subject is suitable for the present invention and can be obtained by well-known methods and as described in the previous section. In certain applications of this invention, liver tissue or serum/plasma may be the preferred sample type.

C. Determining the Level of Human SQLE Protein

A protein of any particular identity, such as SQLE protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human SQLE protein) can also be detected by gel electrophoresis (such as 2-dimensional gel electrophoresis) and western blot analysis using specific antibodies. Alternatively, standard immunohistochemical techniques can be used to detect a given protein (e.g., human SQLE protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human SQLE protein) can be generated by known techniques.

Other methods may also be employed for measuring the level of SQLE protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any liver disease (especially any form of NAFLD) as conventionally defined is first selected. These individuals are within the appropriate parameters, if applicable, for the purpose of screening for and/or monitoring NAFLD using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human SQLE genomic DNA, SQLE mRNA, or SQLE protein in the liver tissue sample or blood sample obtained from the group can be reasonably regarded as representative of the normal or average level among the general population of healthy people. Preferably, the selected group comprises at least 10 human subjects.

Once an average value for the SQLE genomic DNA, mRNA, or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of NAFLD

By illustrating the correlation of over-expression of SQLE mRNA/protein and NAFLD, such as NASH and NAFLD-HCC, the present invention further provides a means for treating patients suffering from these conditions: by way of suppressing SQLE mRNA or protein expression or inhibiting SQLE protein's biological activity. As used herein, treatment of an NAFLD encompasses reducing, reversing, lessening, or eliminating one or more of the symptoms of the condition, as well as preventing or delaying the onset of one or more of the relevant symptoms, including reducing mortality or likelihood of disease recurrence among patients who have already received initial treatment. Inhibitors of SQLE can be of virtually any chemical and structural nature: they may be polypeptides (e.g., antibody, antibody fragment, aptamer), polynucleotides (e.g., antisense DNA/RNA, small inhibitory RNA, or micro RNA), and small molecules. As long as they possess confirmed inhibitory effect against SQLE expression or activity, such inhibitors may be useful for inhibiting liver cancer cell proliferation and therefore useful for treating liver cancer especially NAFLD-HCC.

A. Suppressing SQLE Expression or Activity

1. Inhibitors of SQLE mRNA

Suppression of SQLE expression can be achieved through the use of nucleic acids siRNA, microRNA, miniRNa, lncRNA, antisense oligonucleotides, aptamer. Such nucleic acids can be single-stranded nucleic acids (such as mRNA) or double-stranded nucleic acids (such as DNA) that can translate into an active form of inhibitor of SQLE mRNA under appropriate conditions.

In one embodiment, the SQLE inhibitor-encoding nucleic acid is provided in the form of an expression cassette, typically recombinantly produced, having a promoter operably linked to the polynucleotide sequence encoding the inhibitor. In some cases, the promoter is a universal promoter that directs gene expression in all or most tissue types; in other cases, the promoter is one that directs gene expression specifically in liver cells or hepatocytes. Administration of such nucleic acids can suppress SQLE expression in the target tissue, e.g., hepatocytes. Since the human SQLE gene sequence encoding its mRNA is known as GenBank Accession No. NM_003129.3 and provided herein as SEQ ID NO:1, and its cDNA sequence is provided herein as SEQ ID NO:2, one can devise a suitable SQLE-suppressing nucleic acid from the sequence, species homologs, and variants of these sequences.

2. Inhibitors of SQLE Protein

Suppression of SQLE protein activity can be achieved with an agent that is capable of inhibiting the activity of SQLE protein. An in vitro assay can be used to screen for potential inhibitors of SQLE protein activity based in the binding between SQLE protein and a candidate compound. Once a compound is identified in the binding assay, further testing may be conducted to confirm and verify the compounds capability to inhibiting SQLE protein activity. In general, such an assay can be performed in the presence of SQLE protein or a fragment thereof, for example, a recombinantly produced SQLE protein or fragment, under conditions permitting its binding to a potential binding partner. For convenience, the SQLE protein or the candidate compound may be immobilized onto a solid support and/or labeled with a detectable moiety. A third molecule, such as an antibody (which may include a detectable label) to SQLE protein, can also be used to facilitate detection.

In some cases, the binding assays can be performed in a cell-free environment; whereas in other cases, the binding assays can be performed within a cell or on the cell surface, for example, using cells recombinantly or endogenously expressing an appropriate SQLE protein. Since SQLE is an enzyme, an potential inhibitor of SQLE can be readily verified in an enzymatic assay where SQLE activity is monitored and compared in the presence or absence of a candidate compound: when the presence of a candidate compound leads to suppressed SQLE activity, the compound is verified as an SQLE inhibitor; conversely, when the presence of a candidate compound leads to enhanced SQLE activity, the compound is verified as an activator of the enzyme.

The anti-NAFLD effects of an SQLE protein inhibitor of the present invention can also be demonstrated in in vivo assays. For example, an SQLE protein inhibitor can be injected into animals that have a compromised immune system (e.g., nude mice, SCID mice, or NOD/SCID mice) and therefore permit xenograft tumors. Injection methods can be subcutaneous, intramuscular, intravenous, intraperitoneal, or intratumoral in nature. NAFLD-HCC xenograft tumor development is subsequently monitored by various means, such as measuring tumor volume and scoring secondary lesions due to metastases, in comparison with a control group of animals with similar tumors but not given the inhibitor. The Examples section of this disclosure provides detailed description of some exemplary in vivo assays. An inhibitory effect is detected when a negative effect on tumor growth or metastasis is established in the test group. Preferably, the negative effect is at least a 10% decrease; more preferably, the decrease is at least 20%, 30%, 40%, 50%, 60%, 70%, 80%, or 90%.

As stated above, SQLE protein inhibitors can have diverse chemical and structural features. For instance, an inhibitor can be a non-functional SQLE protein mutant that retaining the binding ability of SQLE protein to its substrate, cofactors or other binding partners, an antibody to the SQLE protein that interferes with SQLE protein activity (e.g., a neutralizing antibody), or any small molecule or macromolecule that simply hinders the interaction between SQLE protein and its substrate, cofactors or other binding partners. Essentially any chemical compound can be tested as a potential inhibitor of SQLE protein activity. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. Pharmaceutical Compositions

1. Formulations

Compounds of the present invention are useful in the manufacture of a pharmaceutical composition or a medicament. A pharmaceutical composition or medicament can be administered to a subject for the treatment of NAFLD.

Compounds used in the present invention, e.g., an inhibitor of SQLE mRNA or protein (e.g., a neutralizing antibody against SQLE protein), a nucleic acid encoding a polynucleotide or polypeptide inhibitor for SQLE gene expression or SQLE protein activity (e.g., an expression vector encoding a neutralizing antibody against SQLE protein), are useful in the manufacture of a pharmaceutical composition or a medicament comprising an effective amount thereof in conjunction or mixture with excipients or carriers suitable for application.

An exemplary pharmaceutical composition for suppressing SQLE expression comprises (i) an express cassette comprising a polynucleotide sequence encoding an inhibitor of SQLE protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

An SQLE inhibitor or a nucleic acid encoding an SQLE inhibitor can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., liver cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E.W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., an SQLE inhibitor or a nucleic acid encoding an SQLE inhibitor, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., an SQLE inhibitor or a nucleic acid encoding an SQLE inhibitor, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that decreases the level or activity of SQLE protein, and (ii) another therapeutic agent.

When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control NAFLD as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of SQLE inhibitor or nucleic acid encoding an SQLE inhibitor will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for an SQLE inhibitor or a nucleic acid encoding an SQLE inhibitor described herein are provided. Dosage for a SQLE inhibitor-encoding nucleic acid, such as an expression cassette, can be between 0.1-0.5 mg/eye, with intravitreous administration (e.g., 5-30 mg/kg). Small organic compounds inhibitors can be administered orally at between 5-1000 mg, or by intravenous infusion at between 10-500 mg/ml. Monoclonal antibody inhibitors can be administered by intravenous injection or infusion at 50-500 mg/ml (over 120 minutes); 1-500 mg/kg (over 60 minutes); or 1-100 mg/kg (bolus) five times weekly. SQLE protein or mRNA inhibitors can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., an SQLE inhibitor or a nucleic acid encoding an SQLE inhibitor). The additional therapeutic compound can also be administered separately, in a separate composition, or a different dosage form from the main active ingredient. Some doses of the main ingredient, such as an SQLE inhibitor or a nucleic acid encoding an SQLE inhibitor, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess SQLE level, both at the levels of SQLE mRNA and protein, as well as in the number of copies of SQLE genomic sequence, in a subject, which can be used for various purposes such as detecting or diagnosing the presence of an NAFLD especially NASH or NAFLD-HCC, determining the risk of developing the condition, and monitoring progression of the condition in a patient, including assessing the likelihood of survival from the condition, especially NAFLD-CHH among patients who have received a diagnosis of the disease and may have been treated, e.g., by surgery, chemotherapy, and/or radiotherapy.

Kits for carrying out assays for determining SQLE mRNA level or SQLE gene copy number typically include at least one oligonucleotide useful for specific hybridization with at least one segment of the SQLE coding sequence or its complementary sequence. Optionally, this oligonucleotide is labeled with a detectable moiety. In some cases, the kits may include at least two oligonucleotide primers that can be used in the amplification of at least one segment of SQLE DNA or mRNA by PCR, particularly by RT-PCR. Table 1 provides some examples of such primers.

Kits for carrying out assays for determining SQLE protein level typically include at least one antibody useful for specific binding to the SQLE protein amino acid sequence. Optionally, this antibody is labeled with a detectable moiety. The antibody can be either a monoclonal antibody or a polyclonal antibody. In some cases, the kits may include at least two different antibodies, one for specific binding to the SQLE protein (i.e., the primary antibody) and the other for detection of the primary antibody (i.e., the secondary antibody), which is often attached to a detectable moiety.

Typically, the kits also include an appropriate standard control. The standard controls indicate the average value of SQLE protein or mRNA or an average copy number of the SQLE genomic sequence in the liver tissue of healthy subjects not suffering from or at increased risk of developing NAFLD. In some cases such standard control may be provided in the form of a set value. In addition, the kits of this invention may provide instruction manuals to guide users in analyzing test samples and assessing the presence or risk of NAFLD, or likelihood of survival from NAFLD-HCC in a test subject.

In a further aspect, the present invention can also be embodied in a device or a system comprising one or more such devices, which is capable of carrying out all or some of the method steps described herein. For instance, in some cases, the device or system performs the following steps upon receiving a liver tissue sample taken from a subject being tested for detecting NAFLD, assessing the risk of developing NAFLD, or assessing the likelihood of survival from NAFLD-HCC: (a) determining in sample the amount or concentration of SQLE mRNA or protein, or the number of copies of SQLE genomic sequence; (b) comparing the amount/concentration or copy number with a standard control value; and (c) providing an output indicating whether NAFLD is present in the subject or whether the subject is at risk of developing NAFLD, or whether the patient has an increased likelihood of mortality due to NAFLD-HCC, e.g., after the initial diagnosis and/or treatment. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Materials and Methods

A. Human Liver Specimens

Tissue Samples

Human NAFLD-HCC tumor tissues and adjacent normal tissues were collected from patients with biopsy-proven NAFLD-HCC in Prince of Wales Hospital, the Chinese University of Hong Kong. Written informed consent was obtained from all subjects and study protocol was approved by the Clinical Research Ethics Committee of the Chinese University of Hong Kong. Human HCC tumors and adjacent normal tissues, which were collected during operations prior to any therapeutic intervention at the Third Affiliated Hospital of Sun Yat-Sen University (Guangzhou, China). Written informed consent was obtained from all subjects and the study protocol was approved by the Clinical Research Ethics Committee of the Sun Yat-Sen University of Medical Sciences.

Tumor Cell Lines

2 NAFLD-HCC cell lines (HKCI2, HKCI10) and one liver cancer cell line HepG2 were used in this study. Cell lines were maintained in RPMI-1640 or DMEM medium (Gibco BRL, Rockville, Md.) with 10% fetal bovine serum.

B. Transgenic Mice Model and Nude Mice Model

Hepatocyte-Specific Sqle Expression Mice Model

Sqle transgenic mice (pCAG-loxp-stop-loxp-Rosa26-Sqle) were generated by BIOCYTOGEN Company (Beijing, China). Sqle-IRES-eGFP was cloned into Rosa26 Wild type allele to generate a gene targeting vector. Then, the Rosa26-Sqle-IRES-eGFP vectors were transfected into embryonic stem cells with C57BL/6 background. Following selection and identification by PCR and southern blot, positive clones were inject into mouse blastocysts to generate chimeric mice. Chimeric mice were mated with WT C57BL/6 mice to obtain the Rosa26-Sqle mice. To drive the hepatocyte-specific expression of Sqle, Rosa26-Sqle mice were crossed to B6.Cg-Tg (Alb-cre) 21Mgn/JNju mice (Nanjing University, China). Sqle tg/Alb-Cre mice were confirmed by PCR genotyping.

Diet

WT and Sqle Tg mice were fed with normal diet (18% fat, 58% carbohydrate, 24% protein, 0% cholesterol) or high fat high cholesterol (HFHC: 43.7% fat, 36.6% carbohydrate, 19.7% protein, 0.203% cholesterol) diets (Specialty Feeds, Glen Forrest, Wash.) ad libitum for different time point to generate spontaneous NAFLD model and diet-induced NASH model.

Liver Cholesterol levels 2 mg tissues were harvested, and liver cholesterol levels were detected by Cholesterol/Cholesteryl Ester Quantification kit (ab65359, Abcam) according to manufacturer's instructions. All experiments were conducted three times in triplicates. Results were shown as the means±SEM.

Liver Triglyceride (TG) Levels 100 mg tissues were harvested, and liver triglyceride levels were detected by triglyceride Quantification kit (ab65336, Abcam) according to manufacturer's instructions. All experiments were conducted three times in triplicates. Results were shown as the means±SEM.

Nude Mice Model

A xenograft human liver cancer mouse model was established using HepG2 cells. HepG2 cells ($1 \times 10^7$ cells in 0.1 ml PBS) were injected subcutaneously into the left dorsal flank of 4-week-old male Balb/c nude mice. Once the subcutaneous tumors reached about 100 mm$^3$, these mice were divided into vehicle group (PBS, p.o.) and terbinafine group (80 mg/kg, p.o.) randomly. Tumor diameter was measured every days for 10 days. For survival analysis, tumor diameter was measured every two days for 40 days. Tumor volume (mm³) was estimated by measuring the longest and shortest diameter of the tumor and calculating as follows: volume= (shortest diameter)²×(longest diameter)×0.5. Care of animals and all experimental procedures were approved by the Animal Ethics Committee of the Chinese University of Hong Kong. After more than 2 weeks, the mice were sacrificed, and the tumors were weighed and fixed in formalin for histological analysis. All experimental procedures were approved by the Animal Ethics Committee of the Chinese University of Hong Kong.

An orthotopic human NAFLD-HCC mouse model was established using HKCI2 cells. HKCI2 cells ($1\times10^7$ cells in 0.1 ml PBS) were injected subcutaneously into the left dorsal flank of 4-week-old male Balb/c nude mice. Subcutaneous tumors were harvested once they reached about 10 mm³ and cut into 1.0 mm³ pieces. One piece of a tumor was implanted into the left liver lobe in a separate group of nude mice (4-week-old). Four weeks after implantation, these mice were divided into vehicle group (PBS, p.o.) and terbinafine group (80 mg/kg, p.o.). Eight weeks post-implantation, the mice were sacrificed and examined.

NAFLD Mice Model

Sqle tg mice and their wild-type littermates (WT) were fed a high fat high cholesterol diet at the age of 6 weeks. At 17 weeks of age (Sqle tg mice) or 24 weeks of age (WT mice), the mice will be randomized into two group and treated with either vehicle or Terbinafine (80 mg/kg/d, oral gavage). After 8 (WT mice) or 9 weeks (Sqle tg mice) terbinafine treatment, mice will be sacrificed to examine the therapeutic effect of Terbinafine.

Assessment of NAFLD: Liver histology were evaluated at sacrifice using H&E staining. Assessment of inflammation: Liver damage were determined using serum ALT and AST. PCR and cytokine arrays were used to evaluate expression of pro-inflammatory cytokines. Assessment of metabolic syndrome: Insulin tolerance tests and glucose tolerance tests will be determined as described above.

Sqle tg Mice Model

Sqle tg mice injected with DEN (10 days of age) and fed with a HFHC diet (6 weeks of age). At 20 weeks of age, the mice will be randomized into two group and treated with either vehicle or Terbinafine (80 mg/kg/d, oral gavage). After 8 weeks terbinafine treatment, mice will be sacrificed to examine the therapeutic effect of Terbinafine.

All animal studies were performed in accordance with guidelines approved by the Animal Experimentation Ethics Committee of the Chinese University of Hong Kong.

C. Gene Expression Analysis

RNA Isolation

Total RNA was isolated using Qiazol reagent (Qiagen, Valencia, Calif., USA). First, about $5\text{-}10\times10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring the absorbance at 260 nm/280 nm using NanoDrop ND-1000 (NanoDrop Technologies, Wilmington, Del., USA). The purified RNA was store at −80° C. until using.

cDNA Synthesis

MultiScribe Reverse Transcriptase Kit (Applied Biosystems, Foster City, Calif., USA) was used to synthesize cDNA. The reaction mixture contained 1×Reverse Transcriptase buffer, 1×dNTP, 1×random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. 5 min to inactivate the enzymes. The cDNA was stored at −80° C. until other application.

Real-Time PCR

Real-time PCR was performed using 2×SYBR Green master mixture (Roche, Indianapolis, Ind.) on LightCycler® 480 Instrument. Each sample was tested in triplicate. The expression of the target gene was normalized by the expression of house-keeping gene β-actin, which served as an internal control. All primers used to amplify the transcripts are listed in Table 1.

D. Biological Function Analysis

Cell Viability Assay

Cell viability was determined by the 3-(4,5-dimethylthiazol-2-yl)-5-(3-carboxyme-thoxyphenyl)-2-(4-sulfophenyl)-2H-tetrazolium (MTS) assay (Promega, Madison, Wis.).

Colony Formation Assay

For cell colony formation assay, liver cancer cells (1000/well) were plated in 6-well plates. Different dose of Terbinafine were added to these cells at the second day. After culturing for 5-7 days, cells were fixed with 70% ethanol and stained with 0.5% crystal violet solution. Colonies with more than 50 cells per colony were counted. All experiments were conducted three times in triplicates.

Cholesterol/Cholesteryl Ester Levels $10^6$ cells or 2 mg tissues were harvested, and cholesterol/cholesteryl ester levels were detected by Cholesterol/Cholesteryl Ester Quantification kit (ab65359, Abcam) according to manufacturer's instructions. All experiments were conducted three times in triplicates. Results were shown as the means±SEM.

$NADP^+$/NADPH Ratio $2\times10^6$ cells or 50 mg tissues were harvested, and NADPH/$NADP^+$ ratio were detected by NADP/NADPH Assay Kit (ab65349, Abcam) according to manufacturer's instructions. All experiments were conducted three times in triplicates. Results were shown as the means±SEM.

Liver Free Fatty Acid Assay 20 mg tissues were harvested, and liver triglyceride levels were detected by free fatty acid Quantification kit (ab65341, Abcam) according to manufacturer's instructions. All experiments were conducted three times in triplicates. Results were shown as the means±SEM.

Serum Cholesterol, TG, ALT and AST Test

The serum cholesterol, TG, ALT and AST level were detected by the Catalyst One Chemistry Analyzer according to the manufacturer's instructions (IDEXX, USA). Thirty microliters of serum from wild-type or Sqle tg mice were diluted to 90 μl by physiological saline buffer. The diluted samples and specific slides (cholesterol, ALT and AST) were then loaded into the analyzer for automatic analysis.

Serum SQLE Detection

Serum level of SQLE in human samples was measured by using the human SQLE ELISA Kit (SEH135Hu, Cloud- Clone, Houston) according to manufacturer's instructions. All experiments were conducted three times. Results were shown as the means±SEM.

Insulin Resistance Test (ITT) and Glucose Tolerance Test (GTT)

For the glucose tolerance test, mice were fasted overnight by transferring mice to clean cages with no food or feces in upper or bottom of cage. Mice were then injected intraperitoneally with 0.75 U insulin per kg body weight (ITT) or 1 g glucose per kg body weight (GTT) in water. Blood from the tail vein was obtained before the injection and at 30, 60 and 90 min after the injection for determination of blood glucose using Glucose Meter.

Serum Alpha-Fetoprotein (AFP) Test

Mouse serum AFP level were detected by the Mouse α-Fetoprotein/AFP ELISA kit according to the manufacturer's instructions (MAF000, R&D Systems). Ten microliters of serum from wild-type or Sqle tg mice were diluted to 200 μl by Calibrator Diluent RD5-26 buffer (diluted 1:4). Then add 50 μl of diluted samples, standard and control to each microplate well for further analysis.

Ki-67 Staining

Cell proliferation was assayed by immunoperoxidase staining with anti-Ki-67 antibody (ab833; Abcam, Cambridge, UK). Negative controls were run by replacing the primary antibody with nonimmune serum. The proliferation index was determined by counting the numbers of positive staining cells as percentages of the total number of liver cells. At least 1000 cells were counted each time.

E. Statistical Analysis

All statistical tests were performed using SPSS or GraphPad Software. Data are presented as means±SEM. The Pearson correlation coefficient was used to evaluate the correlation between SQLE gene amplification and expression in the clinical samples. Multiple group comparisons were analyzed by one-way ANOVA. Overall survival in relation to expression was evaluated by the Kaplan-Meier survival curve and the log-rank test. Mann-Whitney U test or Student's t test was performed to compare the variables of two groups. The difference in cell viability and tumor growth rate between the two groups of nude mice was determined by ANOVA with repeated-measures analysis of variances. P values<0.05 were taken as statistical significance.

Results

SQLE is Overexpressed in Human and Mouse NAFLD

Figure 1B:
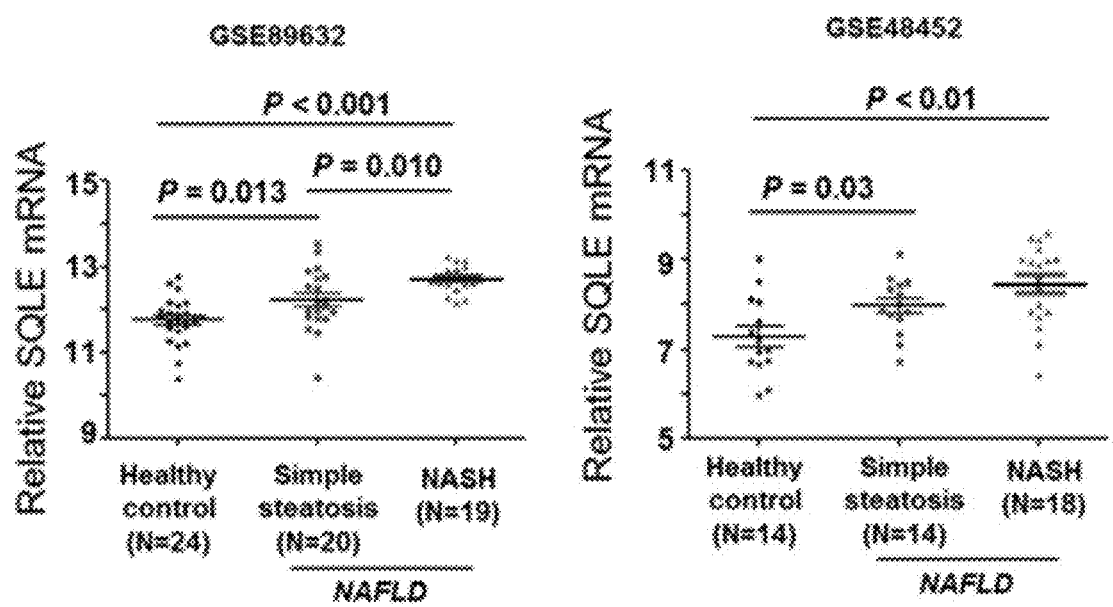
Figure 1C:
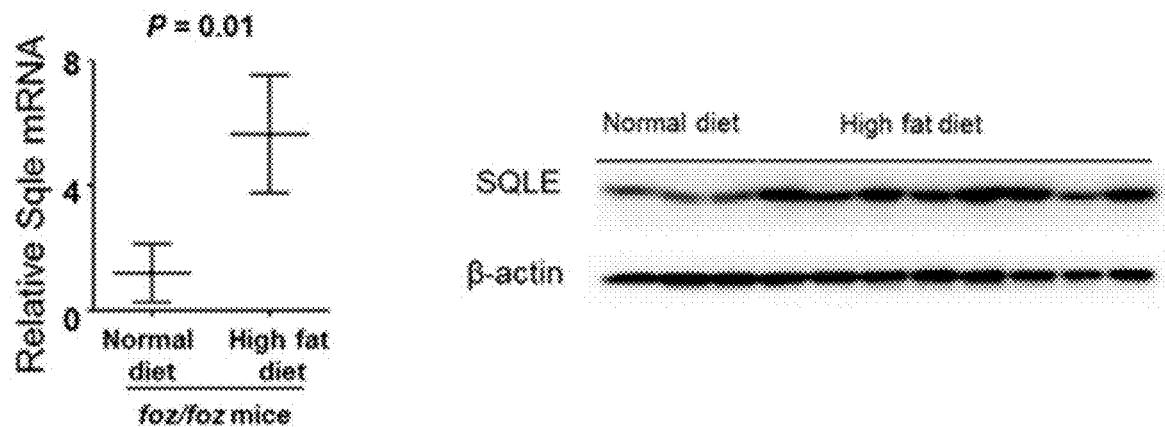

SQLE mRNA expression in NAFLD patients was determined by quantitative RT-PCR. SQLE mRNA was up-regulated in NAFLD patients (N=23) as compared to healthy normal controls (N=16) (FIG. 1A). mRNA expression of SQLE in two independent NAFLD cohorts (GSE89632 and GSE48452) was also analyzed. SQLE was highly up-regulated in patients with simple steatosis and NASH as compared with healthy people (FIG. 1B). Next, it was further demonstrated that mRNA and protein level of SQLE was overexpressed in a high-fat diet induced model of NAFLD in mice (FIG. 1C).

Serum SQLE is a Biomarker for Patients with NASH

Figure 2A:
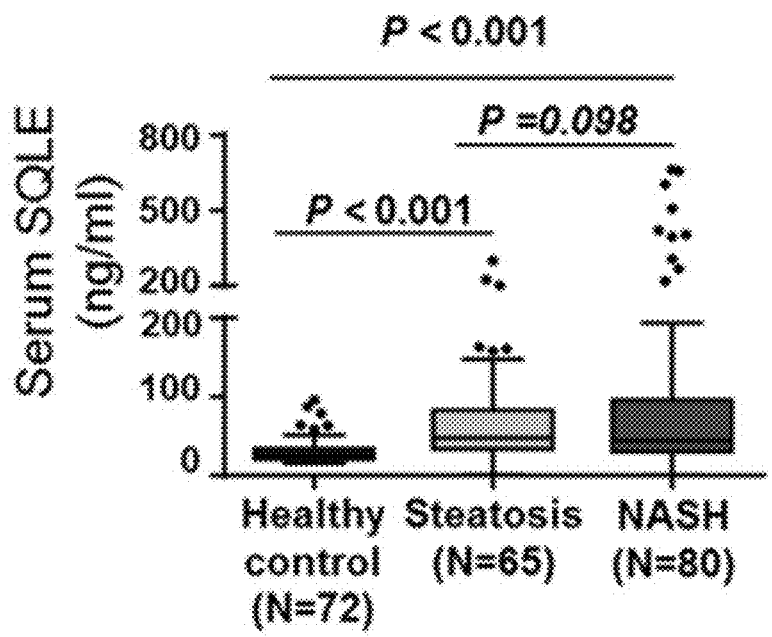
FIGS. 2A-2B: Serum SQLE level is a biomarker for patients with NASH in an embodiment.
Figure 2B:
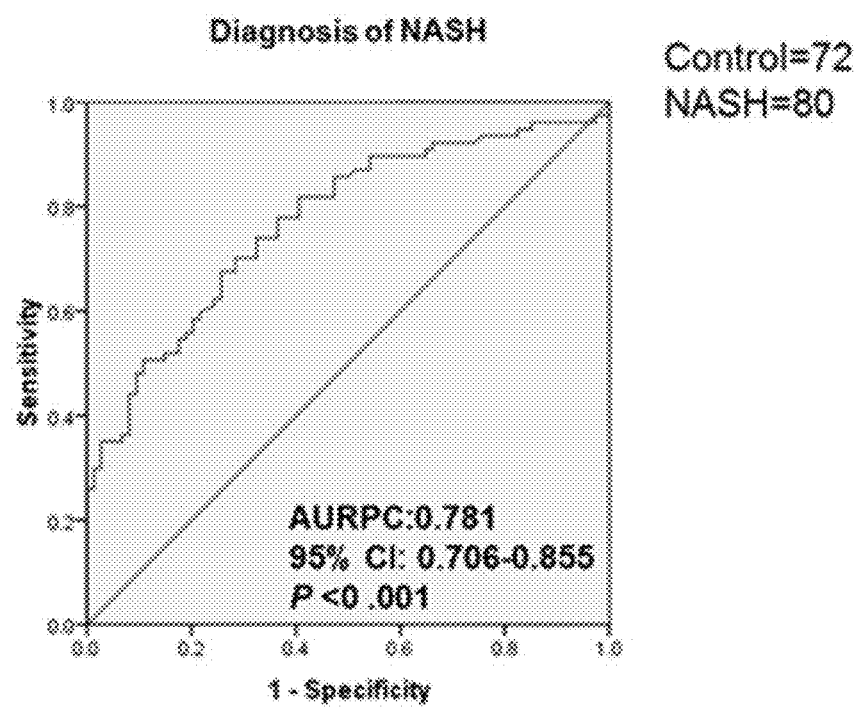

The clinical impact of SQLE in patients with NASH was investigated by detecting the serum level of SQLE using ELISA. A prospective cohort of 217 subjects was enrolled onto this study, which included 72 control subjects without fatty liver measured by proton-magnetic resonance spectroscopy and 145 age- and sex-matched NAFLD patients, 80 of them diagnosed with NASH (Table 2). As shown in FIG. 2A, serum SQLE level was significantly increased in patients with NAFLD as compared to healthy peoples. In patients with NAFLD, serum SQLE was significantly and positively correlated with body mass index (BMI) (r=0.249, P=0.000), steatosis (r=0.161, P=0.017), lobular inflammation (r=0.180, P=0.026), and fibrosis (r=0.161, P=0.048), the latter two of which are major histologic features of NASH (Table 3). Multivariate logistic regression analysis was performed and serum SQLE was identified as an independent risk factor for steatosis and steatohepatitis patients in all subjects (odds ratio 0.952, 95% confidence interval 0.917-0.988, P=0.009) after the adjustment for potential confounding factors, including BMI, ALT and fasting glucose (Table 4). To evaluate the utility of serum SQLE as a biomarker in the diagnosis of NASH, a receiver operating characteristic (ROC) curve was constructed. Serum SQLE levels exhibited a high overall accuracy in discriminating NASH subjects from control subjects with the area under the receiver operating characteristic curve (AUROC) of 0.781 (95% CI: 0.706-0.855) (FIG. 2B). Thus, serum SQLE can be a novel biomarker for the clinical diagnosis of NASH.

Figure 3A:
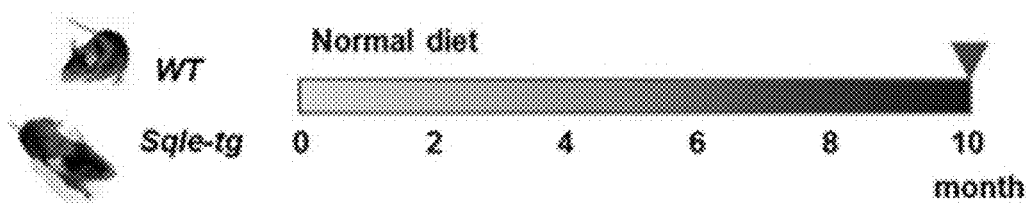
FIGS. 3A-3H: Hepatocyte-specific overexpression of SQLE induces spontaneous liver steatosis, liver injury and insulin resistance in an embodiment.
Figure 3B:
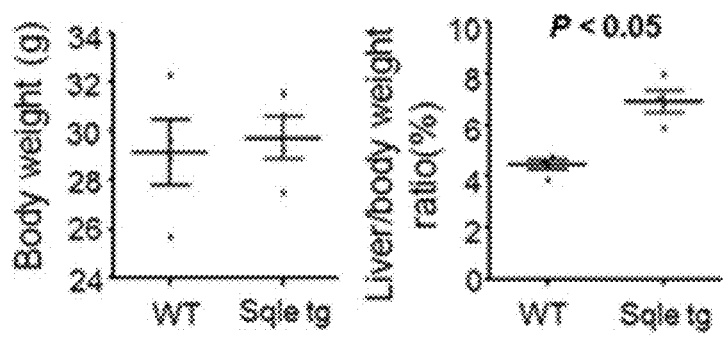
Figure 3C:
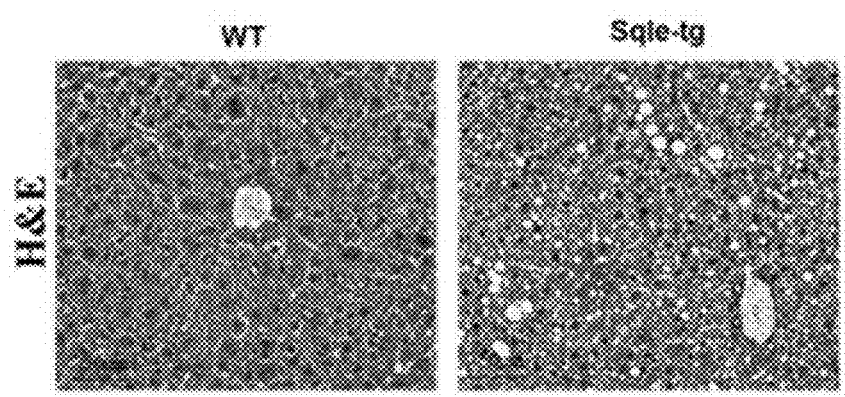
Figure 3D:
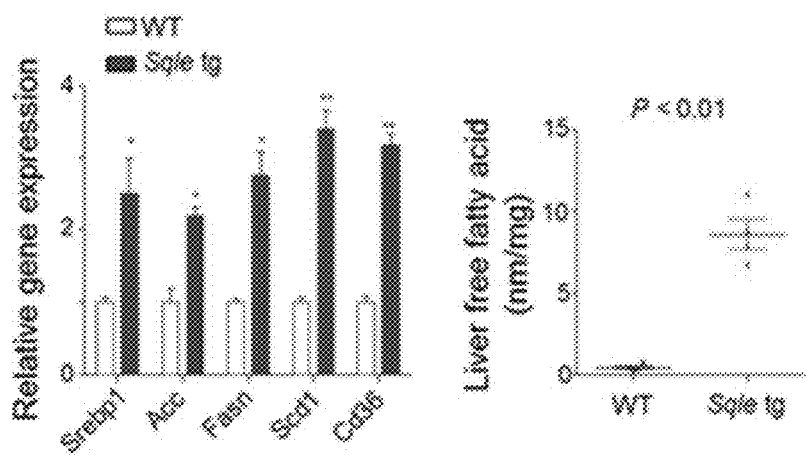

Hepatocyte-Specific Sqle Overexpression Activate De Novo Lipogenesis and Trigger Spontaneous Liver Steatosis, Liver Injury and Insulin Resistance To determine whether SQLE plays a role in the pathogenesis of NAFLD, Sqle-transgenic mice were constructed. Sqle tg mice were fed with normal chow for 10 months, after which they were sacrificed for analysis (FIG. 3A). It was observed that Sqle tg mice had higher liver weight-to-body weight ratio compared to wild-type mice, while the body weight remained largely unaffected (FIG. 3B). Thus, histopathological analysis was performed of the livers from Sqle tg mice. H&E staining showed that Sqle mice had increased hepatic lipid accumulation (FIG. 3C). qPCR and liver free fatty acid assay further confirmed that hepatocyte-specific Sqle overexpression activate Srebp1c induced de novo lipogenesis and free fatty acid accumulation in liver (FIG. 3D).

Figure 3E:
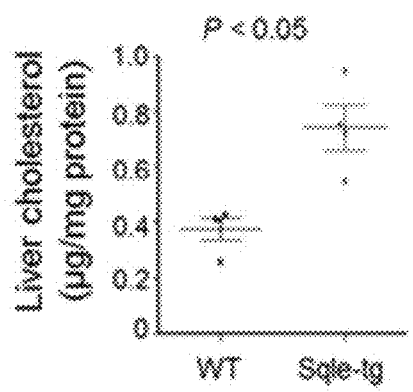
Figure 3F:
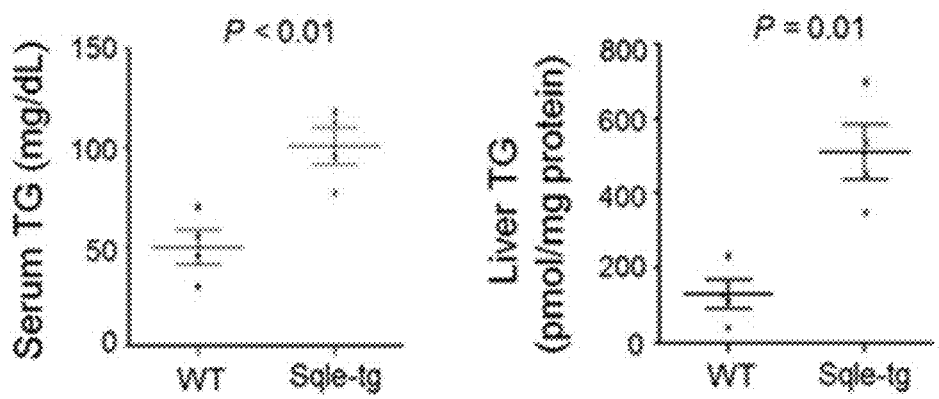
Figure 3G:
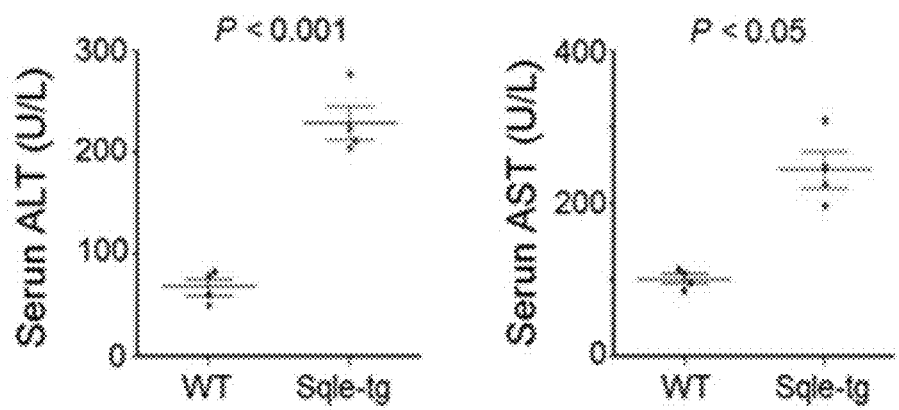
Figure 3H:
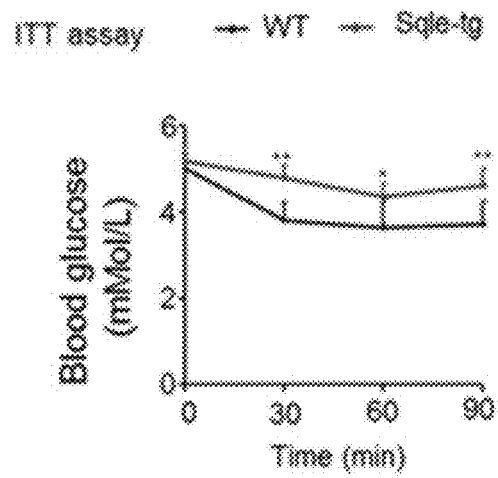

Together with this, the concentrations of serum and liver cholesterol or triglyceride (TG) were pronouncedly exacerbated in Sqle tg mice (FIGS. 3E and 3F). Increased levels of serum aspartate transaminase (AST) and alanine transaminase (ALT) indicated that Sqle overexpression in the liver triggered liver injury (FIG. 3G). Moreover, insulin tolerance tests (ITTs) revealed that insulin resistance was markedly exacerbated by Sqle overexpression in mice (FIG. 3I1). Taken together, hepatocyte-specific Sqle transgenic expression in mice resulted in a spontaneous phenotype that is consistent with the clinical manifestations of NAFLD and the metabolic syndrome.

Figure 4A:
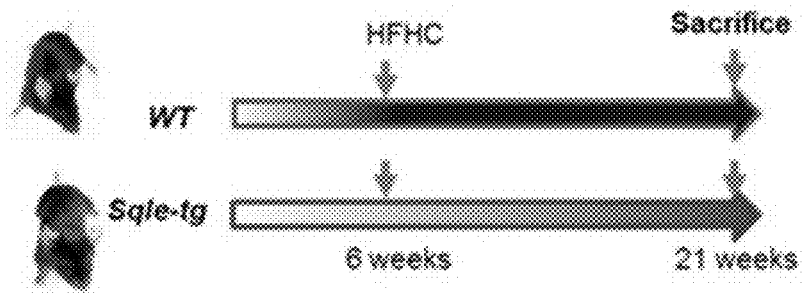
Figure 4B:
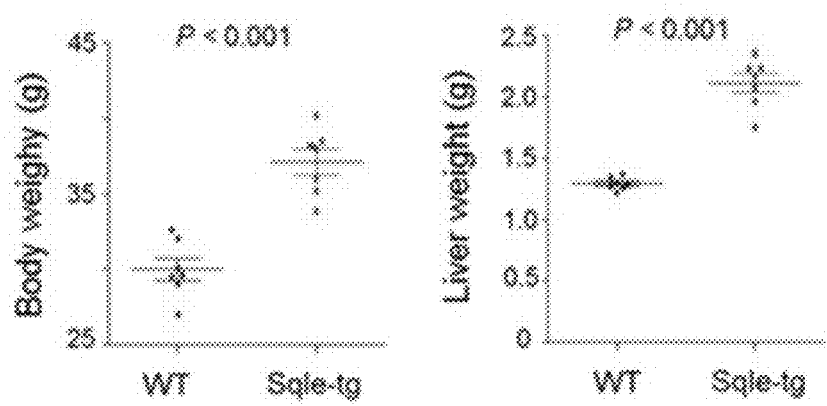
Figure 4C:
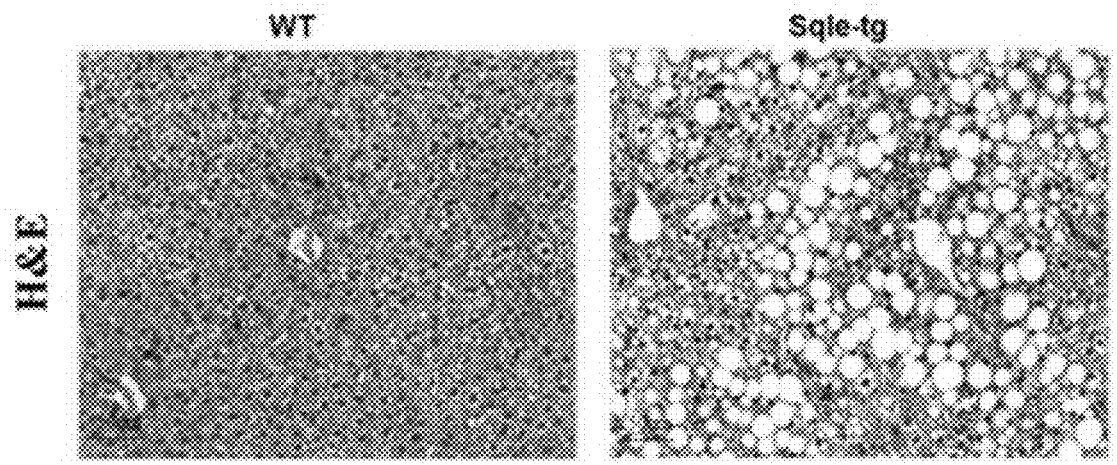
Figure 4D:
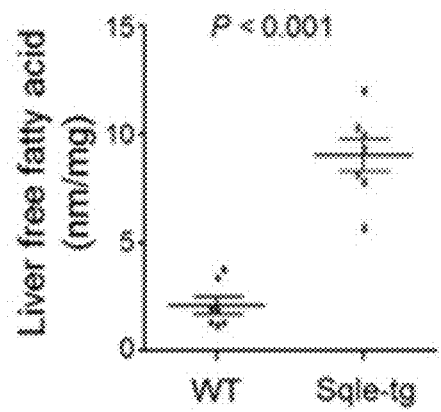
Figure 4E:
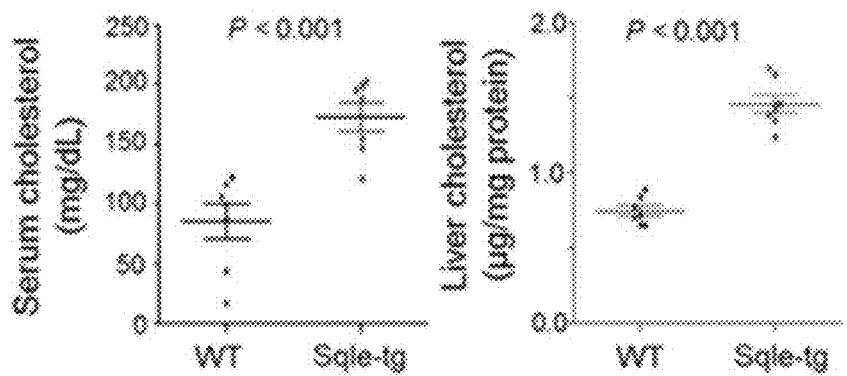
Figure 4F:
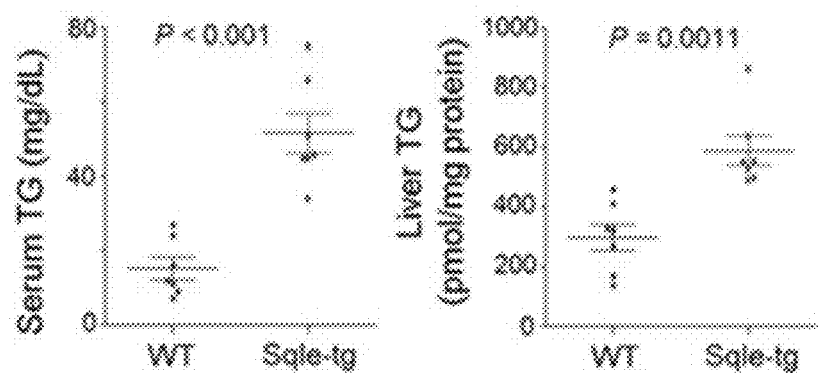
Figure 4G:
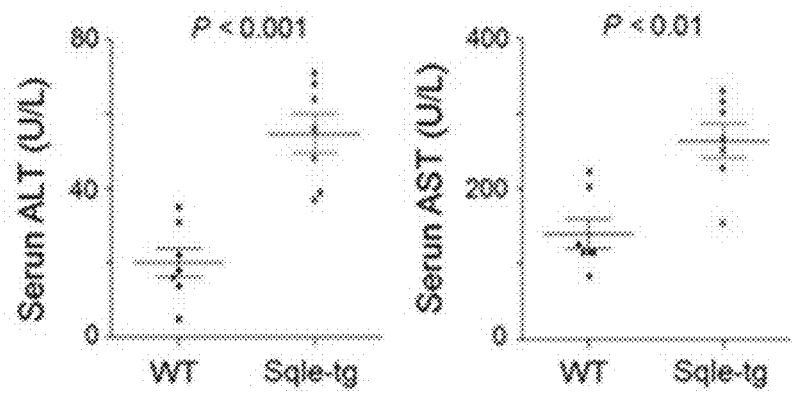
Figure 4G:
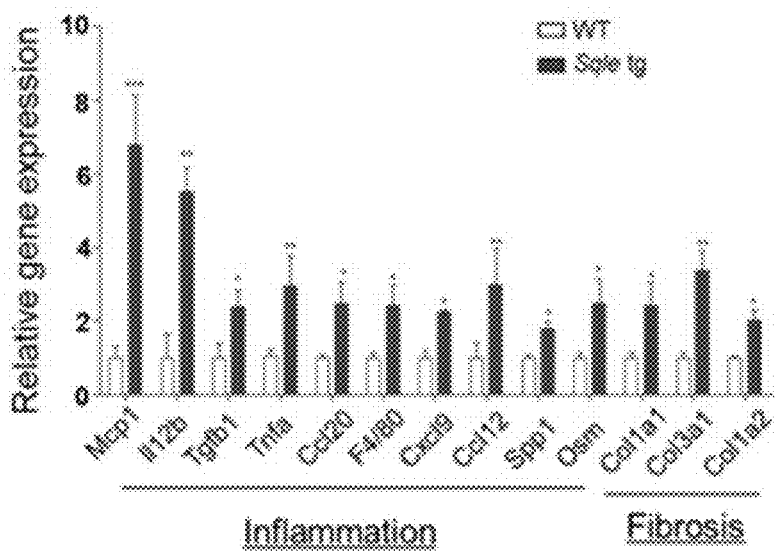
Figure 4I:
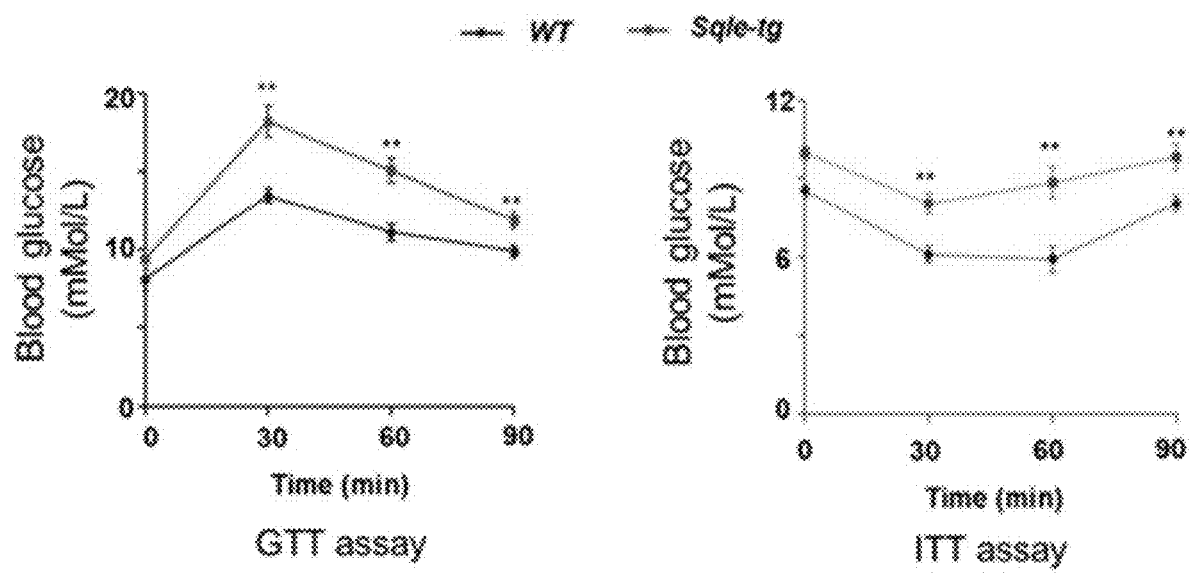

Hepatocyte-Specific Sqle Overexpression Exacerbated High Fat High Cholesterol Induced Liver Steatosis, Liver Injury, Inflammation and Insulin Resistance To validate the function of SQLE in NASH, Sqle tg mice and wild-type mice were fed with high fat high cholesterol diet for 15 weeks (FIG. 4A). In agreement with the findings above, Sqle tg mice demonstrated a significant increase in body weight and liver weight compared to wild type mice (FIG. 4B). Sqle tg mice also showed increased lipid accumulation in hepatocytes (H&E staining) (FIG. 4C). Free fatty acid assay further confirmed the increased liver lipid accumulation in HFHC fed Sqle tg mice (FIG. 4D). Serum and liver cholesterol (FIG. 4E), serum and liver triglyceride (FIG. 4F), serum ALT and AST level (FIG. 4G) all significantly increased in hepatocyte Sqle overexpression mice compared to wild-type mice. Compared to WT mice, Sqle overexpression also led to a considerable inflammatory and fibrosis response, which confirmed by increased mRNA expression of inflammation and fibrosis mediators, including Mcp-1, Il12β, Tgfβ1, Tnfα, Ccl-20, F4/80, Cxcl-9, Ccl-12, Spp1, Osm, Col1α1, Col1α2 and Col3α1(FIG. 4H). ITTs and glucose tolerance tests (GTTs) revealed marked elevation of insulin resistance in high fat high cholesterol fed Sqle tg mice (FIG. 4I). Collectively, these data demonstrate that SQLE overexpression exacerbates HFHC diet-induced NASH by inducing liver steatosis, inflammation and insulin resistance.

SQLE Inhibitor Terbinafine Suppresses NASH Development in HFHC-Fed Sqle Tg Mice

Figure 5A:
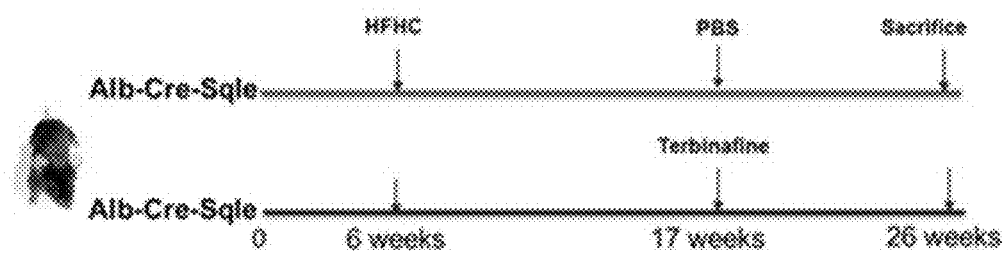
FIGS. 5A-5J SQLE inhibitor terbinafine suppresses NASH development in HFHC-fed Sqle tg mice in an embodiment.
Figure 5B:
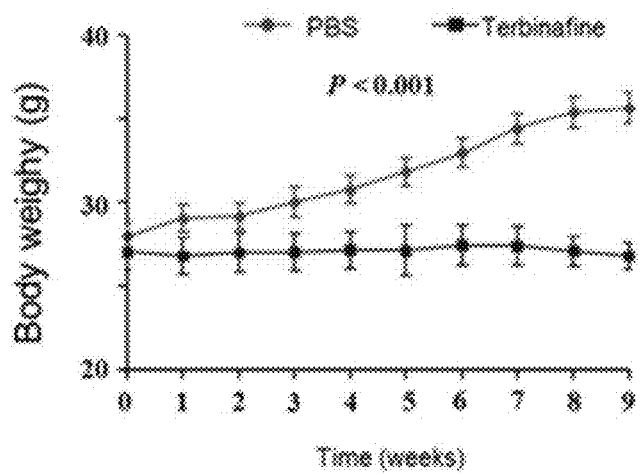
Figure 5C:
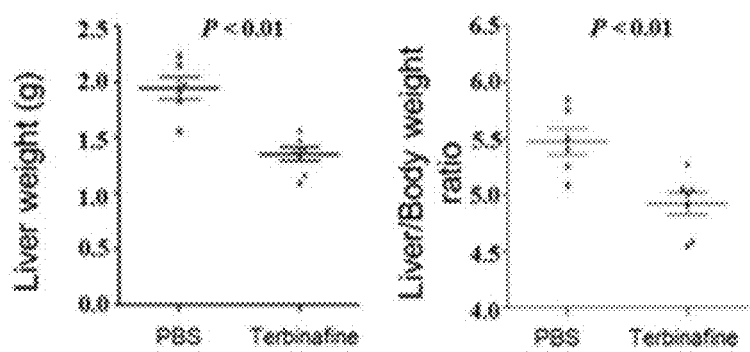
Figure 5D:
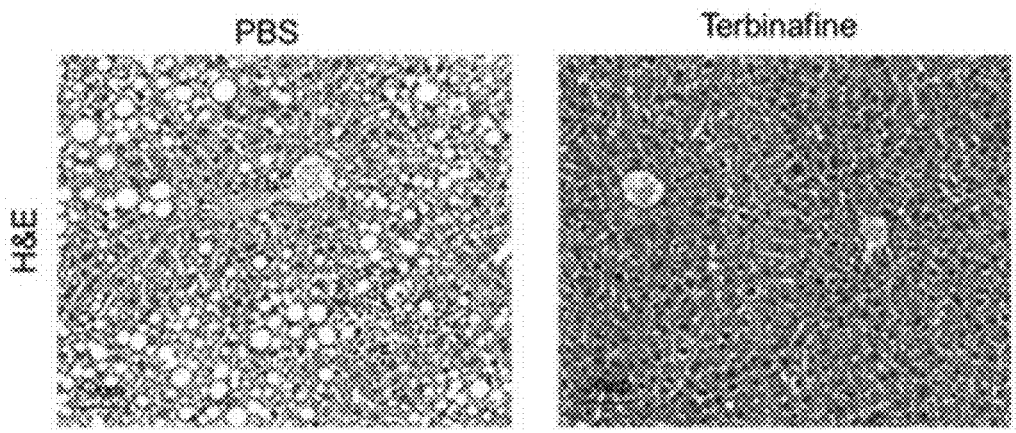
Figure 5E:
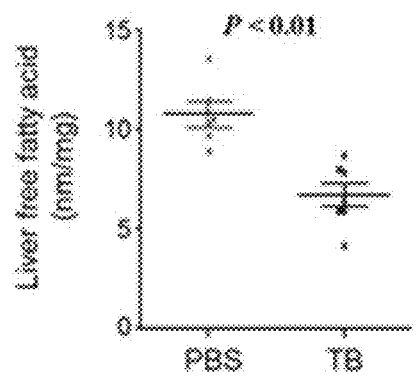
Figure 5F:
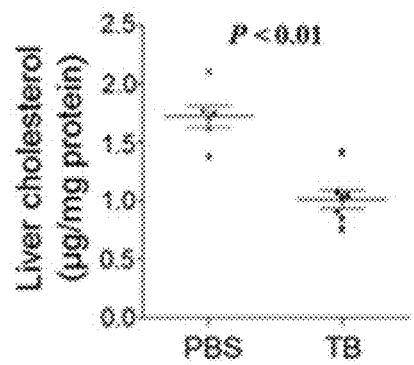
Figure 5G:
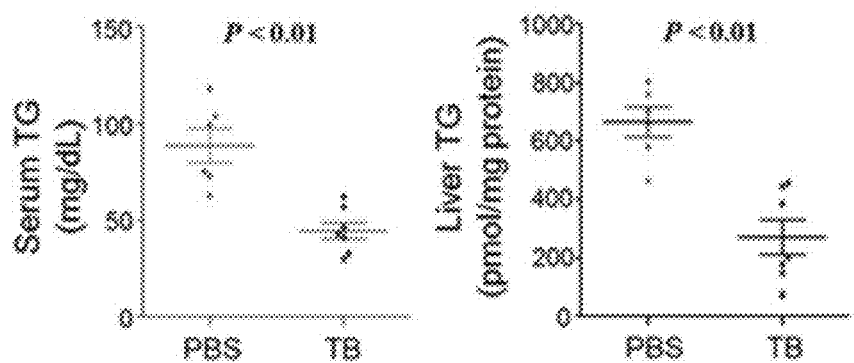
Figure 5H:
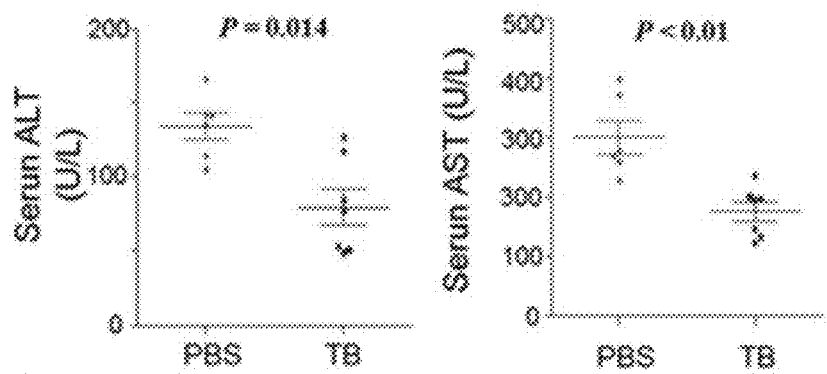
Figure 5I:
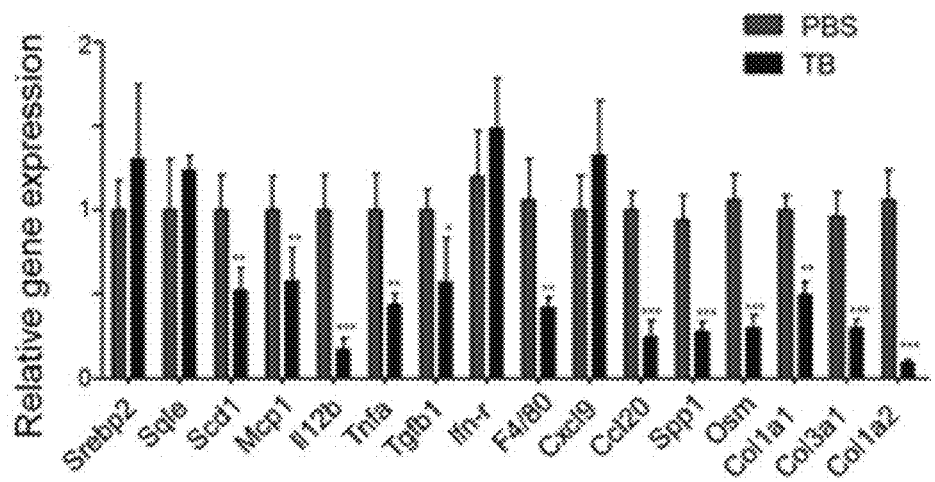
Figure 5J:
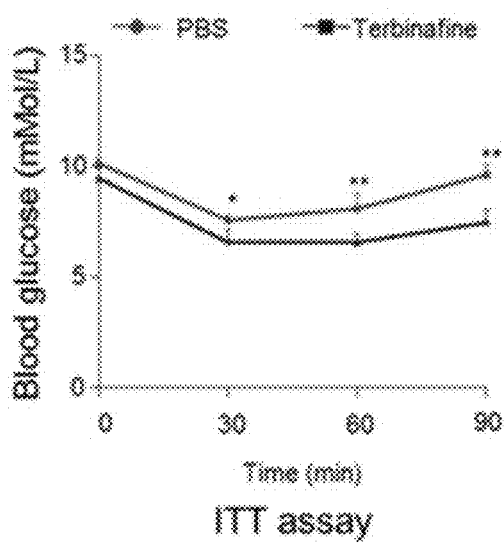

Efficacy of terbinafine was further validated in Sqle tg mice fed with a HFHC diet (FIG. 5A). Terbinafine treatment significantly attenuated body weight gain (FIG. 5B), liver weight and liver/body weight ratio (FIG. 5C). H&E staining of livers from PBS control and terbinafine-treated mice confirmed the reduction in steatohepatitis by terbinafine (FIG. 5D). Furthermore, terbinafine treatment significantly decreased Sqle tg mice liver free fatty acid accumulation (FIG. 5E), liver cholesterol level (FIG. 5F), serum and liver triglyceride (FIG. 5G), serum ALT and AST level (FIG. 5H). In parallel, terbinafine also reduced liver inflammation and fibrosis level which was confirmed by decreased mRNA expression of inflammation and fibrosis mediators (FIG. 5I). ITTs revealed markedly improved insulin sensitivity in terbinafine-treated mice (FIG. 5J). Collectively, these data indicate that terbinafine, by specifically inhibiting SQLE, suppressed NAFLD development in Sqle tg mice. These data indicate that hepatocyte SQLE can be seen as a novel therapeutic target in NASH.

SQLE Inhibitor Terbinafine Suppresses HFHC-Induced NAFLD

Figure 6A:
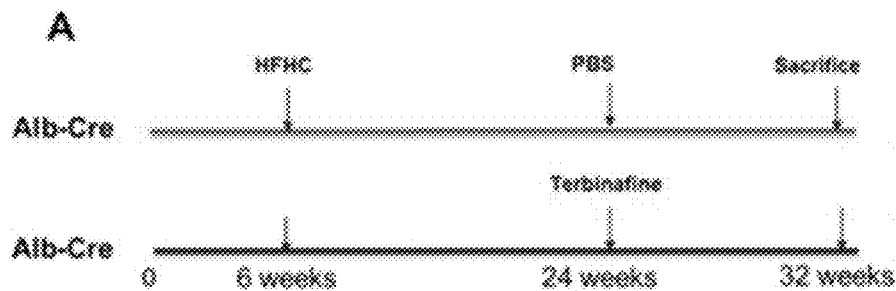
FIGS. 6A-6E SQLE inhibitor terbinafine suppresses HFHC diet induced NAFLD in an embodiment.
Figure 6B:
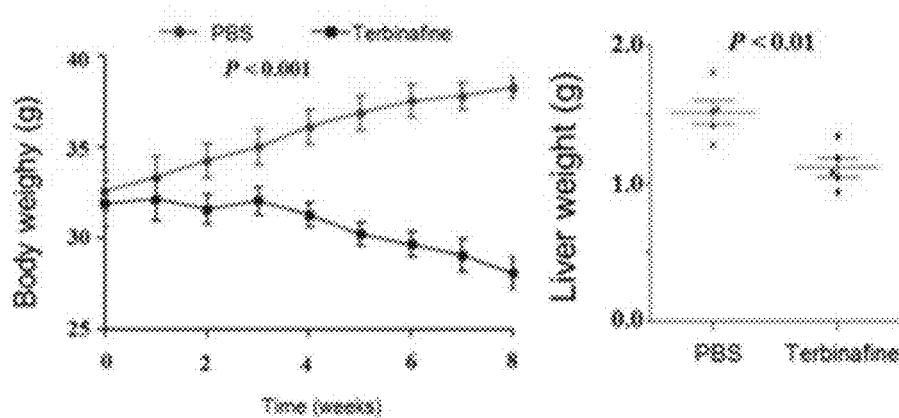
Figure 6C:
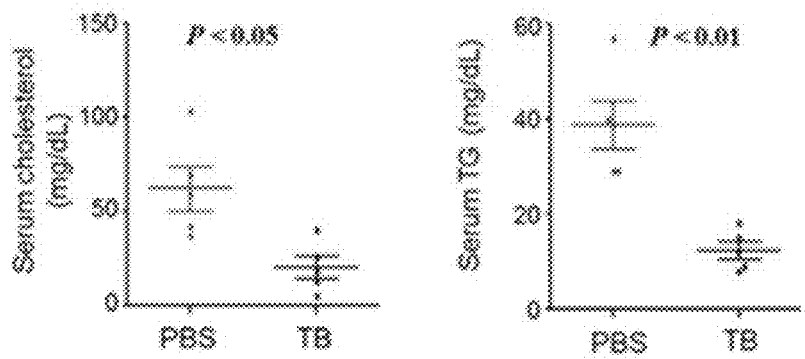
Figure 6D:
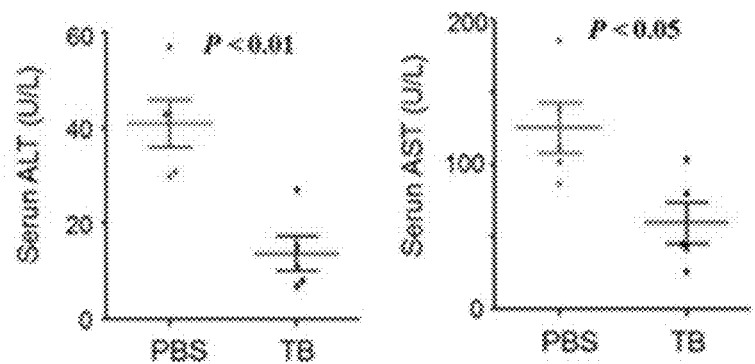
Figure 6E:
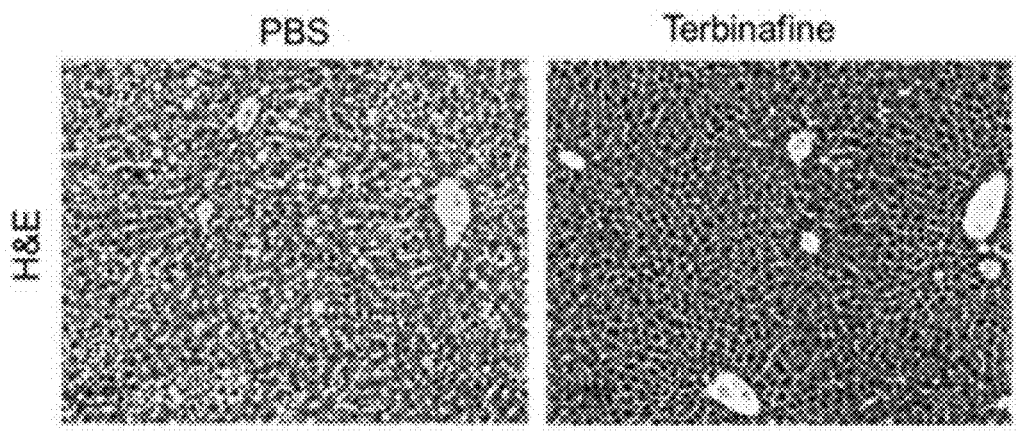
Figure 6F:
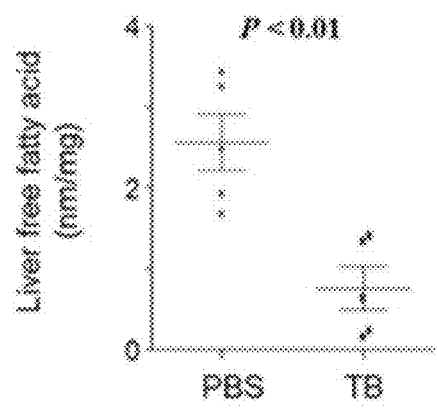
(FIG. 6F) Terbinafine suppresses liver steatosis was further confirmed by liver free fatty acid analysis.

It was also examined whether terbinafine was able to inhibit the development of HFHC-induced NAFLD (FIG. 6A). In line with the observations in the Sqle tg mice model, terbinafine treatment significantly decrease body weight, liver weight in the HFHC-fed WT mice (FIG. 6B). Terbinafine also attenuated HFHC-induced serum cholesterol, serum triglyceride (FIG. 6C), serum ALT and AST level (FIG. 6D). H&E staining (FIG. 6E) and free fatty acid assay (FIG. 6F) further confirm a reduction in liver steatosis by terbinafine. Therefore, these findings support terbinafine as a potential therapeutic drug candidate for the diet-induced NAFLD.

SQLE is Overexpressed in NAFLD-HCC Tissues

Figure 7A:
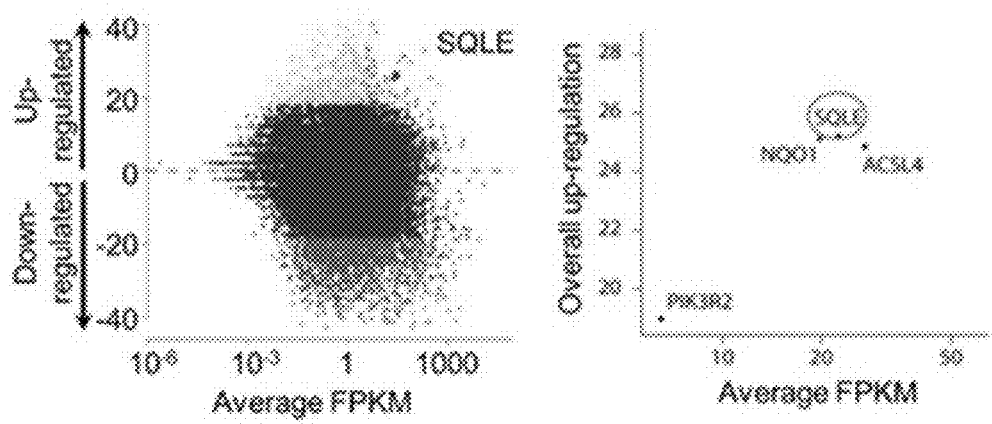
FIGS. 7A-7F SQLE expression in paired NAFLD-HCC tissues and adjacent normal liver tissues in an embodiment.
Figure 7B:
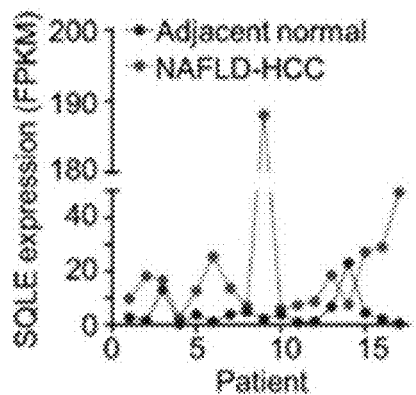
Figure 7C:
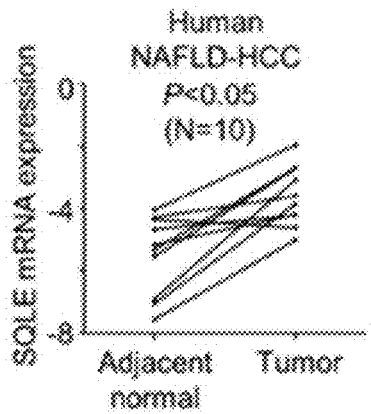
Figure 7D:
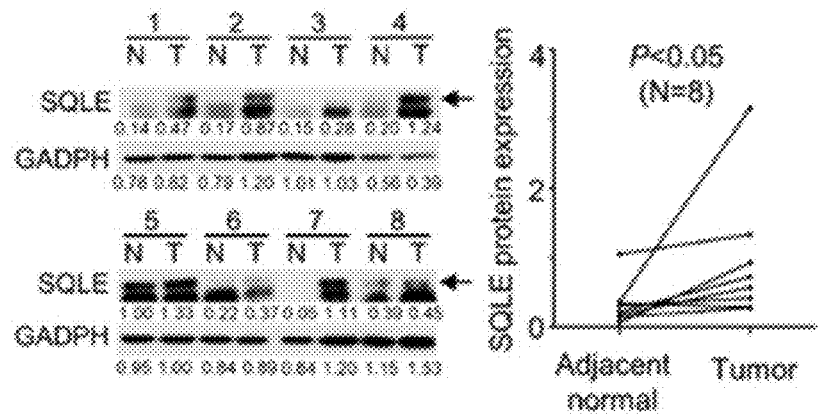
Figure 7E:
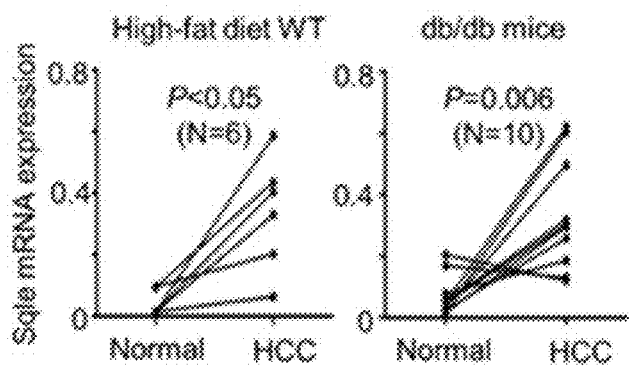
Figure 7F:
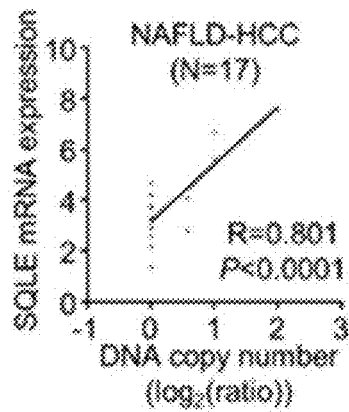

RNAseq analysis of 17 paired NAFLD-HCC tumor and adjacent normal tissues was performed. Reactome analysis of differentially expressed genes showed that metabolism is a key pathway altered in NAFLD-HCC. Among up-regulated metabolic genes, SQLE was a top outlier gene and it was overexpressed in 16 out of 17 paired NAFLD-HCC samples (FIG. 7A, 7B) with 25.2-fold higher. The up-regulation of SQLE mRNA was validated in an independent cohort of 10 paired NAFLD-HCC samples (FIG. 7C). SQLE protein was also elevated in NAFLD-HCC (FIG. 7D). Next, the expression of Sqle in two obesity-associated NAFLD-HCC mouse models was next determined. Sqle was up-regulated in all HCC tumors (6/6) from N,N-diethylnitrosamine (DEN) and high-fat, high-cholesterol (HFHC) diet treated C57BL/6 mice (FIG. 7E). Similarly, Sqle was up-regulated in 8 out of 10 HCC tumors from DEN-treated db/db mice (FIG. 7E). SQLE is therefore commonly overexpressed in human NAFLD-HCC and experimental NAFLD-HCC mouse models. In addition, it was observed that the copy number amplification of SQLE was positively correlated with its mRNA expression in human NAFLD-HCC (FIG. 7F), indicating that copy number gain contributes to up-regulation of SQLE.

Figure 8A:
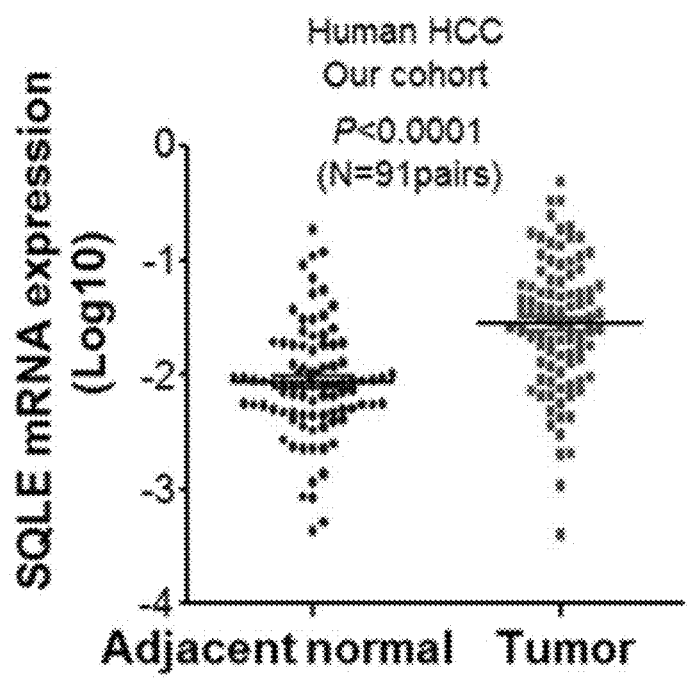
FIGS. 8A-8C SQLE expression in paired HCC tissues and adjacent normal liver tissues in an embodiment.
Figure 8B:
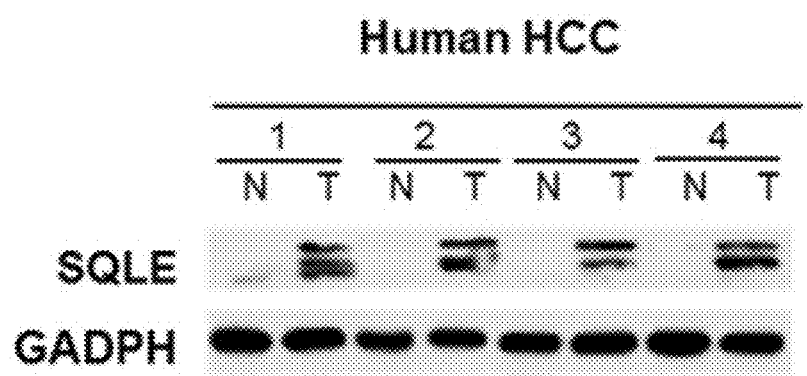
Figure 8C:
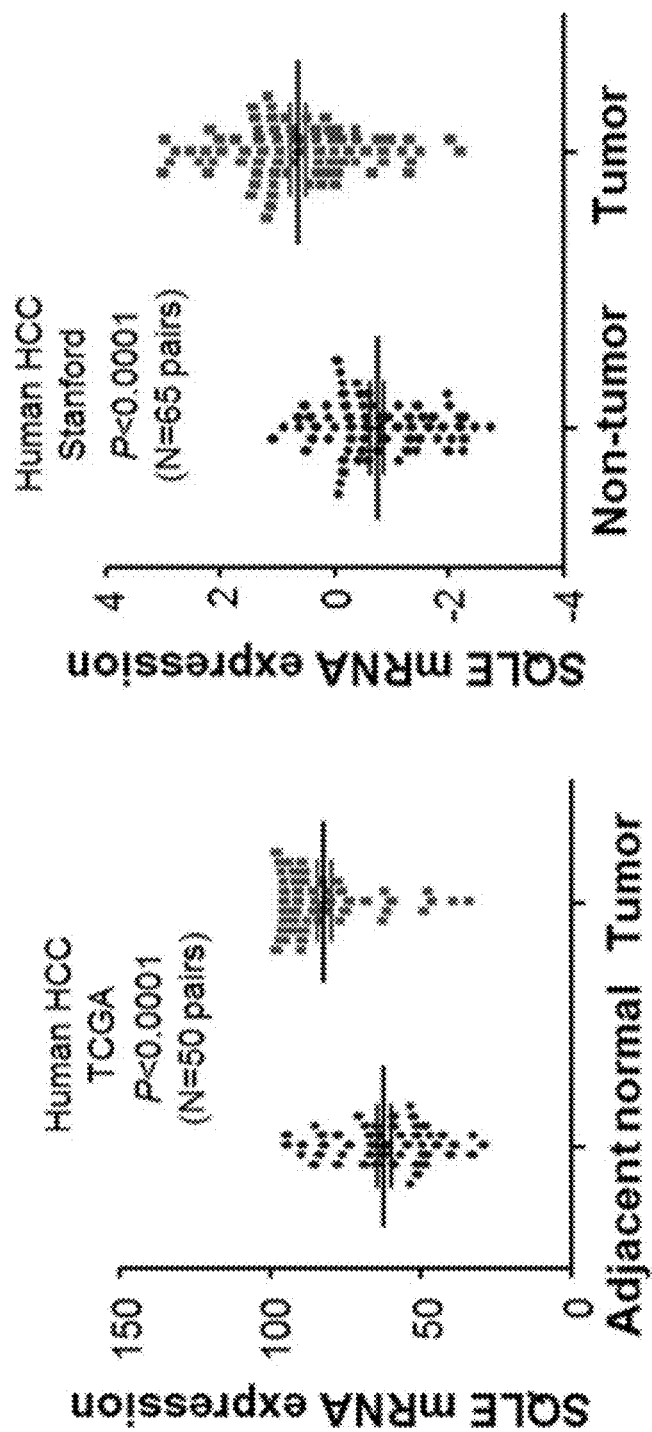

SQLE is Overexpressed in HCC Tissues mRNA expression of SQLE was analyzed in three independent HCC cohorts (CUHK cohort, TCGA and Stanford). SQLE was highly up-regulated in primary HCC as compared with their adjacent normal tissues (N=91, P<0.0001) as determined by qPCR (FIG. 8A), and its overexpression was validated in the TCGA (N=50; P<0.0001) and Stanford cohorts (N=65; P<0.0001) (FIG. 8C). Western blot also confirmed that SQLE was up-regulated in HCC tumor compared with adjacent normal tissues (FIG. 8B).

SQLE Expression is Associated with Poor Survival of HCC Patients

Figure 9A:
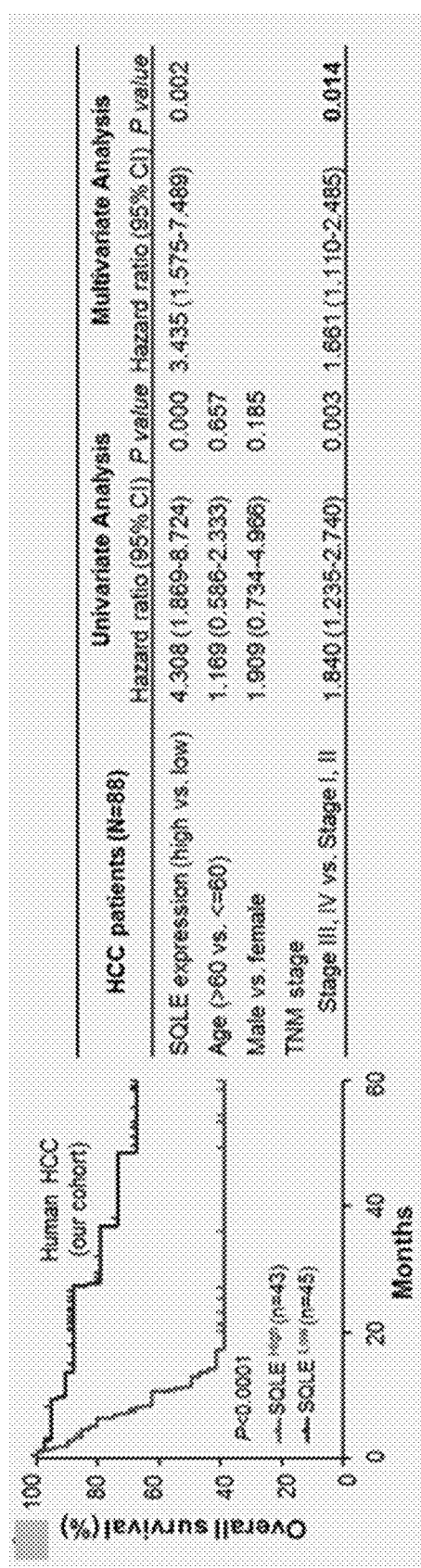
FIGS. 9A-9B SQLE overexpression is an independent prognostic factor that predicts poor survival in patients with HCC in an embodiment. (A) Kaplan-Meier survival analysis and Cox regression analysis of our Guangzhou cohort (high N=43, low N=45) HCC, (B) and TCGA-LIHC (high N=155, low N=175) cohorts based on predictive survival analysis.
Figure 9B:
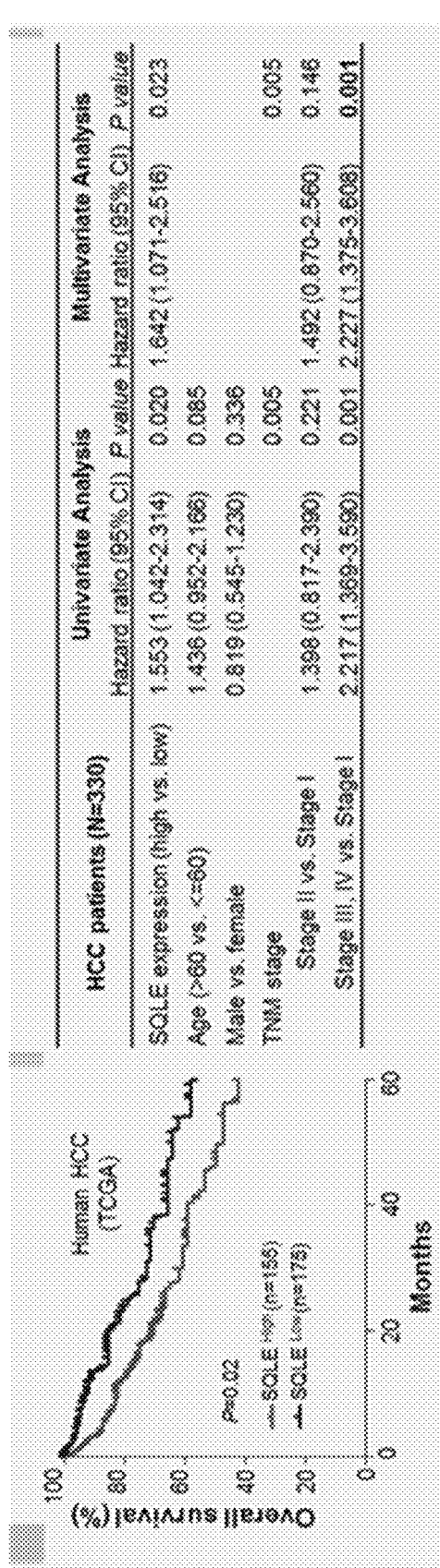

The clinical significance of SQLE in human HCC was then assessed. Multivariate COX proportional hazards regression analysis revealed that high SQLE expression was an independent prognostic factor that predicts poor disease-specific survival (P<0.0001; hazard ratio, 4.31; 95% CI, 1.87-8.72]) (FIG. 9A and Table 5). The prognostic significance of SQLE in TCGA cohort was validated (N=330). Kaplan-Meier curve showed that SQLE mRNA was associated with poor survival in HCC patients (P=0.02) and was an independent prognostic factor (P=0.02; hazard ratio, 1.553; 95% CI, 1.042-2.314]) (FIG. 9B and Table 6). These data indicate that SQLE expression is associated with poor prognosis in HCC.2.4 Hepatocyte-specific transgenic SQLE expression in mice accelerates NAFLD-HCC formation.

Figure 10A:
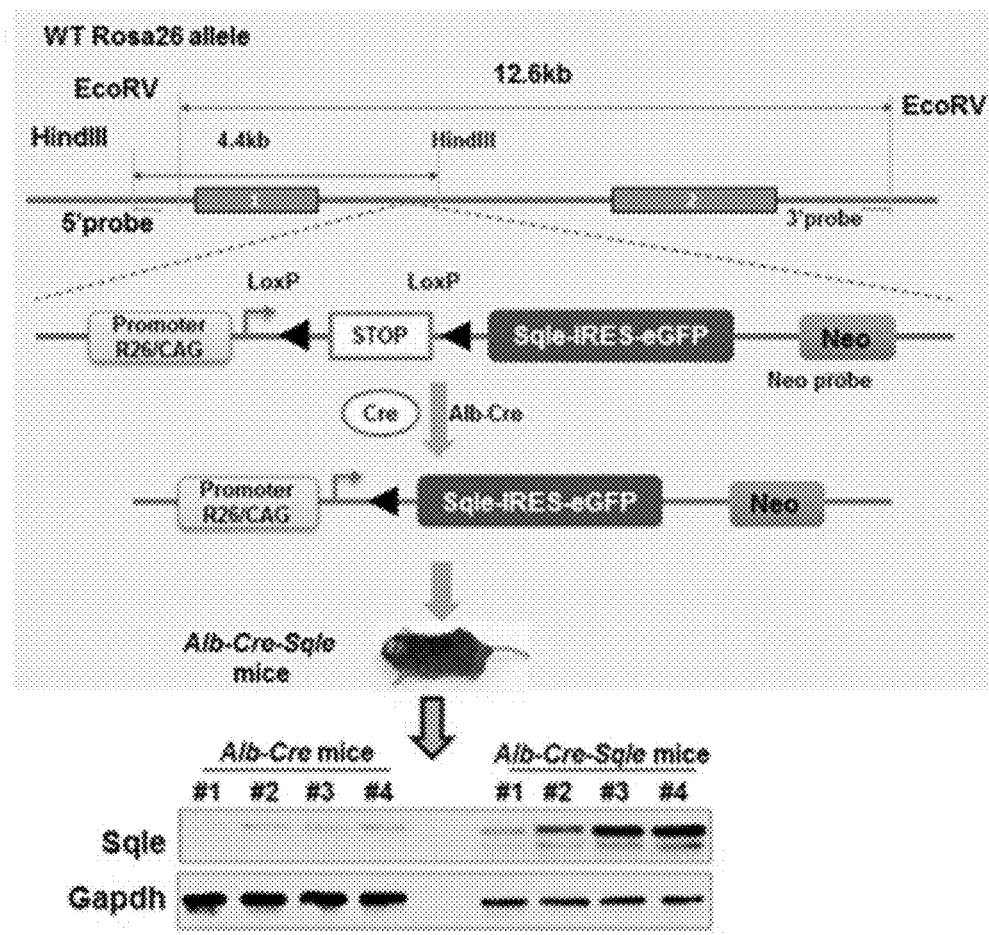
FIG. 10: Hepatocyte-specific overexpression of SQLE accelerates high-fat and high-cholesterol (HFHC) diet associated NAFLD-HCC in an embodiment. (A) Scheme for the generation of hepatocyte-specific Sqle overexpressing mice. Western blot confirmed overexpression of Sqle in the livers of Sqle tg mice. (B) Experimental design of DEN-injected and HFHC diet mice model of NAFLD-HCC (upper). H&E staining of wild-type and Sqle tg mice livers (middle). HCC tumor incidence and multiplicities in wild-type and Sqle tg mice (lower). Results are mean±SEM (N=9-10). (C) Hepatocyte-specific Sqle expression increased liver weight (middle) and liver/body weight ratio (right), but not body weight (left), in DEN-injected HFHC diet treated mice. (D) Serum AFP (left), ALT (middle), and AST (right) levels of wild-type and Sqle tg mice treated with DEN and HFHC diet. Results are mean±SEM (N=9-10). (E) Ki67 staining of livers from DEN-injected and high-fat high-cholesterol diet treated wild-type and Sqle tg mice. T, tumor, N, adjacent normal. Results are mean±SEM (N=9-10). Mann-Whitney U test was used. Scale bars, 50 ***P<0.001.
Figure 10B:
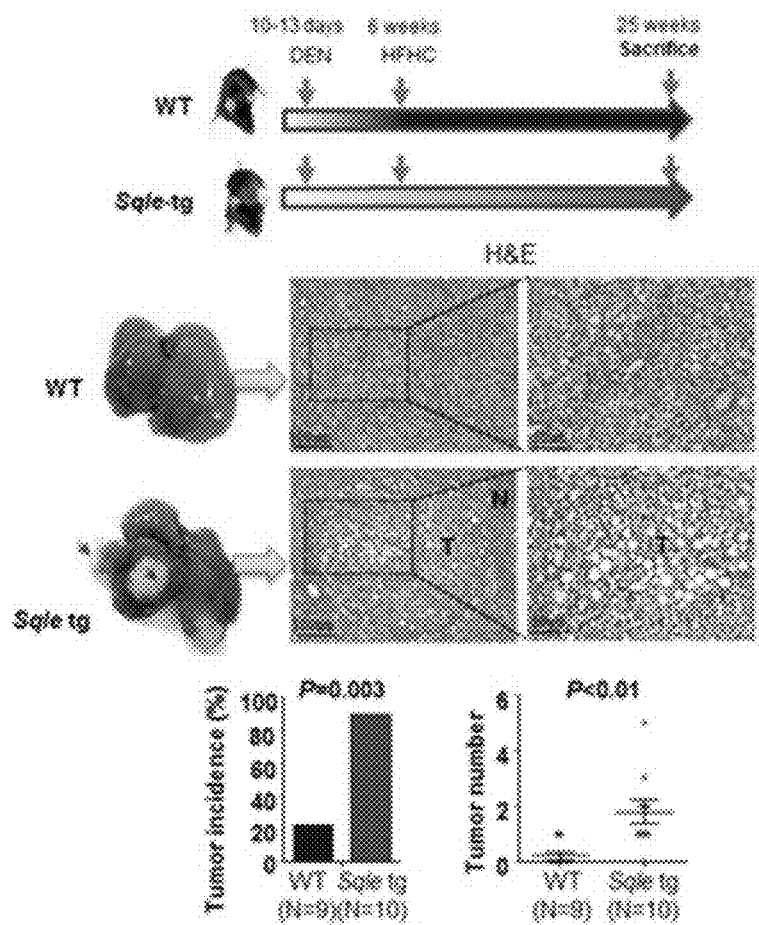
Figure 10C:
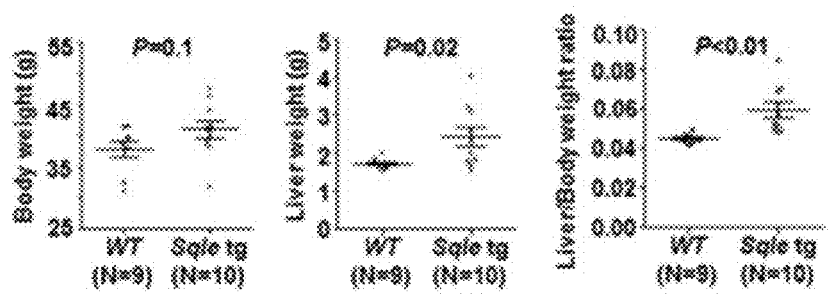

Hepatocyte-Specific Transgenic SQLE Expression in Mice Accelerates NAFLD-HCC Formation To determine the relevance of SQLE in NAFLD-HCC development in vivo, Sqle conditional transgenic (Sqle-tg) mice were constructed. Crossing Sqle tg mice to Albumin-Cre mice leads to hepatocyte-specific Sqle expression (FIG. 10A). To evaluate the role of Sqle in NAFLD-HCC, wild-type and Sqle tg mice were injected with a single dose of DEN at day 13, followed by a HFHC diet for 20 weeks (FIG. 10B). At 25 weeks of age, mice were sacrificed and the liver was analyzed. Sqle-tg mice developed significant more tumors (9/10) as compare to wild-type mice (2/10) (P=0.003), and histological examination (H&E staining) confirmed HCC formation in the livers of Sqle tg mice, together with hallmarks of fatty liver disease such as hepatocyte ballooning and inflammatory cell infiltration (FIG. 10B). Sqle tg mice also showed increased liver weight and liver-to-body weight ratio but not body weight (FIG. 10C). Consistent with development of HCC, α-fetoprotein (AFP), a serum biomarker for liver cancer, was elevated in Sqle tg mice (FIG. 10D). Serum ALT and AST levels, markers for liver inflammation and injury were also significantly higher in Sqle tg mice (P<0.01) (FIG. 10D). Ki-67 staining was next performed to determine cell proliferation (FIG. 10E). Compared to wild-type mice liver tissues, non-tumorous liver tissues from Sqle tg mice had increased cell proliferation, while tumors derived from Sqle tg mice showed the highest Ki-67 scores (FIG. 10E). Collectively, these data demonstrate that SQLE overexpression exacerbates HFHC diet-induced NAFLD and promotes NAFLD-HCC formation in mice by inducing cell proliferation.

SQLE Inhibitor Terbinafine Suppresses NALFD-HCC Cell Lines Growth In Vitro

Figure 11A:
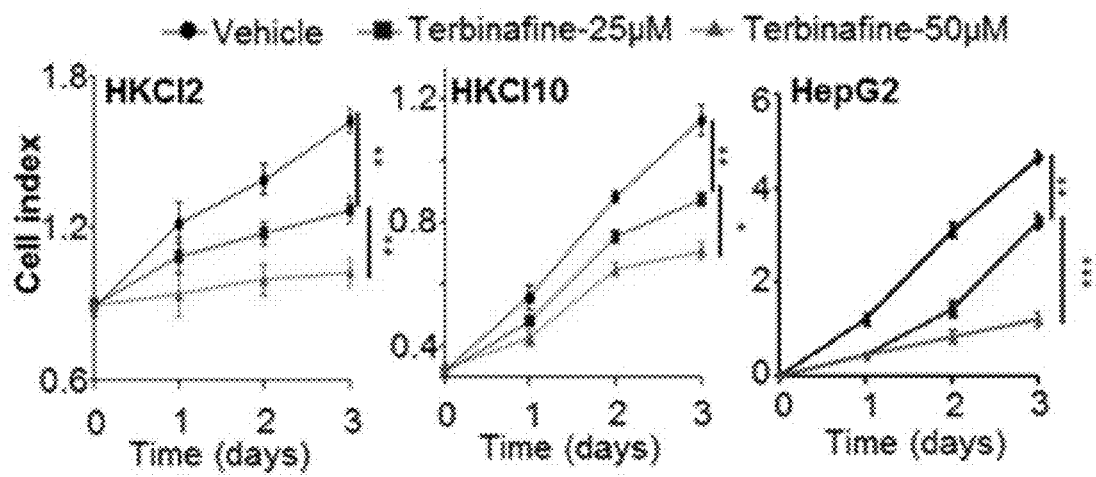
FIG. 11: SQLE inhibitor terbinafine suppresses NALFD-HCC cell lines proliferation, colony formation and cholesterol accumulation in an embodiment. Terbinafine treatment suppressed cell growth (A) and colony formation (B) in NAFLD-HCC (HKCI2, HKCI10) and HepG2 cell lines (N=3, performed in triplicates). (C) Terbinafine suppressed SQLE and PCNA expression was determined by Western blot (N=3, performed in triplicates). (D) Terbinafine reduced the levels of free cholesterol and cholesteryl ester in HCC cell lines (N=4, performed in triplicates). Data are represented as means±SEM. *P<0.05, P<0.01, *P<0.001.
Figure 11B:
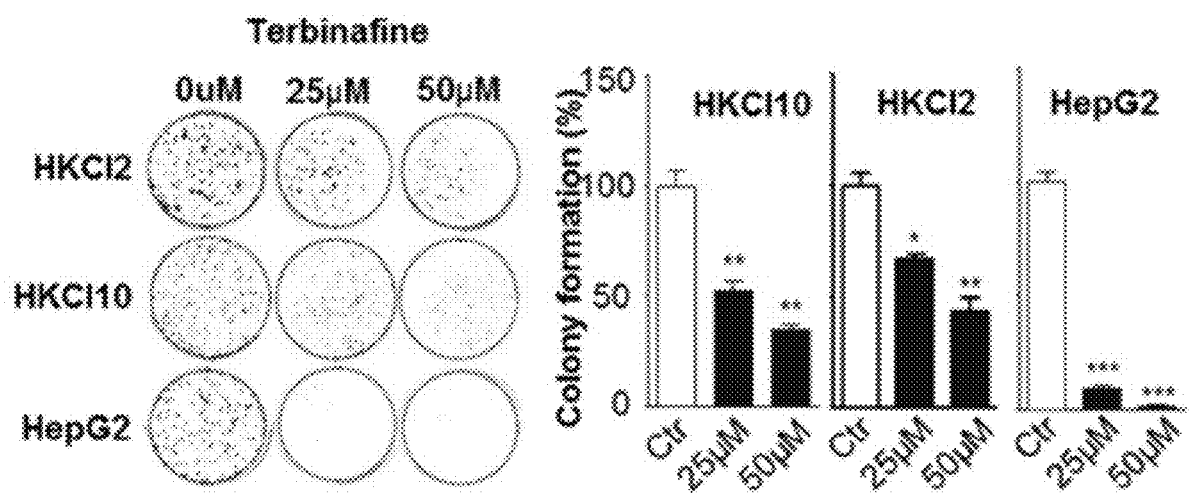
Figure 11C:
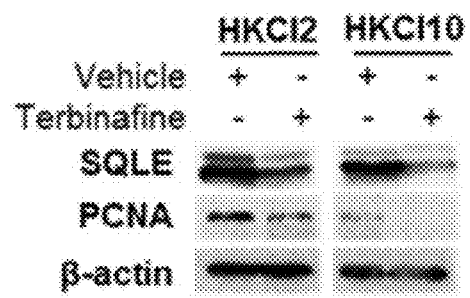
Figure 11D:
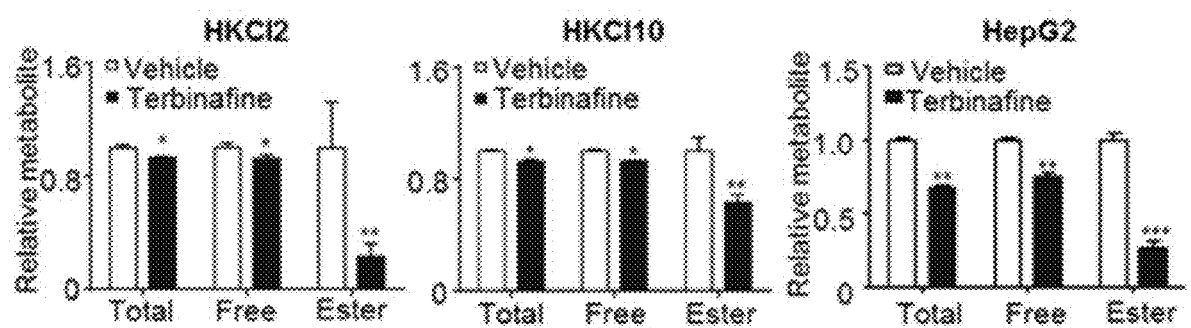

Given the important oncogenic role of SQLE in NAFLD-HCC, it was evaluated if a specific SQLE inhibitor, terbinafine (used widely to treat fungal infections in humans), can be repositioned for prevention or treatment of NAFLD-HCC. HKCI2, HKCI10, and HepG2 cells were treated with different doses of terbinafine. At 25 μM to 50 μM, terbinafine markedly suppressed HKCI2, HKCI10, and HepG2 cell lines proliferation as determined by cell growth and colony formation assays (FIGS. 11A and 11B). Western blot indicated that terbinafine suppressed SQLE and PCNA expression (FIG. 11C). Furthermore, terbinafine suppressed free cholesterol and cholesteryl ester levels (FIG. 11D).

SQLE Inhibitor Terbinafine Suppresses Liver Cancer Growth In Vivo

Efficacy of terbinafine in vivo was next evaluated. Terbinafine significantly suppressed growth of subcutaneous HepG2 xenografts (77.8%, P<0.01) (FIG. 12A1, 12A2). Survival of mice harboring HepG2 xenografts was also determined (tumor size 400 mm³ as cutoff), and it was found that terbinafine significantly prolonged the overall survival (P<0.01) (FIG. 12A3). Terbinafine also suppressed the growth of orthotopic HKCI2 xenografts (>85%, P<0.01) (FIG. 12B1, 12B2) both in terms of tumor size or tumor weight. In these xenograft models, tumor free cholesterol and cholesteryl ester levels were suppressed (FIG. 12C1, 12C2).

SQLE Inhibitor Terbinafine Suppresses NALFD-HCC Develop in Sqle Tg Mice

Figure 13D:
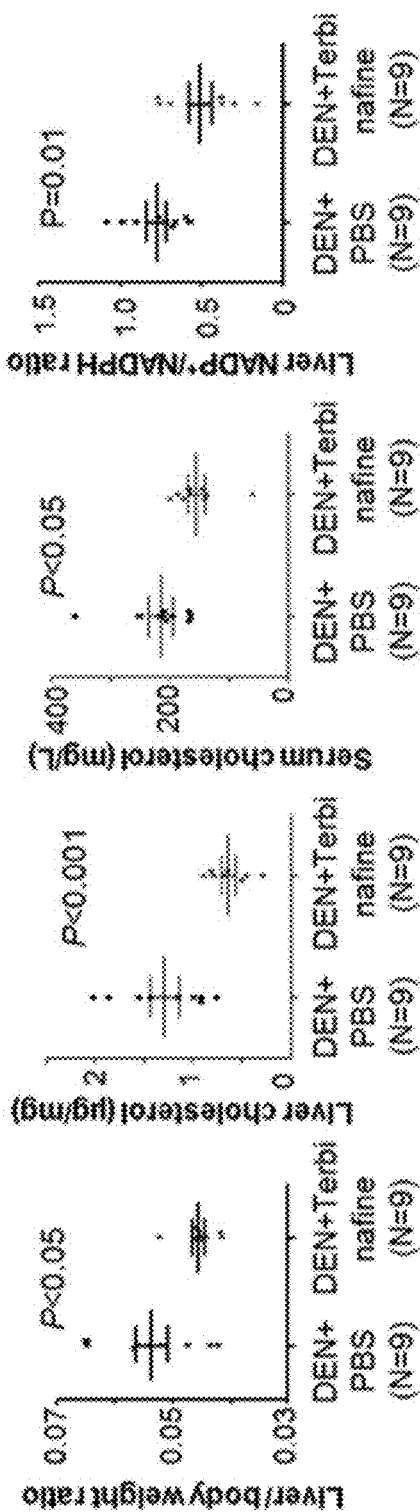
Figure 13E:
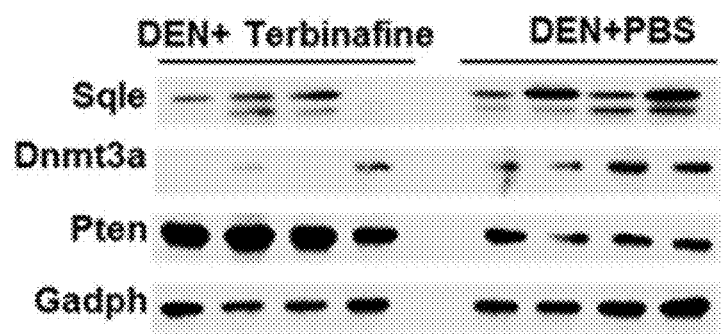

Further the efficacy of terbinafine was validated in Sqle tg mice injected with DEN and fed with a HFHC diet (FIG. 13A). Terbinafine treatment significantly reduced tumor incidence (4/9 mice in terbinafine group vs 8/9 mice in PBS, P<0.05) and tumor number (P<0.01) (FIGS. 13B1 and 13B3). H&E staining of livers from the vehicle and terbinafine-treated mice confirmed a reduction in HCC tumorigenesis and cell proliferation by terbinafine (FIG. 13C). Terbinafine decreased Sqle tg mice liver/body weight ratio, liver and serum cholesterol levels (FIG. 13D). In parallel, Terbinafine also inhibited NADPH oxidation, thereby reducing the $NADP^+/NADPH$ ratio (FIG. 13D). Moreover, terbinafine inhibited Sqle and Dnmt3a protein expression, but restored Pten expression in livers of Sqle tg mice (FIG. 13E). Collectively, these data indicate that terbinafine, by specifically inhibiting SQLE, suppressed the accumulation of liver cholesterol/cholesteryl ester and blocked the SQLE-ROS-DNMT3A-PTEN oncogenic axis, ultimately leading to inhibition of hepatocarcinogenesis. Importantly, terbinafine did not cause any liver injury or toxicity. Pharmacological inhibition of SQLE is hence a promising approach that is safe and effective for the prevention and treatment of NAFLD-HCC.

All patents, patent applications, and other publications, including GenBank Accession Numbers, cited in this application are incorporated by reference in the entirety for all purposes.

TABLE 1

Primers used in this study

| Purpose | Gene | Primer | Sequence |
|---|---|---|---|
| mRNA expression | SQLE | Forward | ATTCCCTTCTGAAAGGGCACCT (SEQ ID NO: 5) |
| | | Reverse | TTATTTAAAAATCGCCTGCTGGA (SEQ ID NO: 6) |
| | ACTIN | Forward | CATCCACGAAACTACCTTCAACTCC (SEQ ID NO: 7) |
| | | Reverse | GAGCCGCCGATCCACACG (SEQ ID NO: 8) |
| | Srebp1c | Forward | GGAGCCATGGATTGCACATT (SEQ ID NO: 9) |
| | | Reverse | GGCCCGGGAAGTCACTGT (SEQ ID NO: 10) |
| | Fasn | Forward | GGAGGTGGTGATAGCCGGTAT (SEQ ID NO: 11) |
| | | Reverse | TGGGTAATCCATAGAGCCCAG (SEQ ID NO: 12) |
| | Scd1 | Forward | CCGGAGACCCTTAGATCGA (SEQ ID NO: 13) |
| | | Reverse | TAGCCTGTAAAAGATTTCTGCAAACC (SEQ ID NO: 14) |
| | Acc | Forward | AATGAACGTGCAATCCGATTTG (SEQ ID NO: 15) |
| | | Reverse | TITGCCACGTCATCTGGGITT (SEQ ID NO: 16) |
| | Cd36 | Forward | ATGGGCTGTGATCGGAACTG (SEQ ID NO: 17) |
| | | Reverse | GAGCCGCCGATCCACACG (SEQ ID NO: 18) |
| | Osm | Forward | CCCGGCACAATATCCTCGG (SEQ ID NO: 19) |
| | | Reverse | TCTGGIGTIGTAGTGGACCGT (SEQ ID NO: 20) |
| | Spp1 | Forward | ATCTCACCATTCGGATGAGTCT (SEQ ID NO: 21) |
| | | Reverse | TGTAGGGACGATTGGAGTGAAA (SEQ ID NO: 22) |
| | Tgfb1 | Forward | CTCCCGTGGCTTCTAGTGC (SEQ ID NO: 23) |
| | | Reverse | GCCTTAGTTTGGACAGGATCTG (SEQ ID NO: 24) |
| | Tnfa | Forward | CTTCTGTCTACTGAACTTCGGG (SEQ ID NO: 25) |
| | | Reverse | CAGGCTTGTCACTCGAATTTTG (SEQ ID NO: 26) |
| | Il12b | Forward | GTCCTCAGAAGCTAACCATCTCC (SEQ ID NO: 27) |
| | | Reverse | CCAGAGCCTATGACTCCATGTC (SEQ ID NO: 28) |
| | Ccl12 | Forward | ATTTCCACACTTCTATGCCTCCT (SEQ ID NO: 29) |
| | | Reverse | ATCCAGTATGGTCCTGAAGATCA (SEQ ID NO: 30) |
| | Ccl20 | Forward | ACTGTTGCCTCTCGTACATACA (SEQ ID NO: 31) |
| | | Reverse | GAGGAGGTTCACAGCCCTTTT (SEQ ID NO: 32) |
| | Cxcl9 | Forward | GGAGTTCGAGGAACCCTAGTG (SEQ ID NO: 33) |
| | | Reverse | GGGATTTGTAGTGGATCGTGC (SEQ ID NO: 34) |
| | F4/80 | Forward | ACCACAATACCTACATGCACC (SEQ ID NO: 35) |
| | | Reverse | AAGCAGGCGAGGAAAAGATAG (SEQ ID NO: 36) |
| | Col1a1 | Forward | GCTCCTCTTAGGGGCCACT (SEQ ID NO: 37) |
| | | Reverse | CCACGTCTCACCATTGGGG (SEQ ID NO: 38) |
| | Col1a2 | Forward | GTAACTTCGTGCCTAGCAACA (SEQ ID NO: 39) |
| | | Reverse | CCTTTGTCAGAATACTGAGCAGC (SEQ ID NO: 40) |
| | Col3a1 | Forward | CTGTAACATGGAAACTGGGGAAA (SEQ ID NO: 41) |
| | | Reverse | CCATAGCTGAACTGAAAACCACC (SEQ ID NO: 42) |
| | Gapdh | Forward | AAGGTCATCCCAGAGCTGAA (SEQ ID NO: 43) |
| | | Reverse | CTGCTTCACCACCTTCTTGA (SEQ ID NO: 44) |

TABLE 2

Target sequences used in this study

SEQ ID NO: 1: SQLE mRNA sequence (Genbank: NM_003129.3, 2989 bp)
GTCTGGGCCGAGCCCGCCCAGCTGGCTGAGACGCGTGGAGCCTGGCGGCGAGTGGGGGCGTGCGACGGTTACTCTGGTTACT
GGGGCCGCGCCGCGCTGGCGAGAGCCGCCGCCCGCGAGGGATGCTGGTGAGGAAGCCGTCGGGAGCCGCCGCCGCCATCTGA
GGGAGGTACCCTGGAAACCACCTTTTATCGGTGGGGAAGTGCAGTCGCGGTGGGCGGCTCTGGGGGCCAGCGAAACGGGAGG
CCTCTAAATCTTTAGGTTGGGGCTGCATTGCCCTGGAGCCGCACTCTTGAGTCCGAGGCCATCTTTTGTTGGAGAAGGCGTC
GGCGTTGGCGTTTTCCCGAGGTTGGGCTGTACAGTGTCTCCGTCCGCGGAAAAAGAAGCCTCTGAACCCGCGCCGGCCCGCA
GCCCCCGTGCCTTCCGGCCGCTGCTCGCCGTCGCCAGAGGCTAGGCCACGTTTCCCCCAGTGCCGAGGTGTTTCTGTGACCC
TCCCTCCACTCCCATTCCCTTCTGAAAGGGCACCTGCTCTTGGTGAGAAAAGAAATTATAGCACGAAGAGCCAGTATCAGAA
GAGTATCCATCACCCGCAGCAACCGCTCAGGGAACACCATCAAAAAGAAAAAAGGGAATATCTGGATTTCCTGGGCGAGG
AGGAGCGAGTCTGCTCGGGAGCTGTTCCAGCAGGCGATTTTTAAATACTGCTTTCTACGCCCTATACAACTTGGCTTCACAT
ACTTTTACACTAACTTTATATGATTTTTAAAAACTGGTCTGATCGGACTTCTCGTCCTGGGACACTGTTTACTGGAGTCTGG
CCGGCTCTCCGTGCTCCTCTTGGTACCTCATTTTGGGGAGAACCTTAAACCCACTCGAGCAGATAATCTCCGCCTTGACCGG
TGCCACCAAAGAAGCCTTGGAACCATGTGGACTTTTCTGGGCATTGCCACTTTCACCTATTTTTATAAGAAGTTCGGGGACT
TCATCACTTTGGCCAACAGGGAGGTCCTGTTGTGCGTGCTGGTGTTCCTCTCGCTGGGCCTGGTGCTCTCCTACCGCTGTCG
CCACCGAAACGGGGGTCTCCTCGGGCGCCAGCAGAGCGGCTCCCAGTTCGCCCTCTTCTCGGATATTCTCTCAGGCCTGCCT
TTCATTGGCTTCTTCTGGGCCAAATCCCCCCCTGAATCAGAAAATAAGGAGCAGCTCGAGGCCAGGAGGCGCAGAAAAGGAA
CCAATATTTCAGAAACAAGCTTAATAGGAACAGCTGCCTGTACATCAACATCTTCTCAGAATGACCCAGAAGTTATCATCGT
GGGAGCTGGCGTGCTTGGCTCTGCTTTGGCAGCTGTGCTTTCCAGAGATGGAAGAAAGGTGACAGTCATTGAGAGAGACTTA
AAAGAGCCTGACAGAATAGTTGGAGAATTCCTGCAGCCGGGTGGTTATCATGTTCTCAAAGACCTTGGTCTTGGAGATACAG
TGGAAGGTCTTGATGCCCAGGTTGTAAATGGTTACATGATTCATGATCAGGAAAGCAAATCAGAGGTTCAGATTCCTTACCC
TCTGTCAGAAAACAATCAAGTGCAGAGTGGAAGAGCTTTCCATCACGGAAGATTCATCATGAGTCTCCGGAAAGCAGCTATG
GCAGAGCCCAATGCAAAGTTTATTGAAGGTGTTGTGTTACAGTTATTAGAGGAAGATGATGTTGTGATGGGAGTTCAGTACA
AGGATAAAGAGACTGGAGATATCAAGGAACTCCATGCTCCACTGACTGTTGTTGCAGATGGGCTTTTCTCCAAGTTCAGGAA
AAGCCTGGTCTCCAATAAAGTTTCTGTATCATCTCATTTTGTTGGCTTTCTTATGAAGAATGCACCACAGTTTAAAGCAAAT
CATGCTGAACTTATTTTAGCTAACCCGAGTCCAGTTCTCATCTACCAGATTTCATCCAGTGAAACTCGAGTACTTGTTGACA
TTAGAGGAGAAATGCCAAGGAATTTAAGAGAATACATGGTTGAAAAAATTTACCCACAAATACCTGATCACCTGAAAGAACC
ATTCTTAGAAGCCACTGACAATTCTCATCTGAGGTCCATGCCAGCAAGCTTCCTTCCTCCTTCATCAGTGAAGAAACGAGGT
GTTCTTCTTTTGGGAGACGCATATAATATGAGGCATCCACTTACTGGTGGAGGAATGACTGTTGCTTTTAAAGATATAAAAC
TATGGAGAAAACTGCTAAAGGGTATCCCTGACCTTTATGATGATGCAGCTATTTTCGAGGCCAAAAAATCATTTTACTGGGC
AAGAAAAACATCTCATTCCTTTGTCGTGAATATCCTTGCTCAGGCTCTTTATGAATTATTTTCTGCCACAGATGATTCCCTG
CATCAACTAAGAAAAGCCTGTTTTCTTTATTTCAAACTTGGTGGCGAATGTGTTGCGGGTCCTGTTGGGCTGCTTTCTGTAT
TGTCTCCTAACCCTCTAGTTTTAATTGGACACTTCTTTGCTGTTGCAATCTATGCCGTGTATTTTTGCTTTAAGTCAGAACC
TTGGATTACAAAACCTCGAGCCCTTCTCAGTAGTGGTGCTGTATTGTACAAAGCGTGTTCTGTAATATTTCCTCTAATTTAC
TCAGAAATGAAGTATATGGTTCATTAAGCTTAAAGGGGAACCATTTGTGAATGAATATTTGGAACTTACCAAGTCCTAAGAG
ACTTTTGGAAGAGGATATATATAGCATAGTACCATACCACTTATAAAGTGGAAACTCTTGGACCAAGATTTGGATTAATTTG
TTTTTGAAGTTTTTTGTATATAAATATGTAAATACATGCTTTAATTTGCAATTTAAAATGAAGGGGTTAAATAAGTTAGACA
TTTAAAAGAAATGATTGTTACCATAAATTAGTGCTAATGCTGAGGAGAACTACAGTTTTTCTTTTGAATTTAGTATTTGAGA
TGAGTTGTTGGGACATGCAAATAAAATGAAGAATGAA SEQ ID NO: 2: CCDS47918.1: SQLE protein coding cDNA sequence (1722 bp)
ATGTGGACTTTTCTGGGCATTGCCACTTTCACCTATTTTTATAAGAAGTTCGGGGACTTCATCACTTTGGCCAACAGGGAGG
TCCTGTTGTGCGTGCTGGTGTTCCTCTCGCTGGGCCTGGTGCTCTCCTACCGCTGTCGCCACCGAAACGGGGGTCTCCTCGG
GCGCCAGCAGAGCGGCTCCCAGTTCGCCCTCTTCTCGGATATTCTCTCAGGCCTGCCTTTCATTGGCTTCTTCTGGGCCAAA
TCCCCCCCTGAATCAGAAAATAAGGAGCAGCTCGAGGCCAGGAGGCGCAGAAAAGGAACCAATATTTCAGAAACAAGCTTAA
TAGGAACAGCTGCCTGTACATCAACATCTTCTCAGAATGACCCAGAAGTTATCATCGTGGGAGCTGGCGTGCTTGGCTCTGC
TTTGGCAGCTGTGCTTTCCAGAGATGGAAGAAAGGTGACAGTCATTGAGAGAGACTTAAAAGAGCCTGACAGAATAGTTGGA
GAATTCCTGCAGCCGGGTGGTTATCATGTTCTCAAAGACCTTGGTCTTGGAGATACAGTGGAAGGTCTTGATGCCCAGGTTG
TAAATGGTTACATGATTCATGATCAGGAAAGCAAATCAGAGGTTCAGATTCCTTACCCTCTGTCAGAAAACAATCAAGTGCA
GAGTGGAAGAGCTTTCCATCACGGAAGATTCATCATGAGTCTCCGGAAAGCAGCTATGGCAGAGCCCAATGCAAAGTTTATT
GAAGGTGTTGTGTTACAGTTATTAGAGGAAGATGATGTTGTGATGGGAGTTCAGTACAAGGATAAAGAGACTGGAGATATCA
AGGAACTCCATGCTCCACTGACTGTTGTTGCAGATGGGCTTTTCTCCAAGTTCAGGAAAAGCCTGGTCTCCAATAAAGTTTC
TGTATCATCTCATTTTGTTGGCTTTCTTATGAAGAATGCACCACAGTTTAAAGCAAATCATGCTGAACTTATTTTAGCTAAC
CCGAGTCCAGTTCTCATCTACCAGATTTCATCCAGTGAAACTCGAGTACTTGTTGACATTAGAGGAGAAATGCCAAGGAATT
TAAGAGAATACATGGTTGAAAAAATTTACCCACAAATACCTGATCACCTGAAAGAACCATTCTTAGAAGCCACTGACAATTC
TCATCTGAGGTCCATGCCAGCAAGCTTCCTTCCTCCTTCATCAGTGAAGAAACGAGGTGTTCTTCTTTTGGGAGACGCATAT
AATATGAGGCATCCACTTACTGGTGGAGGAATGACTGTTGCTTTTAAAGATATAAAACTATGGAGAAAACTGCTAAAGGGTA
TCCCTGACCTTTATGATGATGCAGCTATTTTCGAGGCCAAAAAATCATTTTACTGGGCAAGAAAAACATCTCATTCCTTTGT
CGTGAATATCCTTGCTCAGGCTCTTTATGAATTATTTTCTGCCACAGATGATTCCCTGCATCAACTAAGAAAAGCCTGTTTT
CTTTATTTCAAACTTGGTGGCGAATGTGTTGCGGGTCCTGTTGGGCTGCTTTCTGTATTGTCTCCTAACCCTCTAGTTTTAA
TTGGACACTTCTTTGCTGTTGCAATCTATGCCGTGTATTTTTGCTTTAAGTCAGAACCTTGGATTACAAAACCTCGAGCCCT
TCTCAGTAGTGGTGCTGTATTGTACAAAGCGTGTTCTGTAATATTTCCTCTAATTTACTCAGAAATGAAGTATATGGTTCAT SEQ ID NO: 3: NP_003120: SQLE Homo sapiens, 574 amino acids.
MWTFLGIATFTYFYKKFGDFITLANREVLLCVLVFLSLGLVLSYRCRHRNGGLLGRQQSGSQFALFSDILSGLPFIGFFWAK
SPPESENKEQLEARRRRKGTNISETSLIGTAACTSTSSQNDPEVIIVGAGVLGSALAAVLSRDGRKVTVIERDLKEPDRIVG
EFLQPGGYHVLKDLGLGDTVEGLDAQVVNGYMIHDQESKSEVQIPYPLSENNQVQSGRAFHHGRFIMSLRKAAMAEPNAKFI
EGVVLQLLEEDDVVMGVQYKDKETGDIKELHAPLTVVADGLFSKFRKSLVSNKVSVSSHFVGFLMKNAPQFKANHAELILAN
PSPVLIYQISSSETRVLVDIRGEMPRNLREYMVEKTYPQIPDHLKEPFLEATDNSHLRSMPASFLPPSSVKKRGVLLLGDAY
NMRHPLTGGGMTVAFKDIKLWRKLLKGIPDLYDDAAIFEAKKSFYWARKTSHSFVVNILAQALYELFSATDDSLHQLRKACF
LYFKLGGECVAGPVGLLSVLSPNPLVLIGHFFAVAIYAVYFCFKSEPWITKPRALLSSGAVLYKACSVIFPLIYSEMKYMVH SEQ ID NO: 4: Partial coding sequence used to detect human SQLE by real-time PCR
(199 bp).
ATTCCCTTCTGAAAGGGCACCTGCTCTTGGTGAGAAAAGAAATTATAGCACGAAGAGCCAGTATCAGAAGAGTATCCATCAC
CCGCAGCAACCGCTCAGGGAACACCATCAAAAAGAAAAAAGGGAATATCTGGATTTCCTGGGCGAGGAGGAGCGAGTCTG
CTCGGGAGCTGTTCCAGCAGGCGATTTTTAAATAC

TABLE 3

Clinical characteristics of patient population

|  | Control | NAFLD | Non-NASH | NASH |
|---|---|---|---|---|
| All | 72 | 145 | 65 | 80 |
| Gender | | | | |
| Male | 34 (51.5) | 74 (55.7) | 36 (61) | 38 (51.3) |
| Female | 32 (48.5) | 59 (44.3) | 23 (39) | 36 (48.6) |
| Age (yr) | 48 (9.87) | 48 (9.67) | 47 (9.1) | 49 (10.1) |
| BMI** | 22.4 (2.7) | 27.4 (3.9) | 26.7 (3.8) | 28 (4.0) |
| Metabolic syndrome** | | | | |
| No | 64 (88.0) | 35 (24.1) | 19 (29.2) | 16 (20.0) |
| Yes | 8 (11.1) | 110 (75.9) | 46 (70.8) | 64 (80.0) |
| ALT (IU/L)** | 24.8 (11.32) | 73 (44.4) | 69 (40.59) | 76 (47.23) |
| Fasting glucose (mmol/L)**§ | 5.0 (0.4) | 6.5 (2.5) | 6.1 (2.0) | 6.9 (2.7) |
| LDL (mol/L | 3.0 (0.9) | 3.1 (0.89) | 3.2 (1.0) | 2.9 (0.77) |
| Total Cholesterol (mol/L)§ | 5.2 (1.24) | 5.3 (1.03) | 5.5 (1.21) | 5.1 (0.81) |
| Triglyceride (mmol/L)** | 1.3 (1.21) | 2.1 (1.12) | 2.1 (1.17) | 2.2 (1.07) |
| Steatosis grade 1/2/3§ | | 51/52/42 | 29/25/11 | 22/27/31 |
| Lobular inflammation 0/1/2§ | | 48/90/7 | 43/21/1 | 5/69/6 |
| Ballooning 0/1/2§ | | 55/82/8 | 47/17/1 | 8/65/7 |
| Fibrosis 0/1/2/3/4§ | | 58/50/16/10/11 | 45/20/0/0/0 | 13/30/16/10/1 |

Numbers in parentheses are percentage for categorical data or standard deviation for numerical data.
**Significant at p < 0.01, between control and NAFLD patients.
§Significant at p < 0.5. Significant at p < 0.01, between non-NASH and NASH patients.

TABLE 4

Correlations with SQLE in NAFLD patients

|  | SQLE | |
|---|---|---|
| Variables | rho | p value§ |
| Age | −0.35 | 0.604 |
| Triglyceride | 0.120 | 0.078 |
| Ballooning | 0.529 | 0.052 |
| Fibrosis | 0.161 | 0.048 |
| Lobular inflammation | 0.180 | 0.026 |
| Steatosis | 0.161 | 0.017 |
| BMI | 0.249 | 0.000 |

§p value corresponds to Ho: rho = 0. NAFLD: 145; control subjects: 72

TABLE 5

Multivariate logistic regression analysis of potential risk factors for NAFLD patients

| Variables | p value | OR | 95% CI |
|---|---|---|---|
| SQLE | 0.009 | 0.952 | 0.917-0.988 |
| BMI | 0.002 | 0.704 | 0.564-0.879 |
| ALT | 0.002 | 0.963 | 0.940-0.986 |
| HDL | 0.921 | 0.678 | 0.000-1430.368 |
| Fasting glucose | 0.003 | 0.102 | 0.022-0.465 |
| Metabolic syndrome | 0.075 | 0.227 | 0.044-1.158 |
| Cholesterol | 0.411 | 28.146 | 0.010-80250.878 |
| Triglyceride | 0.485 | 0.313 | 0.012-8.155 |
| LDL | 0.403 | 0.033 | 1.158E−5-96.376 |

Variables entered in the regression model:
age, body mass index (BMI),
alanine aminotransferase (ALT),
high density lipoprotein (HDL),
fasting glucose, metabolic syndrome, cholesterol, triglyceride, low density lipoprotein (LDL).

TABLE 6

Clinicopathological features of SQLE mRNA expression in CUHK HCC cohort

| Variable | Low SQLE expression (N = 45) | High SQLE expression (N = 43) | P value |
|---|---|---|---|
| Age, mean ± SD | 55.82 ± 13.32 | 54.05 ± 11.17 | 0.518 |
| Sex | | | |
| Male | 41 (91.1%) | 37 (86.0%) | 0.517 |
| Female | 4 (8.9%) | 6 (14.0%) | |
| TNM stage | | | |
| I, II | 27 (60.0%) | 15 (34.9%) | 0.021 |
| III, IV | 18 (40.0%) | 28 (65.1%) | |

TABLE 7

Clinicopathological features of SQLE mRNA expression in TCGA HCC cohort

| Variable | Low SQLE expression (N = 175) | High SQLE expression (N = 155) | P value |
|---|---|---|---|
| Age, mean ± SD | 60.3 ± 13.0 | 60.4 ± 12.7 | 0.917 |
| Sex | | | |
| Male | 111 (63.4%) | 109 (70.3%) | 0.199 |
| Female | 64 (36.6%) | 46 (29.7%) | |
| TNM stage | | | |
| I | 78 (49.4%) | 83 (55.3%) | 0.186 |
| II | 47 (29.7%) | 31 (20.7%) | |
| III, IV | 33 (20.9%) | 36 (24.0%) | |

LIST OF REFERENCES

1. M. Lazo, R. Hernaez, M. S. Eberhardt, S. Bonekamp, I. Kamel, E. Guallar, A. Koteish, F. L. Brancati, J. M. Clark. Prevalence of nonalcoholic fatty liver disease in the 1. United States: the Third National Health and Nutrition Examination Survey, 1988-1994. American journal of epidemiology 178, 38-45 (2013).
2. C. D. Williams, J. Stengel, M. I. Asike, D. M. Torres, J. Shaw, M. Contreras, C. L. Landt, S. A. Harrison. Prevalence of nonalcoholic fatty liver disease and nonalcoholic steatohepatitis among a largely middle-aged population utilizing ultrasound and liver biopsy: a prospective study. Gastroenterology 140, 124-131 (2011).
3. J. Yu, J. Shen, T. T. Sun, X. Zhang, N. Wong. Obesity, insulin resistance, NASH and hepatocellular carcinoma. Seminars in cancer biology 23, 483-491 (2013).
4. R. J. Perry, V T. Samuel, K. F. Petersen, G I. Shulman. The role of hepatic lipids in hepatic insulin resistance and type 2 diabetes. Nature 510, 84-91 (2014).
5. E. Fabbrini, S. Sullivan, S. Klein. Obesity and nonalcoholic fatty liver disease: biochemical, metabolic, and clinical implications. Hepatology 51, 679-689 (2010).
6. G Targher, C. D. Byrne, Obesity: Metabolically healthy obesity and NAFLD. Nature reviews. Gastroenterology & hepatology 13, 442-444 (2016).
7. V. W. Wong, W. C. Chu, G L. Wong, R. S. Chan, A. M. Chim, A. Ong, D. K. Yeung, K. K. Yiu, S. H. Chu, J. Woo, F. K. Chan, H. L. Chan. Prevalence of non-alcoholic fatty liver disease and advanced fibrosis in Hong Kong Chinese: a population study using proton-magnetic resonance spectroscopy and transient elastography. Gut 61, 409-415 (2012).
8. J. G Fan, G C. Farrell. Epidemiology of non-alcoholic fatty liver disease in China. Journal of hepatology 50, 204-210 (2009).
9. D. Schuppan, J. M. Schattenberg. Non-alcoholic steatohepatitis: pathogenesis and novel therapeutic approaches. Journal of gastroenterology and hepatology 28 Suppl 1, 68-76 (2013).
10. T. Hardy, D. A. Mann. Epigenetics in liver disease: from biology to therapeutics. Gut 65, 1895-1905 (2016).
11. M. E. Rinella, A. J. Sanyal. NAFLD in 2014: Genetics, diagnostics and therapeutic advances in NAFLD. Nature reviews. Gastroenterology & hepatology 12, 65-66 (2015).
12. G N. Ioannou. The Role of Cholesterol in the Pathogenesis of NASH. Trends in endocrinology and metabolism: TEM 27, 84-95 (2016).
13. G A. Michelotti, M. V. Machado, A. M. Diehl. NAFLD, NASH and liver cancer. Nature reviews. Gastroenterology & hepatology 10, 656-665 (2013).
14. Mittal S, El-Serag H B. Epidemiology of hepatocellular carcinoma: consider the population. J Clin Gastroenterol 47, Suppl:52-6 (2013). Chaudhary K, Poirion O B, Lu L, Garmire L X. Deep Learning-Based Multi-Omics Integration Robustly Predicts Survival in Liver Cancer. Clin Cancer Res 5, (2017) [Epub ahead of print]
16. Yu S J. A concise review of updated guidelines regarding the management of hepatocellular carcinoma around the world: 2010-2016. Clin Mol Hepatol 22, 7-17 (2016)
17. Heimbach J K, Kulik L M, Finn R S, Sirlin C B, Abecassis M M, Roberts L R, Zhu A X, Murad M H, Marrero J A. AASLD guidelines for the treatment of hepatocellular carcinoma. Hepatology 67, 258-380 (2018).
18. Llovet J M, Ricci S, Mazzaferro V, Hilgard P, Gane E, Blanc J F, de Oliveira A C, Santoro A, Raoul J L, Forner A, Schwartz M, Porta C, Zeuzem S, Bolondi L, Greten T F, Galle P R, Seitz J F, Borbath I, Haussinger D, Giannaris T, Shan M, Moscovici M, Voliotis D, Bruix J; SHARP Investigators Study Group. Sorafenib in advanced hepatocellular carcinoma. N Engl J Med 359, 378-390 (2008).
19. Kudo M. Systemic Therapy for Hepatocellular Carcinoma: 2017 Update. Oncology 93, Suppl 1:135-146 (2017).

What is claimed is:

1. A method for inhibiting progression of a non-alcoholic fatty liver disease (NAFLD) in a human subject, comprising orally administering to the human subject terbinafine in the amount of about 80 mg/kg bodyweight for about 8-9 weeks.

2. The method of claim 1, wherein the NAFLD is steatosis.

3. The method of claim 1, wherein the NAFLD is non-alcoholic steatosis (NASH).

4. The method of claim 1, wherein the NAFLD is liver fibrosis.

5. The method of claim 1, wherein the NAFLD is cirrhosis.

6. The method of claim 1, wherein the NAFLD is a liver cancer associated with or caused by a non-alcoholic fatty liver disease.

* * * * *